US009645148B2

(12) United States Patent
McBride et al.

(10) Patent No.: US 9,645,148 B2
(45) Date of Patent: *May 9, 2017

(54) **IMMUNOREACTIVE PROTEIN ORTHOLOGS OF *EHRLICHIA CANIS* AND *E. CHAFFEENSIS***

(71) Applicant: Research Development Foundation, Carson City, NV (US)

(72) Inventors: Jere W. McBride, League City, TX (US); Christopher K. Doyle, Bacliff, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/818,221

(22) Filed: Aug. 4, 2015

(65) Prior Publication Data

US 2016/0084836 A1    Mar. 24, 2016

Related U.S. Application Data

(60) Continuation of application No. 14/072,029, filed on Nov. 5, 2013, now Pat. No. 9,140,702, which is a division of application No. 11/917,390, filed as application No. PCT/US2006/023397 on Jun. 15, 2006, now Pat. No. 8,591,906.

(60) Provisional application No. 60/691,058, filed on Jun. 16, 2005.

(51) Int. Cl.
*G01N 33/569* (2006.01)
*C07K 14/29* (2006.01)
*A61K 39/00* (2006.01)

(52) U.S. Cl.
CPC ........ *G01N 33/56911* (2013.01); *C07K 14/29* (2013.01); *A61K 39/00* (2013.01); *G01N 2333/195* (2013.01); *G01N 2469/10* (2013.01)

(58) Field of Classification Search
None
See application file for complete search history.

(56) References Cited

FOREIGN PATENT DOCUMENTS

WO    WO 2004/042037    5/2004

OTHER PUBLICATIONS

Barbet, et al., "A subset of Cowdria ruminantium genes important for immune recognition and protection," *Gene*, 275:287-298, 2001.

Database EMBL [Online], "Cowdria ruminantium clone 26hw hypothetical tryptophanyl-tRNA ligase gene, partial cds; cell surface mucin-like protein gene, complete cds; and unknown gene," XP002406355, Oct. 2001.

Doyle, et al., "Differentially expressed and secreted major immunoreactive protein orthologs of *Ehrlichia canis* and *E. chaffeensis* elicit early antibody responses to epitopes on glycosylated tandem repeats," *Infect. Immun.*, 74:711-720, 2006.

Doyle, et al., "Molecular characterization of *E. canis* gp36 and *E. chaffeensis* gp47 tandem repeats among isolates from different geographic locations," *Ann NY Acad. Sci.*, 1063:433-435, 2005.

Mark and Lennart, "Molecular dynamics simulations of the Ala-pro dipeptide in water: conformational dynamics of Trans and Cis isomers using different water models" *J. Phys. Chem. B*, 105:8028-8035, 2001.

Mavromatis, et al., "The genome of the obligately intracellular bacterium *Ehrlichia canis* reveals themes of complex membrane structure and immune evasion strategies," *J. Bacteriol.*, 188:4015-4023, 2006.

McBride, et al., "Glycosylation of homologous immunodominant proteins of *Ehrlichia chaffeensis* and *Ehrlichia canis*," *Infect. Immun.*, 68:13-18, 2000.

McBride, et al., "Immunodiagnosis of *Ehrlichia canis* infection with recombinant proteins," *J. Clin. Microbiol.*, 39:315-322, 2001.

McBride, et al., "Kinetics of antibody response to *Ehrlichia canis* immunoreactive proteins," *Infect. Immun.*, 71:2516-2524, 2003.

McBride, et al., "Novel Immunoreactive glycoprotein orthologs of *Ehrlichia* spp," *Ann NY Acad. Sci.*, 990:678-684, 2003.

Office Action issued in Canadian Application No. 2,612,302, dated Mar. 7, 2013.

Office Action issued in Canadian Application No. 2,612,302, dated Feb. 20, 2014.

Office Action issued in U.S. Appl. No. 11/917,390, dated Apr. 30, 2010.

Office Action issued in U.S. Appl. No. 11/917,390, dated Dec. 12, 2012.

Office Action issued in U.S. Appl. No. 14/072,029, dated Jun. 5, 2014.

Office Action issued in U.S. Appl. No. 14/072,029, dated Oct. 14, 2014.

PCT International Search Report issued in Application No. PCT/US2006/023397, mailed Dec. 12, 2006.

Rikihisa, et al., "Western immunoblot analysis of *Ehrlichia chaffeensis, E. canis,* or *E. ewingii* infections in dogs and humans," *J Clin. Microbiol.*, 32:2107-2112, 1994.

Singu, et al., "*Ehrlichia chaffeensis* expresses macrophage- and tick cell-specific 28-kilodalton outer membrane proteins," *Infect. Immun.*, 73:79-87, 2005.

*Primary Examiner* — Oluwatosin Ogunbiyi
(74) *Attorney, Agent, or Firm* — Parker Highlander PLLC

(57) ABSTRACT

The present invention concerns gp36 immunoreactive compositions for *E. canis* and gp 47 immunoreactive compositions for *E. chaffeensis*. In particular, epitopes for *E. canis* gp36 and *E. chaffeensis* gp 47 are disclosed. In certain embodiments, the immunoreactive compositions comprise tandem repeats having carbohydrate moieties.

13 Claims, 9 Drawing Sheets

*E. canis* gp36

Ja | 429 | | 84

Ok | 429 | | 90

Dem | 429 | | 84

*E. chaffeensis* gp47

Ark | 471 | | 78

Sap | 462 | | 126

FIG. 1

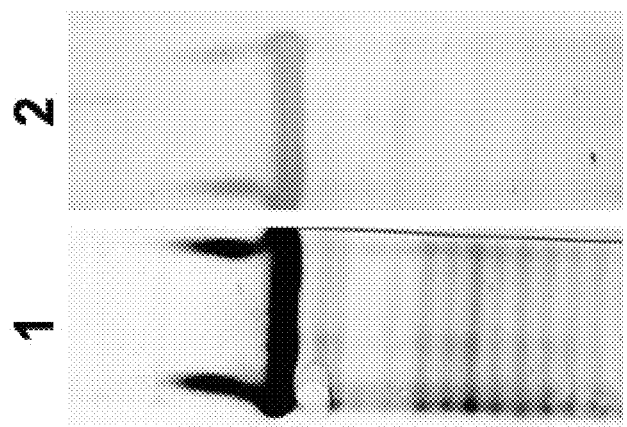
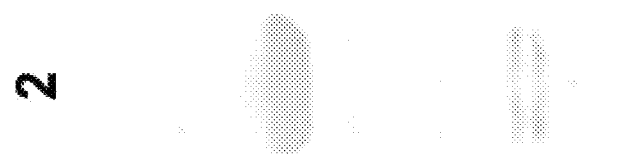
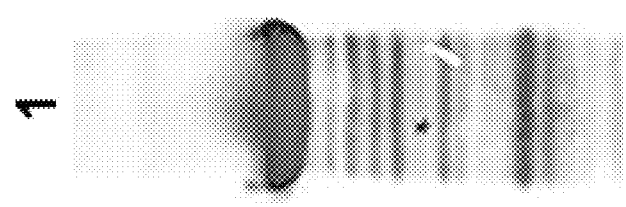
FIGS. 2A-B

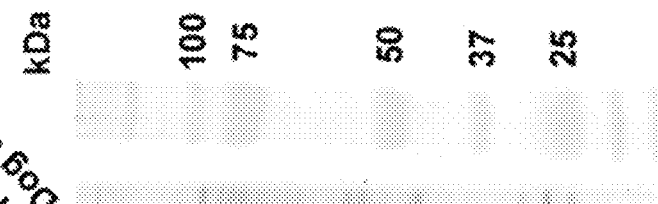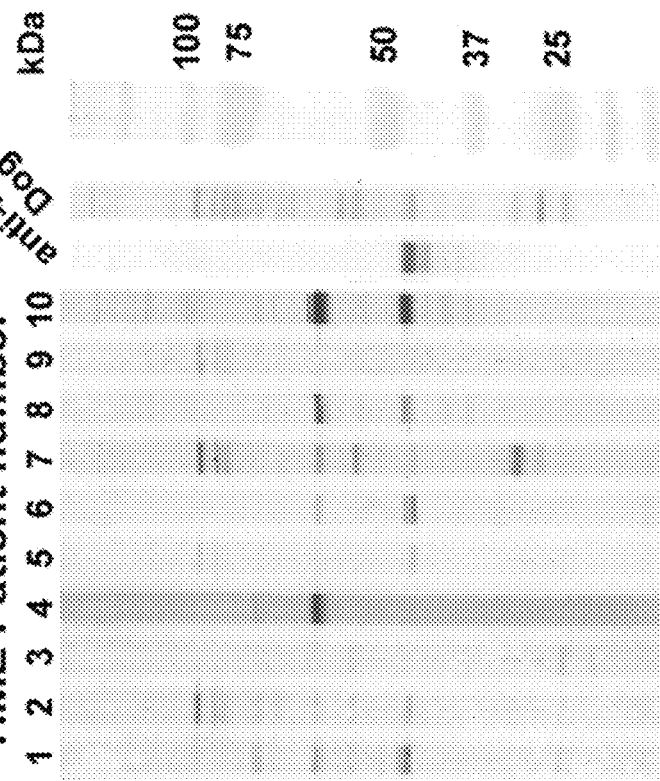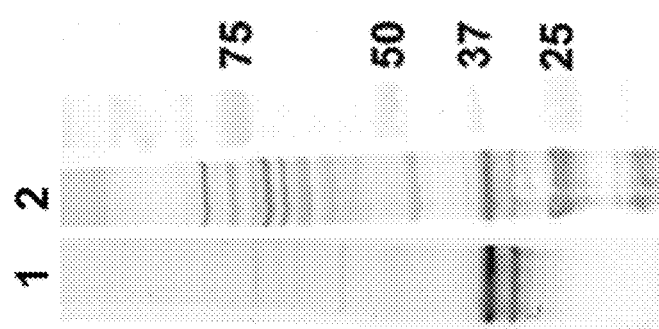
FIGS. 3A-B

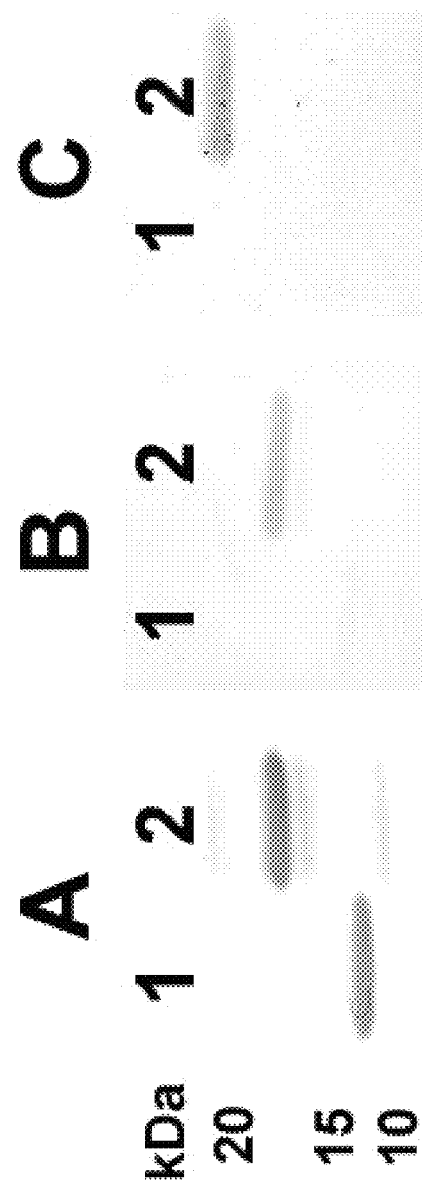
FIGS. 5A-C

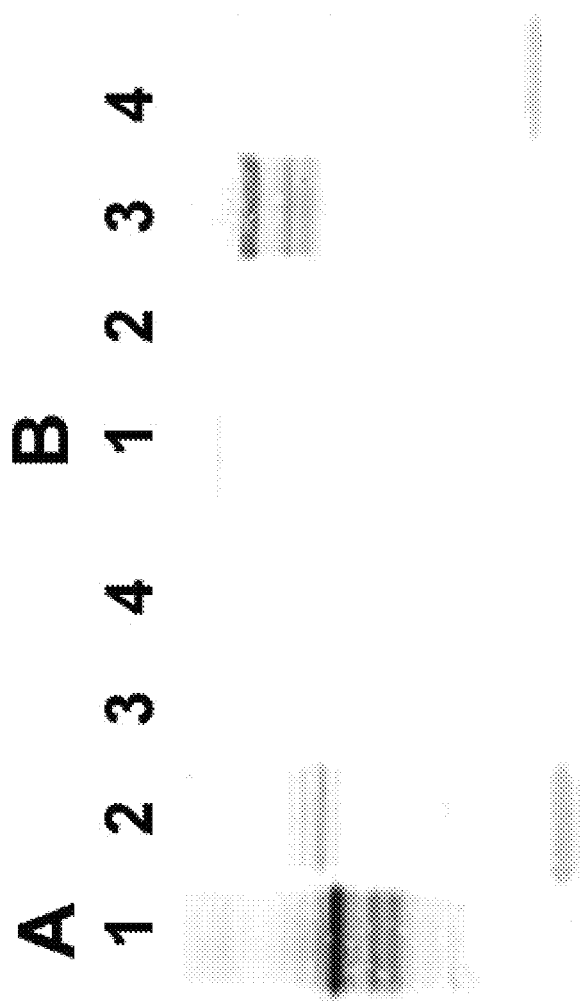
FIGS. 6A-B

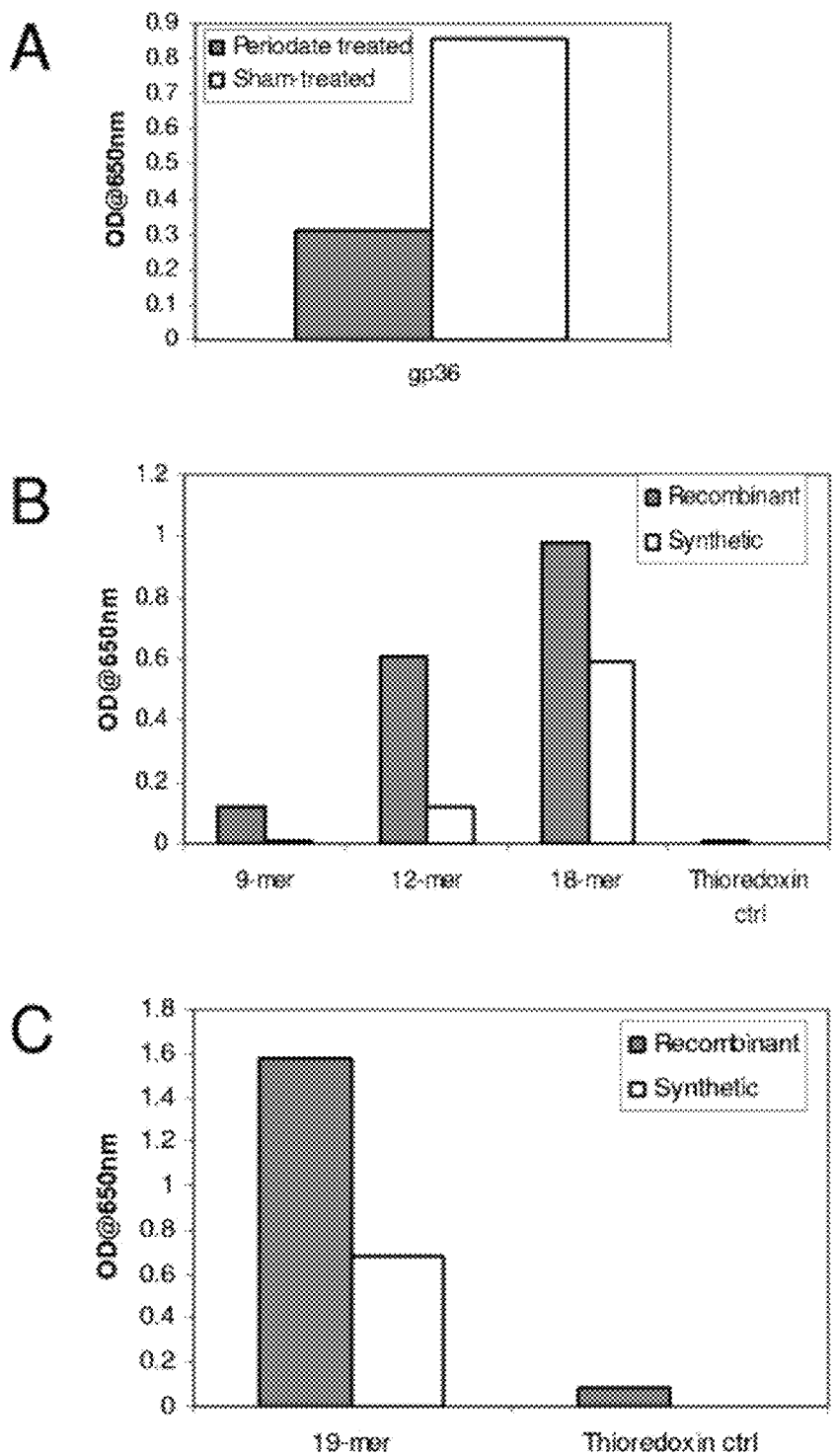
FIGS. 7A-C

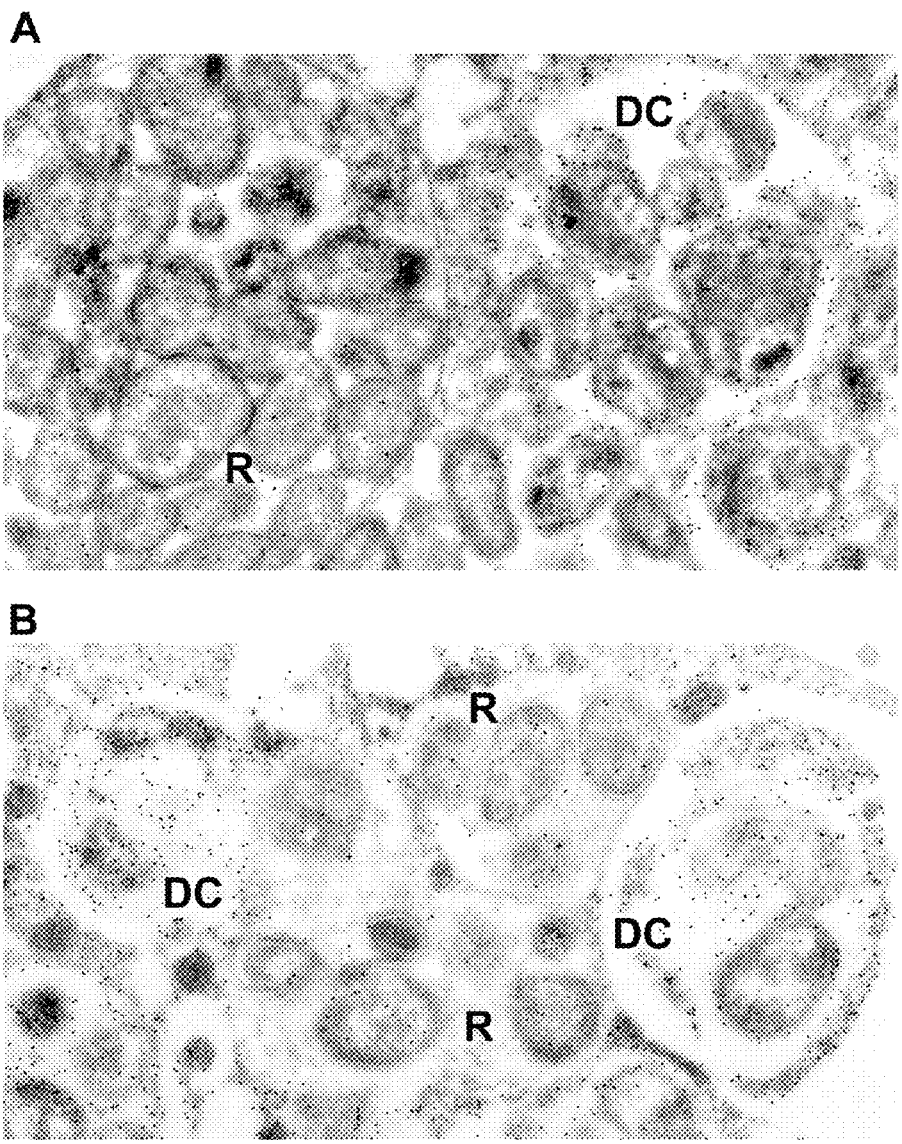
FIGS. 8A-B

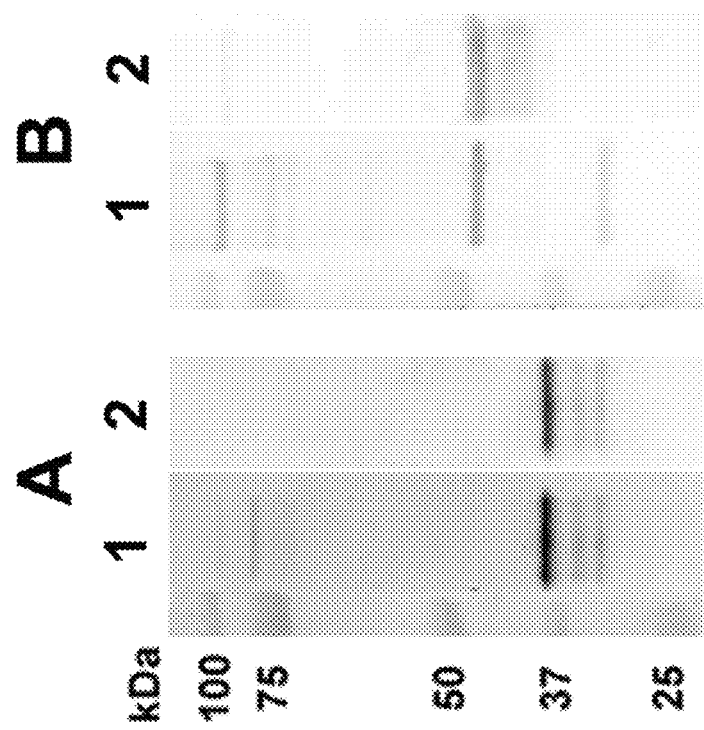
FIGS. 9A-B

SEQUENCE LISTING

```
<160> NUMBER OF SEQ ID NOS: 69

<210> SEQ ID NO 1
<211> LENGTH: 3829
<212> TYPE: DNA
<213> ORGANISM: Ehrlichia ruminantium

<400> SEQUENCE: 1
gatccagaaa attcagtgct attttcacag tcttttattc cagcacatac agagttacta      60
tggatattca gttgcattac ttcaacaggt caactaaata gaatgactca atttaaagaa     120
aaaagccgca ataaagtttc tacagcttct ttaggattgt acagctatcc tgtattaatg     180
gcagctgata tattacttta ccaagcaaat atagtacctg taggcattga tcaaaaacaa     240
cacttagaat tagcacgaga cattgctcaa gcttttaaca caaaatacaa tacgcaatac     300
tttcaactgc cagaaccatt aattgtacag gaatcagcaa aaattatgag tttaagagac     360
ggtaaaaaga aaatgagtaa atctgatgta tcagattatt cacgaattaa tttagaagat     420
agtaacgact taattgctca aaaaattaac aaagcaacca ctgactctat tgtaggtttt     480
gactttacaa gtttaaacaa taggcctgca gtaaagaatc ttgttaatat ttatgctaca     540 cttttcaaata ttagtataga acaaacatgt actaacattg caagcttcac tactaaacaa     600
tttaaagaag aactaacaga attaattatt aataacattg caccaatacg acaaaaatta     660
agagagttat tagaagacat agaatattta cgaagcatat taatgacagg aaataacaag     720
gctgcatcta ttgcacataa gcacataata gaaattaaaa agattgcagg atattggtaa     780
taattataca aaattcatta atactcaaag tcatatcctt tggttattat tgtatgtgtc     840
atggtgttta aaaacataaa atagttttta ttaccaatat gtaaagatca aggaaattat     900
tacaatatat taatatcaac agtctcagta tgttgagaga ttcatattta tttaattaaa     960
ctataatctt cttgactatc atctttatat attaggccat tttatataaa aaaaaagaaa    1020
agaaatccta ctcattaata tctaaatatt aaaagagcta ctacaaaata actaccataa    1080
tacatctata gcaaaataaa gaatccatag catcaaaata tctatactaa attcactatc    1140
catatctagt ccgcatctat aatactataa aattaacact gtataacaaa atatgtagtg    1200
ttaatgccta taaaattaac aatattacta gaaaattaaa tacccaatta taatactacc    1260
aaagatatcc actaaataaa agtacaataa taataaacaa aaagagacat agaggaatag    1320 ttatattttta tatcagctac taactgttat aaacatatag cttaatatat atttactcaa    1380
gtccataaaa tacacattct cacaagagtt agtacacagt aaagagaaaa aaaagttagc    1440
```

```
acttgaagag ttcacttacc aatatactat tcagtttcat taaaaaaatt acacaatttt    1500
ttttctaaat ataattcaga atttactatt ctatatagtg attctattca cttaagcatt    1560
atctatatac atagtatatc acaaatctca ctttaatatc cttttacac actcatcaaa     1620 tccaatactc ataataaaat aagttattta ttcaaaatac tattgaatat taacgaaaat    1680
ctataggaca atataacatt agatgttatt aaccatttt ataataaaca gtatacactg     1740
ttgtattact ttaacttcaa tttatagaaaa tgaaaaatag tatagaattt aaagttatta   1800
ttaatgctct ataatcctat ttatacccta gtgtaaaatc taaataatat ttttcttact    1860
tatcaataaa aacaataaat attaccacat aacctaagca tactcttcat aaacttaagt    1920
aacaatatct cattatattt attttttcaaa aataaactat aagcaattat taccatctaa   1980
gcttatctaa atataattta tctatactat accattataa atctgattac tataaagatt    2040
gaactatagt catccaaagg tttatacttg cttaatttta ctttacacaa aacaacaatt    2100
aaaaattata tataataaaa aatttactat tataaaaggc taacaaataa tcaactttac    2160
gtacatgagt aaattctttc tgattatgct atttttaataa taaaaaatac tatattttgt   2220
gagaaaaata tagtaataat atgctgtaat taacacacga aaggatttac ctcctgtatt    2280
tataggagat aaatccttgt acagatacca caattaaata aaacaattaa ttcatcttaa    2340
tattatttat atggttttca ttagatgcca gtaaatactc tttcaccact acgaccacca    2400
aatgtaaatc cttttgctac ttctgggcta cttgttacaa ctgatccttc tgggctactt    2460
gttacaactg atccttctgg gctacttgtt acaactgatc cttctgggct acttgttaca    2520
actgatcctt ctgggctact tgttacaact gatccttctg gctacttgt tacaactgat    2580 ccttctgggc tacttgttac aactgatcct tctgggctac ttgttacaac tgatccttct    2640
gggctacttg ttacaactga tccttctggg ctacttgtta caactgatcc ttctgggcta    2700
cttgttacaa ctgatccttc tgggctactt gttacaactg atccttctgg gctacttgtt    2760
acaactgatc cttctgggct acttgttaca actgatcctt ctgggctact tgttacaact    2820
gatccttctg gctacttgt tacaactgat ccttctgggc tacttgttac aactgatcct    2880
tctgggctac ttgttacaac tgatccttct gggctacttg ttacaactga tccttctggg    2940
ctacttgtta caactgatcc ttctgggcta cttgttacag ctgctccttc tgggctattt    3000
gttacagttg tatcaacacc tgagatcacc ttatcatagc acacatttaa tggatgaaga    3060
ttaagagaaa aattagaacc ttgttgtaaa aactctgaaa aaggttccat taaatttact    3120
acaaaagaag cttgtaagct gtggtttaat acatcaagtg caatatgttt accagtaaca    3180
ccatgaaaat ctgaaagtac gtgaccatta ctcgtaaaca taacatgata ttcgccatga    3240
tgattttcat gaccttcttc atgctcatga ggatgatagc caatctccat tgtaatatca    3300
ccatttgaaa cagagaattg attattacta tagatactta aatcatttcc aaaatcaata    3360
ttgtcaattc ttgttgttaa atgaagcata caatcttctg ctgttgaatg aaccatacag    3420
taacctatta gtacaatgca tatttatatt atatatttta gtgtgttaat tttgttttaa    3480
gtacaacttt gtgtagtaaa taagtcacac tacttttcaa tctctacaat tacgaagata    3540
cagatgtaaa ttcgctattt tgagaagccg tatcagtaac agatactaaa ttagcactta    3600
cacaatcaac attatgattg tggcaatctt ctgttaatgg atgaagatta agagaaaaat    3660
tagaaccttg ttgtaaaaac tctgaaaaag gttccattaa atttactaca aagaagctt    3720 gtaagctgtg atttaataca tcaagtgcaa tatgttgacc agtaacacca tgaaaatctg    3780
aaagtacgtg accattattt ataaacataa catgatattc cccatgatc                3829
```

-continued

<210> SEQ ID NO 2
<211> LENGTH: 2489
<212> TYPE: DNA
<213> ORGANISM: Ehrlichia canis

<400> SEQUENCE: 2

| | | | | | |
|---|---|---|---|---|---|
| aaacaatcta | ccgggcatac | ttcaacacaa | tcagtatatt | tgcatcttat | gcacttatcg | 60 |
| gtaacgaagt | gtgtcattac | agagttatta | ataataaagt | aaccattttt | attgtaatgt | 120 |
| ttttcttgc | caagttcaat | taatttattg | tttacataag | gtataaatgc | ggattatggt | 180 |
| taaattatgc | atgtcgtaag | tataaaataa | gttgataagt | gttttgttat | atcctaatag | 240 |
| atataggagg | cattggttct | atataaatgt | tattttatga | taaataatta | atttttaaca | 300 |
| ggatgaattt | gtgcaatgta | tttaaattaa | gaggattttt | atggatattg | ataacaataa | 360 |
| tgtgactaca | tcaagtacgc | aagataaaag | tgggaattta | atggaagtga | ttatgcgtat | 420 |
| attaaatttt | ggtaataatt | cagatgagaa | agtaagcaat | gaagacacta | agttcttgt | 480 |
| agagagttta | caacctgctg | tgaatgacaa | tgtaggaaat | ccatcaagtg | aagttggtaa | 540 |
| agaagaaaat | gctcctgaag | ttaaagcgga | agatttgcaa | cctgctgtag | atggtagtgt | 600 |
| agaacattca | tcaagtgaag | ttgggaaaaa | agtatctgaa | actagtaaag | aggaaagtac | 660 |
| tcctgaagtt | aaagcagaag | atttgcaacc | tgctgtagat | ggtagtatag | aacattcatc | 720 |
| aagtgaagtt | ggagaaaaag | tatctaaaac | tagtaaagag | gaaagtactc | ctgaagttaa | 780 |
| agcagaagat | ttgcaacctg | ctgtagatga | tagtgtggaa | cattcatcaa | gtgaagttgg | 840 |
| agaaaaagta | tctgaaacta | gtaaagagga | aaatactcct | gaagttaaag | cagaagattt | 900 |
| gcaacctgct | gtagatggta | gtatagaaca | ttcatcaagt | gaagttggag | aaaaagtatc | 960 |
| taaaactagt | aaagaagaaa | gtactcctga | agttaaagca | gaagatttgc | aacctgctgt | 1020 |
| agatgatagt | gtggaacatt | catcaagtga | agttggagaa | aaagtatctg | aaactagtaa | 1080 |
| agaagaaaat | actcctgaag | ttaaagcgga | agatttgcaa | cctgctgtag | atggtagtgt | 1140 |
| agaacattca | tcaagtgaag | ttgggaaaaa | agtatctgaa | actagtaaag | aggaaagtac | 1200 |
| tcctgaagtt | aaagcagaag | atttgcaacc | tgctgtagat | gatagtgtgg | aacattcatc | 1260 |
| aagtgaagtt | ggagaaaaag | tatctgaaac | tagtaaagag | gaaaatactc | ctgaagttag | 1320 |
| agcagaagat | ttgcaacctg | ctgtagatgg | tagtgtagaa | cattcatcaa | gtgaagttgg | 1380 |
| agaaaaagta | tctgaaacta | gtaaagagga | aagtactcct | gaagttaaag | cagaagattt | 1440 |
| gcaacctgct | gtagatagta | gtatagaaca | ttcatcaagt | gaagttggga | aaaagtatc | 1500 |
| tgaaactagt | aaagaggaaa | gtactcctga | agttaaagca | gaagatttgc | aacctgctgt | 1560 |
| agatggtagt | gtagaacatt | catcaagtga | agttggagaa | aaagtatctg | aaactagtaa | 1620 |
| agaggaaaat | actcctgaag | ttaaagcaga | agatttgcaa | cctgctgtag | atggtagtgt | 1680 |
| agaacattca | tcaagtgaag | ttggagaaaa | agtatctgaa | actagtaaag | aggaaaatac | 1740 |
| tcctgaagtt | aaagcggaag | atttgcaacc | tgctgtagat | ggtagtgtag | aacattcatc | 1800 |
| aagtgaagtt | ggagaaaaag | tatctgaaac | tagtaaggaa | gaaagtactc | ctgaagttaa | 1860 |
| agcggaagat | ttgcaacctg | ctgtagatga | tagtgtagaa | cattcatcaa | gtgaagttgg | 1920 |
| agaaaaagta | tctgaaacta | gtaaagaaga | agtactcct | gaagttaaag | cggagatttg | 1980 |
| gcaacctgct | gtagatggta | gtgtggaaca | ttcatcaagt | gaagttggag | aaaaagtatc | 2040 |
| tgagactagt | aaagaggaaa | gtactcctga | agttaaagcg | gaagtacagc | tgttgcagaa | 2100 |
| tggtaatcct | gttcctttaa | atcctatgcc | ttcaattgat | aatattgata | ctaatataat | 2160 |

| | |
|---|---|
| attccattac cataaagact gtaaaaaagg ttcagctgta ggaacagatg aaatgtgttg | 2220 |
| tcctgtatca gaattaatgg ctggggaaca tgttcatatg tatggaattt atgtctatag | 2280 |
| agttcaatca gtaaaggatt taagtggtgt atttaatata gatcattcta catgtgattg | 2340 |
| taatttagat gtttattttg taggatacaa ttcttttact aacaaagaaa cagttgattt | 2400 |
| aatataatat tgtagtacgt aagctttata aaattgtata ttgaatagca agtaatgcta | 2460 |
| atgcagtatt gcttgctatt tttttgttt | 2489 |

```
<210> SEQ ID NO 3
<211> LENGTH: 2100
<212> TYPE: DNA
<213> ORGANISM: Ehrlichia chaffeensis

<400> SEQUENCE: 3
```

| | |
|---|---|
| tccttcatag aaacaatcta ccgggcatac ttcaacacaa tcagtgtatt tgcatcttat | 60 |
| gcacctatcc gttataaagt gtgtcattac agggttatta ataataatgt aacggttttt | 120 |
| attgtaatgt ttttttcttgc caagttcaat tagtatttat tattttacaa ggtatagatg | 180 |
| tggagttgta gttaaactta tacatcgtag agttaagtag tttggttaat gtttaggtaa | 240 |
| catcctaata cgtatatgag ctatcaattc tatagagtat gttattttat gatagagaat | 300 |
| tgattgtgga gttggatttg gcaatacgtt taaaattaaa ggagattttt atggatattg | 360 |
| ataatagtaa cataagtaca gccgatatac ggagtaaatac tgatggcttg atagacataa | 420 |
| ttatgcgtat attaggtttt ggtaataaga atattgtgca accacaggat ctgggttctg | 480 |
| aaatttatca gcaagagcaa gaagatgaca cagtctctca accttcatta gagccatttg | 540 |
| ttgcagaaag tgaagtttct aaagttgaac aagaaaaaac taaccctgag gttttaataa | 600 |
| aagatttgca agatgttgcg agtcatgaat ctggtgtatc agatcagcca gctcaagttg | 660 |
| ttacagagag agaaaatgaa attgaatccc atcaaggaga aacagaaaaa gaaagtggaa | 720 |
| taactgaatc tcatcagaaa gaagatgaaa tagtatctca atcttcatca gagccatttg | 780 |
| ttgcagaaag tgaagtttct aaagttgaac aagaagaaac taaccctgaa gttttaataa | 840 |
| aagatttgca agatgttgcg agtcatgaat ctggtgtatc agatcagcca gctcaagttg | 900 |
| ttacagagag agaaagtgaa attgaatccc atcaaggaga aacagaaaaa gaaagtggaa | 960 |
| taactgaatc tcatcagaaa gaagatgaaa tagtatctca accttcatca gagccatttg | 1020 |
| ttgcagaaag tgaagtttct aaagttgaac aagaagaaac taaccctgaa gttttaataa | 1080 |
| aagatttgca agatgttgcg agtcatgaat ctggtgtatc agatcagcca gctcaagttg | 1140 |
| ttacagagag agaaagtgaa attgaatccc atcaaggaga aacagaaaaa gaaagtggaa | 1200 |
| taactgaatc tcatcagaaa gaagatgaaa tagtatctca accttcatca gagccatttg | 1260 |
| ttgcagaaag tgaagtttct aaagttgaac aagaagaaac taaccctgaa gttttaataa | 1320 |
| aagatttgca agatgttgcg agtcatgaat ctggtgtatc agatcagcca gctcaagttg | 1380 |
| ttacagagag agaaagtgaa attgaatccc atcaaggaga aacagaaaaa gaaagtggaa | 1440 |
| taactgaatc tcatcagaaa gaagatgaaa tagtatctca accttcatca gagccatttg | 1500 |
| ttgcagaaag tgaagtttct aaagttgaac aagaaaaaac taaccctgaa attctagtag | 1560 |
| aagatttgcc attaggtcaa gtgattccgg ttgttgtaga gaaagatgaa atgtttgcac | 1620 |
| cttcatttaa tccaatcgtt ataaaggagg aagataaagt ttgtgaaact tgcgaacaag | 1680 |
| aatttgagat tgtaaaggat tcacagactg taaaaggtag tgaagatata atatcaccta | 1740 |
| tgcaatgctt agaaagtatg gattctatag tttcaacaat atttgaaagt ggaatgttat | 1800 |

```
gtcctatgtc aaaacctgga cagtatgttt gtgggtatga aatgtatatg tatggatttc   1860
aagatgtgaa agacttatta ggtggtttat aagtaatgt tcctgtgtgt tgtaatgtta   1920
gcctttattt tatggaacat aattacttta ctaaccatga gaatattaat cacaatgtag   1980
taaatgatat tgtataattg taaggttag tcttgagata gcaagtgatg cttttattaa   2040
gtattgcttg ctattttttt gtttatttac ctgcttttta tatgggagaa atcatatatt   2100
```

<210> SEQ ID NO 4
<211> LENGTH: 1476
<212> TYPE: DNA
<213> ORGANISM: Ehrlichia chaffeensis

<400> SEQUENCE: 4

```
gagaattgat tgtggagttg gatttggcaa tacgtttaaa attaaaggag atttttatgg     60
atattgataa tagtaacata agtacagccg atatacggag taatactgat ggcttgatag    120
acataattat gcgtatatta ggttttggta ataagaatat tgtgcaacca caggatctgg    180
gttctgaaat ttatcagcaa gagcaagaag atgacacagt ctctcaacct tcattagagc    240
catttgttgc agaaagtgaa gtttctaaag ttgaacaaga aaaaactaac cctgaggttt    300
taataaaaga tttgcaagat gttgcgagtc atgaatctgg tgtatcagat cagccagctc    360
aagttgttac agaaagagaa aatgaaattg aatcccatca aggagaaaca gaaaaagaaa    420
gtggaataac tgaatctcat cagaaagaag atgaaatagt atctcaacct tcatcagagc    480
catttgttgc agaaagtgaa gtttctaaag ttgaacaaga gaaactaac cctgaagttt    540 taataaaaga tttgcaagat gttgcgagtc atgaatctgg tgtatcagat cagccagctc    600
aagttgttac agagagagaa agtgaaattg aatcccatca aggagaaaca gaaaaagaaa    660
gtggaataac tgaatctcat cagaaagaag atgaaatagt atctcaatct tcatcagagc    720
catttgttgc agaaagtgaa gtttctaaag ttgaacaaga gaaactaac cctgaagttt    780 taataaaaga tttgcaagat gttgcgagtc atgaatctgg tgtatcagat cagccagctc    840
aagttgttac agagagagaa agtgaaattg aatcccatca aggagaaaca gaaaaagaaa    900
gtggaataac tgaatctcat cagaaagaag atgaaatagt atctcaacct tcatcagagc    960
catttgttgc agaaagtgaa gtttctaaag ttgaacaaga aaaaactaac cctgaaattc   1020
tagtagaaga tttgccatta ggtcaagtga ttccggttgt tgtagagaaa gatgaaatgt   1080
ttgcaccttc atttaatcca atcgttataa aggaggaaga taaagtttgt gaaacttgcg   1140
aacaagaatt tgagattgta aaggattcac agactgtaaa aggtagtgaa gatataatat   1200
cacctatcga atgcttagaa agtatggatt ctatagtttc aacaatattt gaaagtggaa   1260
tgttatgtcc tatgtcaaaa cctggacagt atgtttgtgg gtatgaaatg tatatgtatg   1320
gatttcaaga tgtgaaagac ttattaggtg gtttattaag taatgttcct gtgtgttgta   1380
atgttagcct ttattttatg gaacataatt actttactaa ccatgagaat attaatcaca   1440
atgtagtaaa tgatattgta taattgtaag gtttag                             1476
```

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
atgcttcatt taacaacaga                                              20

<210> SEQ ID NO 6
<211> LENGTH: 23
<212> TYPE: DNA
<213> ORGANISM: Artificial Sequence
<220> FEATURE:
<223> OTHER INFORMATION: Synthetic Primer

<400> SEQUENCE: 6
agaatctaaa tctaaaagtc cag                                          23

<210> SEQ ID NO 7
<211> LENGTH: 19
<212> TYPE: DNA
<213> ORGANISM: Artificial Sequence
<220> FEATURE:
<223> OTHER INFORMATION: Synthetic Primer

<400> SEQUENCE: 7
cttcatttaa caacagaaa                                               19

<210> SEQ ID NO 8
<211> LENGTH: 23
<212> TYPE: DNA
<213> ORGANISM: Artificial Sequence
<220> FEATURE:
<223> OTHER INFORMATION: Synthetic Primer

<400> SEQUENCE: 8
ttgagcagcc atatcttctt cat                                          23

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9
atgcttcatt taacaacaga                                              20

<210> SEQ ID NO 10
<211> LENGTH: 25
<212> TYPE: DNA
<213> ORGANISM: Artificial Sequence
<220> FEATURE:
<223> OTHER INFORMATION: Synthetic Primer

<400> SEQUENCE: 10
ttgataagca tgcacagaaa taaag                                        25

<210> SEQ ID NO 11
<211> LENGTH: 23
<212> TYPE: DNA
<213> ORGANISM: Artificial Sequence
<220> FEATURE:
<223> OTHER INFORMATION: Synthetic Primer

<400> SEQUENCE: 11
ggaaatccat cacgtcctgc tat                                          23

<210> SEQ ID NO 12
<211> LENGTH: 23
<212> TYPE: DNA
<213> ORGANISM: Artificial Sequence

```
<220> FEATURE:
<223> OTHER INFORMATION: Synthetic Primer

<400> SEQUENCE: 12
agaatctaaa tctaaaagtc cag                                    23

<210> SEQ ID NO 13
<211> LENGTH: 19
<212> TYPE: DNA
<213> ORGANISM: Artificial Sequence
<220> FEATURE:
<223> OTHER INFORMATION: Synthetic Primer

<400> SEQUENCE: 13
cttcatttaa caacagaaa                                         19

<210> SEQ ID NO 14
<211> LENGTH: 24
<212> TYPE: DNA
<213> ORGANISM: Artificial Sequence
<220> FEATURE:
<223> OTHER INFORMATION: Synthetic Primer

<400> SEQUENCE: 14
aactggaacc actatactgt cact                                   24

<210> SEQ ID NO 15
<211> LENGTH: 25
<212> TYPE: DNA
<213> ORGANISM: Artificial Sequence
<220> FEATURE:
<223> OTHER INFORMATION: Synthetic Primer

<400> SEQUENCE: 15
gacagtatag tggttccagt tcttg                                  25

<210> SEQ ID NO 16
<211> LENGTH: 23
<212> TYPE: DNA
<213> ORGANISM: Artificial Sequence
<220> FEATURE:
<223> OTHER INFORMATION: Synthetic Primer

<400> SEQUENCE: 16
ttgagcagcc atatcttctt cat                                    23

<210> SEQ ID NO 17
<211> LENGTH: 31
<212> TYPE: DNA
<213> ORGANISM: Artificial Sequence
<220> FEATURE:
<223> OTHER INFORMATION: Synthetic Primer

<400> SEQUENCE: 17
caccactgaa gattctgttt ctgctccagc t                           31

<210> SEQ ID NO 18
<211> LENGTH: 27
<212> TYPE: DNA
<213> ORGANISM: Artificial Sequence
<220> FEATURE:
<223> OTHER INFORMATION: Synthetic Primer

<400> SEQUENCE: 18
agctggagca gaaacagaat cttcagt                                27
```

<210> SEQ ID NO 19
<211> LENGTH: 61
<212> TYPE: DNA
<213> ORGANISM: Artificial Sequence
<220> FEATURE:
<223> OTHER INFORMATION: Synthetic Primer

<400> SEQUENCE: 19
caccgctagt gtatctgaag gagatgcagt agtaaatgct gtaagccaag aaactcctgc    60
a                                                                    61

<210> SEQ ID NO 20
<211> LENGTH: 57
<212> TYPE: DNA
<213> ORGANISM: Artificial Sequence
<220> FEATURE:
<223> OTHER INFORMATION: Synthetic Primer

<400> SEQUENCE: 20
tgcaggagtt tcttggctta cagcatttac tactgcatct ccttcagata cactagc       57

<210> SEQ ID NO 21
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 21

Arg Asn Thr Thr Val Gly Val Phe Gly Leu Lys Gln Asn Trp Asp Gly
1               5                   10                  15

Ser Ala Ile Ser
            20

<210> SEQ ID NO 22
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 22

Thr Glu Asp Ser Val Ser Ala Pro Ala
1               5

<210> SEQ ID NO 23
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 23

Ala Ser Val Ser Glu Gly Asp Ala Val Val Asn Ala Val Ser Gln Glu
1               5                   10                  15

Thr Pro Ala

<210> SEQ ID NO 24
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 24

```
Glu Gly Asn Ala Ser Glu Pro Val Val Ser Gln Ala Ala Pro Val
1               5                   10                  15

Ser Glu Ser Gly Asp Ala Ala Asn Pro Val Ser Ser Glu Asn Ala
                20                  25                  30

Ser

<210> SEQ ID NO 25
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 25

Val Thr Ser Ser Pro Glu Gly Ser Val
1               5

<210> SEQ ID NO 26
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 26

Ser Ser Glu Val Thr Glu Ser Asn Gln Gly Ser Ser Ala Ser Val Val
1               5                   10                  15

Gly Asp Ala Gly Val Gln
                20

<210> SEQ ID NO 27
<211> LENGTH: 36
<212> TYPE: PRT
<213> ORGANISM: Artificial Sequence
<220> FEATURE:
<223> OTHER INFORMATION: Synthetic Peptide

<400> SEQUENCE: 27

Lys Glu Glu Ser Thr Pro Glu Val Lys Ala Glu Asp Leu Gln Pro Ala
1               5                   10                  15

Val Asp Gly Ser Val Glu His Ser Ser Ser Val Gly Glu Lys Val
                20                  25                  30

Ser Glu Thr Ser
        35

<210> SEQ ID NO 28
<211> LENGTH: 80
<212> TYPE: PRT
<213> ORGANISM: Artificial Sequence
<220> FEATURE:
<223> OTHER INFORMATION: Synthetic Peptide

<400> SEQUENCE: 28

Glu Asp Glu Ile Val Ser Gln Pro Ser Ser Glu Pro Phe Val Ala Glu
1               5                   10                  15

Ser Glu Val Ser Lys Val Glu Gln Glu Glu Thr Asn Pro Glu Val Leu
                20                  25                  30

Ile Lys Asp Leu Gln Asp Val Ala Ser His Glu Ser Gly Val Ser Asp
                35                  40                  45

Gln Pro Ala Gln Val Val Thr Glu Arg Glu Ser Glu Ile Glu Ser His
        50                  55                  60
```

```
Gln Gly Glu Thr Glu Lys Glu Ser Gly Ile Thr Glu Ser His Gln Lys
 65                  70                  75                  80
```

```
<210> SEQ ID NO 29
<211> LENGTH: 625
<212> TYPE: PRT
<213> ORGANISM: Ehrlichia ruminantium

<400> SEQUENCE: 29

Met Val His Ser Thr Ala Glu Asp Cys Met Leu His Leu Thr Thr Arg
  1               5                  10                  15

Ile Asp Asn Ile Asp Phe Gly Asn Asp Leu Asn Ile Tyr Ser Asn Asn
                 20                  25                  30

Gln Phe Ser Val Ser Asn Gly Asp Ile Thr Met Glu Ile Gly Tyr His
             35                  40                  45

Pro His Glu His Glu Gly His Glu Glu Gly His Glu Asn His His
         50                  55                  60

Gly Glu Tyr His Val Met Phe Thr Ser Asn Gly His Val Leu Ser Asp
 65                  70                  75                  80

Phe His Gly Val Thr Gly Lys His Ile Ala Leu Asp Val Leu Asn His
                 85                  90                  95

Ser Leu Gln Ala Ser Phe Val Val Asn Leu Met Glu Pro Phe Ser Glu
            100                 105                 110

Phe Leu Gln Gln Gly Ser Asn Phe Ser Leu Asn Leu His Pro Leu Asn
        115                 120                 125

Val Cys Tyr Asp Lys Val Ile Ser Gly Val Asp Thr Thr Val Thr Ser
130                 135                 140

Ser Pro Glu Gly Ser Val Val Thr Ser Ser Pro Glu Gly Ala Ala Val
145                 150                 155                 160

Thr Ser Ser Pro Glu Gly Ser Val Val Thr Ser Ser Pro Glu Gly Ala
                165                 170                 175

Ala Val Thr Ser Ser Pro Glu Gly Ser Ala Val Thr Ser Ser Pro Glu
            180                 185                 190

Gly Ala Ala Val Thr Ser Ser Pro Glu Gly Ser Val Val Thr Ser Ser
        195                 200                 205

Pro Glu Gly Ala Ala Val Thr Ser Ser Pro Glu Gly Ser Val Val Thr
210                 215                 220

Ser Ser Pro Glu Gly Ala Ala Val Thr Ser Ser Pro Glu Gly Ala Val
225                 230                 235                 240

Val Thr Ser Ser Pro Glu Gly Ala Ala Val Thr Ser Ser Pro Glu Gly
                245                 250                 255

Ser Val Val Thr Ser Ser Pro Lys Gly Ala Ala Val Thr Ser Ser Pro
            260                 265                 270

Lys Gly Ser Val Val Thr Ser Ser Pro Lys Gly Ala Ala Val Thr Ser
        275                 280                 285

Ser Pro Glu Gly Ser Val Val Thr Ser Ser Pro Lys Gly Ser Ala Val
        290                 295                 300

Thr Ser Ser Pro Lys Gly Ser Val Val Thr Ser Ser Pro Lys Gly Ser
305                 310                 315                 320

Ala Val Thr Ser Ser Pro Glu Gly Ser Val Val Thr Ser Ser Pro Glu
                325                 330                 335

Gly Ser Ala Val Thr Ser Ser Pro Lys Gly Ser Val Val Thr Ser Ser
            340                 345                 350

Pro Glu Gly Ser Val Val Thr Ser Ser Pro Glu Gly Ser Val Val Thr
        355                 360                 365
```

Ser Ser Pro Glu Gly Ala Ala Val Thr Ser Ser Pro Glu Gly Ser Val
    370                 375                 380

Val Thr Ser Ser Pro Glu Gly Ala Ala Val Thr Ser Ser Pro Glu Gly
385                 390                 395                 400

Ser Val Val Thr Ser Ser Pro Glu Gly Ser Val Val Thr Ser Ser Pro
            405                 410                 415

Glu Gly Ala Ala Val Thr Ser Ser Pro Glu Gly Ala Ala Val Thr Ser
        420                 425                 430

Ser Pro Glu Gly Ala Ala Val Thr Ser Ser Pro Glu Gly Ser Val Val
            435                 440                 445

Thr Ser Ser Pro Glu Gly Ala Ala Val Thr Ser Pro Glu Gly Ser
    450                 455                 460

Val Val Thr Ser Ser Pro Glu Gly Ala Ala Val Thr Ser Ser Pro Glu
465                 470                 475                 480

Gly Ala Ala Val Thr Ser Ser Pro Gly Ser Val Val Thr Ser Ser
            485                 490                 495

Pro Glu Gly Ala Ala Ile Thr Ser Ser Pro Glu Gly Ala Ala Ile Thr
            500                 505                 510

Ser Ser Pro Glu Gly Ser Val Val Thr Ser Ser Pro Glu Gly Ser Val
        515                 520                 525

Val Thr Ser Ser Pro Glu Gly Ala Ala Val Thr Ser Ser Pro Glu Gly
    530                 535                 540

Ser Val Val Thr Ser Ser Pro Glu Gly Ala Ala Val Thr Ser Ser Pro
545                 550                 555                 560

Glu Gly Ser Val Val Thr Ser Ser Pro Glu Gly Ser Val Val Thr Ser
            565                 570                 575

Ser Pro Glu Gly Ser Val Val Thr Ser Ser Pro Glu Gly Ala Ala Val
        580                 585                 590

Thr Ser Ser Pro Glu Gly Ala Ala Val Thr Ser Ser Pro Glu Val Ala
    595                 600                 605

Lys Gly Phe Thr Phe Gly Gly Arg Ser Gly Glu Arg Val Phe Thr Gly
    610                 615                 620

Ile
625

<210> SEQ ID NO 30
<211> LENGTH: 530
<212> TYPE: PRT
<213> ORGANISM: Ehrlichia ruminantium

<400> SEQUENCE: 30

Met Val His Ser Thr Ala Glu Asp Cys Met Leu His Leu Thr Thr Arg
1               5                   10                  15

Ile Asp Asn Ile Asp Phe Gly Asn Asp Leu Ser Ile Tyr Ser Asn Asn
            20                  25                  30

Gln Phe Ser Val Ser Asn Gly Asp Ile Thr Met Glu Ile Gly Tyr His
        35                  40                  45

Pro His Glu His Glu Glu Gly His Glu Gly His Glu Asp His His
    50                  55                  60

Gly Glu Tyr His Val Met Phe Thr Ser Asn Gly His Val Leu Ser Asp
65                  70                  75                  80

Phe His Gly Val Thr Gly Lys His Ile Thr Leu Asp Val Leu Asn His
            85                  90                  95

Ser Leu Gln Ala Ser Phe Val Val Asn Leu Met Glu Pro Phe Ser Glu

-continued

```
                100                 105                 110
Phe Leu Gln Gln Gly Ser Asn Phe Ser Leu Asn Leu His Pro Leu Ile
            115                 120                 125
Glu Asp Cys Gly Leu Asp Gly His Asp His Val His His Val Gly Val
130                 135                 140
Leu Gly Ser Asp Ile Val Ser Ala Ala Asn Thr Ser Ser Glu Val Thr
145                 150                 155                 160
Glu Ser Asn Gln Gly Ser Ser Ala Ser Val Val Gly Asp Ala Gly Val
                165                 170                 175
Gln Ser Ser Glu Val Thr Glu Ser Asn Gln Gly Ser Ser Ala Ser Val
            180                 185                 190
Val Gly Asp Ala Gly Val Gln Ser Ser Glu Val Thr Glu Ser Asn Gln
        195                 200                 205
Gly Ser Ser Ala Ser Val Val Gly Asp Ala Gly Val Gln Ser Ser Glu
    210                 215                 220
Val Thr Glu Ser Asn Gln Gly Ser Ser Ala Ser Val Val Gly Asp Ala
225                 230                 235                 240
Gly Val Gln Ser Ser Glu Val Thr Glu Ser Asn Gln Gly Ser Ser Ala
                245                 250                 255
Ser Val Val Gly Asp Ala Gly Val Gln Ser Ser Glu Val Thr Glu Ser
            260                 265                 270
Asn Gln Gly Ser Ser Ala Ser Val Val Gly Asp Ala Gly Val Gln Ser
        275                 280                 285
Ser Glu Val Thr Glu Ser Asn Gln Gly Ser Ser Ala Ser Val Val Gly
    290                 295                 300
Asp Val Gly Val Gln Ser Ser Glu Val Thr Glu Ser Asn Gln Gly Ser
305                 310                 315                 320
Ser Ala Ser Val Val Gly Asp Ala Gly Val Gln Ser Ser Glu Val Thr
                325                 330                 335
Glu Ser Asn Gln Gly Ser Ser Ala Ser Val Val Gly Asp Ala Gly Val
            340                 345                 350
Gln Ser Ser Glu Val Thr Glu Ser Asn Gln Gly Ser Ser Ala Ser Val
        355                 360                 365
Val Gly Asp Ala Gly Val Gln Ser Ser Glu Val Thr Glu Ser Asn Gln
    370                 375                 380
Gly Ser Ser Ala Ser Val Val Gly Asp Val Gly Val Gln Ser Ser Glu
385                 390                 395                 400
Val Thr Glu Ser Asn Gln Gly Ser Ser Ala Ser Val Val Gly Asp Ala
                405                 410                 415
Gly Val Gln Ser Ser Glu Val Thr Glu Ser Asn Gln Gly Ser Ser Ala
            420                 425                 430
Ser Val Val Gly Asp Ala Gly Val Gln Ser Ser Glu Val Thr Glu Ser
        435                 440                 445
Asn Gln Gly Ser Ser Ala Ser Val Val Gly Asp Ala Gly Val Gln Ser
    450                 455                 460
Ser Glu Val Thr Glu Ser Asn Gln Gly Ser Ser Ala Ser Val Val Gly
465                 470                 475                 480
Asp Ala Gly Val Gln Ser Ser Glu Val Thr Glu Ser Asn Gln Gly Ser
                485                 490                 495
Ser Ala Ser Val Val Gly Asp Ala Gly Val Gln Ser Ser Glu Val Thr
            500                 505                 510
Glu Ser Asn Gln Gly Ser Ser Ala Ser Val Val Gly Asp Ala Gly Ile
        515                 520                 525
```

Lys Ile
    530

<210> SEQ ID NO 31
<211> LENGTH: 351
<212> TYPE: PRT
<213> ORGANISM: Cowdria ruminantium

<400> SEQUENCE: 31

Met Val His Ser Thr Ala Glu Asp Cys Met Leu His Leu Thr Thr Arg
1               5                   10                  15

Ile Asp Asn Ile Asp Phe Gly Asn Asp Leu Ser Ile Tyr Ser Asn Asn
            20                  25                  30

Gln Phe Ser Val Ser Asn Gly Asp Ile Thr Met Glu Ile Gly Tyr His
        35                  40                  45

Pro His Glu His Glu Gly His Glu Asn His His Gly Glu Tyr His
    50                  55                  60

Val Met Phe Thr Ser Asn Gly His Val Leu Ser Asp Phe His Gly Val
65                  70                  75                  80

Thr Gly Lys His Ile Ala Leu Asp Val Leu Asn His Ser Leu Gln Ala
                85                  90                  95

Ser Phe Val Val Asn Leu Met Glu Pro Phe Ser Glu Phe Leu Gln Gln
            100                 105                 110

Gly Ser Asn Phe Ser Leu Asn Leu His Pro Leu Asn Val Cys Tyr Asp
        115                 120                 125

Lys Val Ile Ser Gly Val Asp Thr Thr Val Thr Asn Ser Pro Glu Gly
130                 135                 140

Ala Ala Val Thr Ser Ser Pro Glu Gly Ser Val Val Thr Ser Ser Pro
145                 150                 155                 160

Glu Gly Ser Val Val Thr Ser Ser Pro Glu Gly Ser Val Val Thr Ser
                165                 170                 175

Ser Pro Glu Gly Ser Val Val Thr Ser Ser Pro Glu Gly Ser Val Val
            180                 185                 190

Thr Ser Ser Pro Glu Gly Ser Val Val Thr Ser Ser Pro Glu Gly Ser
        195                 200                 205

Val Val Thr Ser Ser Pro Glu Gly Ser Val Val Thr Ser Ser Pro Glu
    210                 215                 220

Gly Ser Val Val Thr Ser Ser Pro Glu Gly Ser Val Val Thr Ser Ser
225                 230                 235                 240

Pro Glu Gly Ser Val Val Thr Ser Ser Pro Glu Gly Ser Val Val Thr
                245                 250                 255

Ser Ser Pro Glu Gly Ser Val Val Thr Ser Ser Pro Glu Gly Ser Val
            260                 265                 270

Val Thr Ser Ser Pro Glu Gly Ser Val Val Thr Ser Ser Pro Glu Gly
        275                 280                 285

Ser Val Val Thr Ser Ser Pro Glu Gly Ser Val Val Thr Ser Ser Pro
    290                 295                 300

Glu Gly Ser Val Val Thr Ser Ser Pro Glu Gly Ser Val Val Thr Ser
305                 310                 315                 320

Ser Pro Glu Gly Ser Val Val Thr Ser Ser Pro Glu Val Ala Lys Gly
                325                 330                 335

Phe Thr Phe Gly Gly Arg Ser Gly Glu Arg Val Phe Thr Gly Ile
            340                 345                 350

<210> SEQ ID NO 32
<211> LENGTH: 840
<212> TYPE: DNA
<213> ORGANISM: Ehrlichia canis

<400> SEQUENCE: 32

| | | | | | |
|---|---|---|---|---|---|
| atgctattta | tactaatggg | ttattgtatg | cttcatttaa | caacagaaat | cacaaacatt | 60 |
| gattttgctc | atgattttca | tatacatcaa | ggtgaaagat | ttggtgtttc | aagtggtgat | 120 |
| ctagaacttg | atattgaaaa | ccatcctgga | catggttatc | atattttatt | taagaacaat | 180 |
| ggccatgtaa | tatcagattt | acatggtgct | aaagctgaag | actttaactt | tgatatgaag | 240 |
| gatcatagtt | tgaatgtttc | tttcttaatt | gatccaatgg | ctccttttca | tgagttagat | 300 |
| gttaataacc | atcctaactt | ctttatttct | gtgcatgctt | atcaagatgg | ttgtgataat | 360 |
| tgtgtacatg | gaaatccatc | acgtcctgct | atagtaaatc | aagctcaagt | tttattacca | 420 |
| agtggagtta | ctgaagattc | tgtttctgct | ccagctactg | aagattctgt | ttctgctcca | 480 |
| gctactgaag | attctgtttc | tgctccagct | actgaagatt | ctgtttctgc | tccagctact | 540 |
| gaagattctg | tttctgctcc | agctactgaa | gattctgttt | ctgctccagc | tactgaagat | 600 |
| tctgtttctg | ctccagctac | tgaagattct | gtttctgctc | cagctactga | agattctgtt | 660 |
| tctgctccag | ctactgaaga | ttctgtttct | gctccagcta | ctgaagattc | tgtttctgct | 720 |
| ccagctactg | aagattctgt | ttctgctcca | gctactgcag | caacaggttc | aacaacatca | 780 |
| tataatcaca | acactggact | tttagattta | gattctgata | ttcttaacat | gttgtactaa | 840 |

<210> SEQ ID NO 33
<211> LENGTH: 657
<212> TYPE: DNA
<213> ORGANISM: Ehrlichia canis

<400> SEQUENCE: 33

| | | | | | |
|---|---|---|---|---|---|
| atgctattta | tactaatggg | ttattgtatg | cttcatttaa | caacagaaat | cacaaacatt | 60 |
| gattttgctc | atgattttca | tatacatcaa | ggtgaaagat | ttggtgtttc | aagtggtgat | 120 |
| ctagaacttg | atattgaaaa | ccatcctgga | catggttatc | atattttatt | taagaacaat | 180 |
| ggccatgtaa | tatcagattt | acatggtgct | aaagctgaag | actttaactt | tgatatgaag | 240 |
| gatcatagtt | tgaatgtttc | tttcttaatt | gatccaatgg | ctccttttca | tgagttagat | 300 |
| gttaataacc | atcctaactt | ctttatttct | gtgcatgctt | atcaagatgg | ttgtgataat | 360 |
| tgtgtacatg | gaaatccatc | acgtcctgct | atagtaaatc | aagctcaagt | tttattacca | 420 |
| agtggagtta | ctgaagattc | tgtttctgct | ccagctactg | aagattctgt | ttctgctcca | 480 |
| gctactgaag | attctgtttc | tgctccagct | actgaagatt | ctgtttctgc | tccagctact | 540 |
| gaagattctg | tttctgctcc | agctactgca | gcaacaggtt | caacaacatc | atataatcac | 600 |
| aacactggac | ttgagttttt | agatttagat | tctgatattc | ttaacatgtt | gtactaa | 657 |

<210> SEQ ID NO 34
<211> LENGTH: 948
<212> TYPE: DNA
<213> ORGANISM: Ehrlichia canis

<400> SEQUENCE: 34

| | | | | | |
|---|---|---|---|---|---|
| atgctattta | tactaatggg | ttattgtatg | cttcatttaa | caacagaaat | cacaaacatt | 60 |
| gattttgctc | atgattttca | tatacatcaa | ggtgaaagat | ttggtgtttc | aagtggtgat | 120 |
| ctagaacttg | atattgaaaa | ccatcctgga | catggttatc | atattttatt | taagaacaat | 180 |

```
ggccatgtaa tatcagattt acatggtgct aaagctgaag actttaactt tgatatgaag      240
gatcatagtt tgaatgtttc tttcttaatt gatccaatgg ctccttttca tgagttagat      300
gttaataacc atcctaactt ctttatttct gtgcatgctt atcaagatgg ttgtgataat      360
tgtgtacatg gaaatccatc acgtcctgct atagtaaatc aagctcaagt tttattacca      420
agtggagtta ctgaagattc tgtttctgct ccagctactg aagattctgt ttctgctcca      480
gctactgaag attctgtttc tgctccagct actgaagatt ctgttctgc tccagctact       540 gaagattctg tttctgctcc agctactgaa gattctgttt ctgctccagc tactgaagat      600
tctgtttctg ctccagctac tgaagattct gtttctgctc agctactga agattctgtt       660 tctgctccag ctactgaaga ttctgtttct gctccagcta ctgaagattc tgtttctgct      720
ccagctactg aagattctgt ttctgctcca gctactgaag attctgtttc tgctccagct      780
actgaagatt ctgtttctgc tccagctact gaagattctg tttctgctcc agctactgaa      840
gattctgttt ctgctccagc tactgcagca acaggttcaa caacatcata taatcacaac      900
actggacttt tagatttaga ttctgatatt cttaacatgt tgtactaa                  948

<210> SEQ ID NO 35
<211> LENGTH: 951
<212> TYPE: DNA
<213> ORGANISM: Ehrlichia chaffeensis

<400> SEQUENCE: 35
atgcttcatt taacaacaga aattaatgat attgatttct ctaataattt aaatatttat      60
agtgggaata gatttgttgt tacaagtggt gacatgcagg ttgatgttgg aagtgaacct      120
gatcatggtt atcatatttt atttaaaaac aatggtcatg ttatatcaga ttttcgtggt      180
gtacaagctg aaaactttgt atttgatata aaaaatcaca atttaagagc ttctttctta      240
gttgatccta tggcaccttt tacagaatta gataacagtc agcatccaca cttcgtcgtt      300
aacatgcaca ctgcaaatga atgtggttct gattgtgttc atcacaatga acatgatcat      360
gatgcacacg aagaggtgc ggctagctct gtagctgaag gtgtaggttc tgcaataagt       420
caaatcttat ctttaagtga cagtatagtg gttccagttc ttgaaggaaa tgctagtgta      480
tctgaaggag atgcagtagt aaatgctgta agccaagaag ctcctgcagc tagtgtatct      540
gaaggagatg cagtagtaaa tgctgtaagc caagaaactc ctgcagctag tgtatctgaa      600
ggagatgcag tagtaaatgc tgtaagccaa gaaactcctg cagctagtgt atctgaagga      660
gatgcagtag taaatgctgt aagccaagaa actcctgcag ctagtgtatc tgaaggagat      720
gcagtagtaa atgctgtaag ccaagaaact cctgcagcta gtgtatctga aggagatgca      780
gtagtaaatg ctgtaagcca agaaactcct gcagctagtg tatctgaagg agatgcagta      840
gtaaatgctg taagccaaga aactcctgca actcaaccac aatctagaga ttctttgtta      900
aatgaagaag atatggctgc tcaatttggt aatagatact tttatttcta a               951

<210> SEQ ID NO 36
<211> LENGTH: 987
<212> TYPE: DNA
<213> ORGANISM: Ehrlichia chaffeensis

<400> SEQUENCE: 36
atgcttcatt taacaacaga aattaatgat attgatttct ctaataattt aaatatttat      60
agtgggaata gatttgttgt tacaagtggt gacatgcagg ttgatgttgg aagtgaacct      120
gatcatggtt atcatatttt atttaaaaac aatggtcatg ttatatcaga ttttcgtggt      180
```

-continued

```
gtacaagctg aaaactttgt atttgatata aaaaatcaca atttaagagc ttctttctta    240
gttgatccta tggcaccttt tacagaatta gataacagtc agcatccaca cttcgtcgtt    300
aacatgcaca ctgcaaatga atgtggttct gattgtgttc atcacaatga acatgatcat    360
gatgcacacg gaagaggtgc ggctagctct gtagctgaag gtgtaggttc tgcaataagt    420
caaatcttat ctttaagtga cagtatagtg gttccagttc ttgaaggaaa tgctagtgaa    480
cctgttgtaa gccaagaagc agctcctgta tctgagagtg gagatgcagc aaatccagta    540
tcttcaagtg aaaatgcttc tgaaggaaat gctagtgaac tgttgtaaa ccaagaagca     600
gctcctgtat ctgagagtgg agatacagca aatccagtat cttcaagtga aaatgcttct    660
gaaggaaatg ctagtgaacc tgttgtaagc caagaagcag ctcctgtatc tgagagtgga    720
gatgcagcaa atccagtatc ttcaagtgaa aatgcttctg aaggaaatgc tagtgaacct    780
gttgtaagcc aagaagcagc tcctgtatct gagagtggag atgcagcaaa tccagtatct    840
tcaagtgaaa atgcttctga aggaaatgct agtgaacctg ttgtaaaacca agaaacagct   900
cctgcgattc aaccacaatc tagaaattct ttgttaagtg aagaagatat aactgctcag    960
tttggtaata aatacttta tttctaa                                        987
```

<210> SEQ ID NO 37
<211> LENGTH: 279
<212> TYPE: PRT
<213> ORGANISM: Ehrlichia canis

<400> SEQUENCE: 37

```
Met Leu Phe Ile Leu Met Gly Tyr Cys Met Leu His Leu Thr Thr Glu
1               5                   10                  15

Ile Thr Asn Ile Asp Phe Ala His Asp Phe His Ile His Gln Gly Glu
            20                  25                  30

Arg Phe Gly Val Ser Ser Gly Asp Leu Glu Leu Asp Ile Glu Asn His
        35                  40                  45

Pro Gly His Gly Tyr His Ile Leu Phe Lys Asn Asn Gly His Val Ile
    50                  55                  60

Ser Asp Leu His Gly Ala Lys Ala Glu Asp Phe Asn Phe Asp Met Lys
65                  70                  75                  80

Asp His Ser Leu Asn Val Ser Phe Leu Ile Asp Pro Met Ala Pro Phe
                85                  90                  95

His Glu Leu Asp Val Asn Asn His Pro Asn Phe Phe Ile Ser Val His
            100                 105                 110

Ala Tyr Gln Asp Gly Cys Asp Asn Cys Val His Gly Asn Pro Ser Arg
        115                 120                 125

Pro Ala Ile Val Asn Gln Ala Gln Val Leu Leu Pro Ser Gly Val Thr
    130                 135                 140

Glu Asp Ser Val Ser Ala Pro Ala Thr Glu Asp Ser Val Ser Ala Pro
145                 150                 155                 160

Ala Thr Glu Asp Ser Val Ser Ala Pro Ala Thr Glu Asp Ser Val Ser
                165                 170                 175

Ala Pro Ala Thr Glu Asp Ser Val Ser Ala Pro Ala Thr Glu Asp Ser
            180                 185                 190

Val Ser Ala Pro Ala Thr Glu Asp Ser Val Ser Ala Pro Ala Thr Glu
        195                 200                 205

Asp Ser Val Ser Ala Pro Ala Thr Glu Asp Ser Val Ser Ala Pro Ala
    210                 215                 220
```

```
Thr Glu Asp Ser Val Ser Ala Pro Ala Thr Glu Asp Ser Val Ser Ala
225                 230                 235                 240

Pro Ala Thr Glu Asp Ser Val Ser Ala Pro Ala Thr Ala Ala Thr Gly
            245                 250                 255

Ser Thr Thr Ser Tyr Asn His Asn Thr Gly Leu Leu Asp Leu Asp Ser
        260                 265                 270

Asp Ile Leu Asn Met Leu Tyr
        275

<210> SEQ ID NO 38
<211> LENGTH: 218
<212> TYPE: PRT
<213> ORGANISM: Ehrlichia canis

<400> SEQUENCE: 38

Met Leu Phe Ile Leu Met Gly Tyr Cys Met Leu His Leu Thr Thr Glu
1               5                   10                  15

Ile Thr Asn Ile Asp Phe Ala His Asp Phe His Ile His Gln Gly Glu
            20                  25                  30

Arg Phe Gly Val Ser Ser Gly Asp Leu Glu Leu Asp Ile Glu Asn His
        35                  40                  45

Pro Gly His Gly Tyr His Ile Leu Phe Lys Asn Asn Gly His Val Ile
    50                  55                  60

Ser Asp Leu His Gly Ala Lys Ala Glu Asp Phe Asn Phe Asp Met Lys
65                  70                  75                  80

Asp His Ser Leu Asn Val Ser Phe Leu Ile Asp Pro Met Ala Pro Phe
                85                  90                  95

His Glu Leu Asp Val Asn Asn His Pro Asn Phe Phe Ile Ser Val His
            100                 105                 110

Ala Tyr Gln Asp Gly Cys Asp Asn Cys Val His Gly Asn Pro Ser Arg
        115                 120                 125

Pro Ala Ile Val Asn Gln Ala Gln Val Leu Leu Pro Ser Gly Val Thr
    130                 135                 140

Glu Asp Ser Val Ser Ala Pro Ala Thr Glu Asp Ser Val Ser Ala Pro
145                 150                 155                 160

Ala Thr Glu Asp Ser Val Ser Ala Pro Ala Thr Glu Asp Ser Val Ser
                165                 170                 175

Ala Pro Ala Thr Glu Asp Ser Val Ser Ala Pro Ala Thr Ala Ala Thr
            180                 185                 190

Gly Ser Thr Thr Ser Tyr Asn His Asn Thr Gly Leu Glu Phe Leu Asp
        195                 200                 205

Leu Asp Ser Asp Ile Leu Asn Met Leu Tyr
    210                 215

<210> SEQ ID NO 39
<211> LENGTH: 315
<212> TYPE: PRT
<213> ORGANISM: Ehrlichia canis

<400> SEQUENCE: 39

Met Leu Phe Ile Leu Met

Pro Gly His Gly Tyr His Ile Leu Phe Lys Asn Asn Gly His Val Ile
            50                  55                  60

Ser Asp Leu His Gly Ala Lys Ala Glu Asp Phe Asn Phe Asp Met Lys
 65                  70                  75                  80

Asp His Ser Leu Asn Val Ser Phe Leu Ile Asp Pro Met Ala Pro Phe
                85                  90                  95

His Glu Leu Asp Val Asn Asn His Pro Asn Phe Phe Ile Ser Val His
            100                 105                 110

Ala Tyr Gln Asp Gly Cys Asp Asn Cys Val His Gly Asn Pro Ser Arg
            115                 120                 125

Pro Ala Ile Val Asn Gln Ala Gln Val Leu Leu Pro Ser Gly Val Thr
130                 135                 140

Glu Asp Ser Val Ser Ala Pro Ala Thr Glu Asp Ser Val Ser Ala Pro
145                 150                 155                 160

Ala Thr Glu Asp Ser Val Ser Ala Pro Ala Thr Glu Asp Ser Val Ser
                165                 170                 175

Ala Pro Ala Thr Glu Asp Ser Val Ser Ala Pro Ala Thr Glu Asp Ser
            180                 185                 190

Val Ser Ala Pro Ala Thr Glu Asp Ser Val Ser Ala Pro Ala Thr Glu
            195                 200                 205

Asp Ser Val Ser Ala Pro Ala Thr Glu Asp Ser Val Ser Ala Pro Ala
            210                 215                 220

Thr Glu Asp Ser Val Ser Ala Pro Ala Thr Glu Asp Ser Val Ser Ala
225                 230                 235                 240

Pro Ala Thr Glu Asp Ser Val Ser Ala Pro Ala Thr Glu Asp Ser Val
                245                 250                 255

Ser Ala Pro Ala Thr Glu Asp Ser Val Ser Ala Pro Ala Thr Glu Asp
            260                 265                 270

Ser Val Ser Ala Pro Ala Thr Glu Asp Ser Val Ser Ala Pro Ala Thr
            275                 280                 285

Ala Ala Thr Gly Ser Thr Thr Ser Tyr Asn His Asn Thr Gly Leu Leu
            290                 295                 300

Asp Leu Asp Ser Asp Ile Leu Asn Met Leu Tyr
305                 310                 315

<210> SEQ ID NO 40
<211> LENGTH: 316
<212> TYPE: PRT
<213> ORGANISM: Ehrlichia chaffeensis

<400> SEQUENCE: 40

Met Leu His Leu Thr Thr Glu Ile Asn Asp Ile Asp Phe Ser Asn Asn
1               5                   10                  15

Leu As

Val His His Asn Glu His Asp His Asp Ala His Gly Arg Gly Ala Ala
        115                 120                 125

Ser Ser Val Ala Glu Gly Val Gly Ser Ala Ile Ser Gln Ile Leu Ser
    130                 135                 140

Leu Ser Asp Ser Ile Val Val Pro Val Leu Glu Gly Asn Ala Ser Val
145                 150                 155                 160

Ser Glu Gly Asp Ala Val Val Asn Ala Val Ser Gln Glu Ala Pro Ala
                165                 170                 175

Ala Ser Val Ser Glu Gly Asp Ala Val Val Asn Ala Val Ser Gln Glu
            180                 185                 190

Thr Pro Ala Ala Ser Val Ser Glu Gly Asp Ala Val Val Asn Ala Val
        195                 200                 205

Ser Gln Glu Thr Pro Ala Ala Ser Val Ser Glu Gly Asp Ala Val Val
    210                 215                 220

Asn Ala Val Ser Gln Glu Thr Pro Ala Ala Ser Val Ser Glu Gly Asp
225                 230                 235                 240

Ala Val Val Asn Ala Val Ser Gln Glu Thr Pro Ala Ala Ser Val Ser
                245                 250                 255

Glu Gly Asp Ala Val Val Asn Ala Val Ser Gln Glu Thr Pro Ala Ala
            260                 265                 270

Ser Val Ser Glu Gly Asp Ala Val Val Asn Ala Val Ser Gln Glu Thr
        275                 280                 285

Pro Ala Thr Gln Pro Gln Ser Arg Asp Ser Leu Leu Asn Glu Glu Asp
    290                 295                 300

Met Ala Ala Gln Phe Gly Asn Arg Tyr Phe Tyr Phe
305                 310                 315

<210> SEQ ID NO 41
<211> LENGTH: 328
<212> TYPE: PRT
<213> ORGANISM: Ehrlichia chaffeensis

<400> SEQUENCE: 41

Met Leu His Leu Thr Thr Glu Ile Asn Asp Ile Asp Phe Ser Asn Asn
1               5                   10                  15

Leu Asn Ile Tyr Ser Gly Asn Arg Phe Val Val Thr Ser Gly Asp Met
            20                  25                  30

Gln Val Asp Val Gly Ser Glu Pro Asp His Gly Tyr His Ile Leu Phe
        35                  40                  45

Lys Asn Asn Gly His Val Ile Ser Asp Phe His Gly Val Gln Ala Glu
    50                  55                  60

Asn Phe Val Phe Asp Ile Lys Asn His Asn Leu Arg Ala Ser Phe Leu
65                  70                  75                  80

Val Asp Pro Met Ala Pro Phe Thr Glu Leu Asp Asn Ser Gln His Pro
                85                  90                  95

His Phe Val Val Asn Met His Thr Ala Asn Glu Cys Gly Ser Asp Cys
            100                 105                 110

Val His His Asn Glu His Asp His Asp Ala His Gly Arg Gly Ala Ala
        115                 120                 125

Ser Ser Val Ala Glu Gly Val Gly Ser Ala Ile Ser Gln Ile Leu Ser
    130                 135                 140

Leu Ser Asp Ser Ile Val Val Pro Val Leu Glu Gly Asn Ala Ser Glu
145                 150                 155                 160

Pro Val Val Ser Gln Glu Ala Ala Pro Val Ser Glu Ser Gly Asp Ala

```
                165                 170                 175
Ala Asn Pro Val Ser Ser Glu Asn Ala Ser Glu Gly Asn Ala Ser
            180                 185                 190

Glu Pro Val Val Asn Gln Glu Ala Ala Pro Val Ser Glu Ser Gly Asp
        195                 200                 205

Thr Ala Asn Pro Val Ser Ser Ser Glu Asn Ala Ser Glu Gly Asn Ala
        210                 215                 220

Ser Glu Pro Val Val Ser Gln Glu Ala Ala Pro Val Ser Glu Ser Gly
225                 230                 235                 240

Asp Ala Ala Asn Pro Val Ser Ser Glu Asn Ala Ser Glu Gly Asn
                245                 250                 255

Ala Ser Glu Pro Val Val Ser Gln Glu Ala Ala Pro Val Ser Glu Ser
            260                 265                 270

Gly Asp Ala Ala Asn Pro Val Ser Ser Glu Asn Ala Ser Glu Gly
                275                 280                 285

Asn Ala Ser Glu Pro Val Val Asn Gln Glu Thr Ala Pro Ala Ile Gln
            290                 295                 300

Pro Gln Ser Arg Asn Ser Leu Leu Ser Glu Glu Asp Ile Thr Ala Gln
305                 310                 315                 320

Phe Gly Asn Lys Tyr Phe Tyr Phe
                325

<210> SEQ ID NO 42
<211> LENGTH: 1056
<212> TYPE: DNA
<213> ORGANISM: Ehrlichia ruminantium

<400> SEQUENCE: 42
atggttcatt caacagcaga agattgtatg cttcatttaa caacaagaat tgacaatatt     60
gattttggaa atgatttaag tatctatagt aataatcaat tctctgtttc aaatggtgat    120
attacaatgg agattggcta tcatcctcat gagcatgaag aaggtcatga aaatcatcat    180
ggcgaatatc atgttatgtt tacgagtaat ggtcacgtac tttcagattt tcatggtgtt    240
actggtaaac atattgcact tgatgtatta aaccacagct acaagcttc tttttgtagta    300
aatttaatgg aaccttttc agagttttta caacaaggtt ctaatttttc tcttaatctt    360
catccattaa atgtgtgcta tgataaggtg atctcaggtg ttgatacaac tgtaacaaat    420
agcccagaag gagcagctgt aacaagtagc ccagaaggat cagttgtaac aagtagccca    480
gaaggatcag ttgtaacaag tagcccagaa ggatcagttg taacaagtag cccagaagga    540
tcagttgtaa caagtagccc agaaggatca gttgtaacaa gtagcccaga aggatcagtt    600
gtaacaagta gcccagaagg atcagttgta acaagtagcc cagaaggatc agttgtaaca    660
agtagcccag aaggatcagt tgtaacaagt agcccagaag gatcagttgt aacaagtagc    720
ccagaaggat cagttgtaac aagtagccca gaaggatcag ttgtaacaag tagcccagaa    780
ggatcagttg taacaagtag cccagaagga tcagttgtaa caagtagccc agaaggatca    840
gttgtaacaa gtagcccaga aggatcagtt gtaacaagta gcccagaagg atcagttgta    900
acaagtagcc cagaaggatc agttgtaaca agtagcccag aaggatcagt tgtaacaagt    960
agcccagaag gatcagttgt aacaagtagc ccagaagtag caaaaggatt tacatttggt   1020
ggtcgtagtg gtgaaagagt atttactggc atctaa                             1056

<210> SEQ ID NO 43
<211> LENGTH: 1986
```

<212> TYPE: DNA
<213> ORGANISM: Ehrlichia ruminantium

<400> SEQUENCE: 43

```
atggttcatt caacagcaga agattgtatg cttcatttaa caacaagaat tgacaatatt      60
gattttggaa atgatttaaa tatctatagt aataatcaat tctctgtttc aaatggtgat     120
attacaatgg agattggcta tcatcctcat gagcatgaag aaggtcatga gagggtcat     180
gaaaatcatc atggcgaata tcatgttatg tttacgagta atggtcacgt actttcagat    240
tttcatggtg ttactggtaa acatattgca ctcgatgtat aaatcacag cttacaagct     300
tcttttgtag taaattttaat ggaacctttc tcagagtttt tacaacaagg ttctaatttt    360
tctcttaatc ttcatccatt aaatgtgtgc tatgataagg tgatctcagg tgttgataca     420
actgtaacaa gtagcccaga aggatcagtt gtaacaagta gcccagaagg agcagctgta     480
acaagtagcc cagaaggagc agctgtaaca agtagcccag aaggatcagt tgtaacaagt     540
agcccagaag gagcagctat aacaagtagc cagaaggag cagctataac aagtagccca      600
gaaggatcag ttgtaacaag tagcccagaa ggatcagttg taacaagtag cccagaagga     660
gcagctgtaa caagtagccc agaaggatca gttgtaacaa gtagcccaga aggatcagtt     720
gtaacaagta gcccagaagg agcagctgta acaagtagcc cagaaggagc agctgtaaca     780
agtagcccag aaggagcagc tgtaacaagt agcccagaag gatcagttgt aacaagtagc     840
ccagaaggag cagctgtaac aagtagccca gaaggatcag ttgtaacaag tagcccagaa     900
ggagcagctg taacaagtag cccagaagga gcagctgtaa caagtagccc agaaggatca     960
gttgtaacaa gtagcccaga aggagcagct ataacaagta gcccagaagg agcagctata    1020
acaagtagcc cagaaggatc agttgtaaca agtagcccag aaggatcagt tgtaacaagt    1080
agcccagaag gagcagctgt aacaagtagc ccagaaggat cagttgtaac aagtagccca    1140
gaaggatcag ttgtaacaag tagcccagaa ggagcagctg taacaagtag cccagaagga    1200
gcagctgtaa caagtagccc agaaggagca gctgtaacaa gtagcccaga aggatcagtt    1260
gtaacaagta gcccagaagg agcagctgta acaagtagcc cagaaggatc agttgtaaca    1320
agtagcccag aaggagcagc tgtaacaagt agcccagaag gatcagctgt aacaagtagc    1380
ccagaaggag cagctgtaac aagtagccca gaaggatcag ttgtaacaag tagcccagaa    1440
ggagcagctg taacaagtag cccagaagga tcagttgtaa caagtagccc agaaggagca    1500
gctgtaacaa gtagcccaga aggagcagct gtaacaagta gcccagaagg agcagctgta    1560
acaagtagcc cagaaggagc agctgtaaca agtagcccag aaggagcagc tgtaacaagt    1620
agcccagaag gatcagttgt aacaagtagc ccagaaggat cagttgtaac aagtagccca    1680
gaaggatcag ttgtaacaag tagcccagaa ggagcagctg taacaagtag cccagaagga    1740
tcagttgtaa caagtagccc agaaggagca gctgtaacaa gtagcccaga aggatcagtt    1800
gtaacaagta gcccagaagg atcagttgta acaagtagcc cagaaggatc agttgtaaca    1860
agtagcccag aaggagcagc tgtaacaagt agcccagaag gagcagctgt aacaagtagc    1920
ccagaagtag caaaaggatt tacatttggt ggtcgtagtg gtgaaagagt atttactggc    1980
atctaa                                                               1986
```

<210> SEQ ID NO 44
<211> LENGTH: 1593
<212> TYPE: DNA
<213> ORGANISM: Ehrlichia ruminantium

<400> SEQUENCE: 44

```
atggttcatt caacagcaga agattgtatg cttcatttaa caacaagaat tgacaatatt      60
gattttggaa atgatttaag tatctatagt aataatcaat tctctgtttc aaatggtgat     120
attacaatgg agattggata tcatcctcat gagcatgaag aaggtcatga agagggtcat     180
gaagatcatc atggcgaata tcatgttatg tttacgagta atggtcacgt actttcagat     240
tttcatggtg ttactggtaa acatattaca cttgatgtat aaatcacag cttacaagct     300
tcttttgtag taaatttaat ggaaccttt tcagagtttt tacaacaagg ttctaatttt     360
tctcttaatc ttcatccatt aatagaagat tgtggtcttg atggtcatga tcatgttcat     420
catgtaggtg ttttgggtag tgatatagtt tctgctgcta atacaagttc tgaagttact     480
gaatcaaatc aaggatctag cgcttctgta gtaggtgatg caggtgtaca aagttctgaa     540
gttactgaat caaatcaagg atctagcgct tctgtagtag gtgatgcagg tgtacaaagt     600
tctgaagtta ctgaatcaaa tcaaggatct agcgcttctg tagtaggtga tgcaggtgta     660
caaagttctg aagttactga atcaaatcaa ggatctagcg cttctgtagt aggtgatgca     720
ggtgtacaaa gttctgaagt tactgaatca aatcaaggat ctagcgcttc tgtagtaggt     780
gatgtaggtg tacaaagttc tgaagttact gaatcaaatc aaggatctag cgcttctgta     840
gtaggtgatg caggtgtaca aagttctgaa gttactgaat caaatcaagg atctagcgct     900
tctgtagtag gtgatgtagg tgtacaaagt tctgaagtta ctgaatcaaa tcaaggatct     960
agcgcttctg tagtaggtga tgcaggtgta caaagttctg aagttactga atcaaatcaa    1020
ggatctagcg cttctgtagt aggtgatgca ggtgtacaaa gttctgaagt tactgaatca    1080
aatcaaggat ctagcgcttc tgtagtaggt gatgcaggtg tacaaagttc tgaagttact    1140
gaatcaaatc aaggatctag cgcttctgta gtaggtgatg taggtgtaca aagttctgaa    1200
gttactgaat caaatcaagg atctagcgct tctgtagtag gtgatgcagg tgtacaaagt    1260
tctgaagtta ctgaatcaaa tcaaggatct agcgcttctg tagtaggtga tgcaggtgta    1320
caaagttctg aagttactga atcaaatcaa ggatctagcg cttctgtagt aggtgatgca    1380
ggtgtacaaa gttctgaagt tactgaatca aatcaaggat ctagcgcttc tgtagtaggt    1440
gatgcaggtg tacaaagttc tgaagttact gaatcaaatc aaggatctag cgcttctgta    1500
gtaggtgatg caggtgtaca aagttctgaa gttactgaat caaatcaagg atctagtgct    1560
tctgtagtag gtgatgcagg tattaaaatt tag                                 1593
```

<210> SEQ ID NO 45
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 45

```
Ser Val Ser Ala Pro Ala Thr Glu Asp Ser Val Ser
1               5                   10
```

<210> SEQ ID NO 46
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 46

```
Thr Glu Asp Ser Val Ser Ala Pro Ala Thr Glu Asp Ser Val Ser Ala
1               5                   10                  15

Pro Ala

<210> SEQ ID NO 47
<211> LENGTH: 24
<212> TYPE: DNA
<213> ORGANISM: Artificial Sequence
<220> FEATURE:
<223> OTHER INFORMATION: Synthetic Peptide

<400> SEQUENCE: 47
aatcaatgta gtatgtttct ttta                                        24

<210> SEQ ID NO 48
<211> LENGTH: 24
<212> TYPE: DNA
<213> ORGANISM: Artificial Sequence
<220> FEATURE:
<223> OTHER INFORMATION: Synthetic Peptide

<400> SEQUENCE: 48
attttacagg ttatatttca gtta                                        24

<210> SEQ ID NO 49
<211> LENGTH: 17
<212> TYPE: DNA
<213> ORGANISM: Artificial Sequence
<220> FEATURE:
<223> OTHER INFORMATION: Synthetic Peptide

<400> SEQUENCE: 49
ttgtgcaggg aaagttg                                                17

<210> SEQ ID NO 50
<211> LENGTH: 24
<212> TYPE: DNA
<213> ORGANISM: Artificial Sequence
<220> FEATURE:
<223> OTHER INFORMATION: Synthetic Peptide

<400> SEQUENCE: 50
aatgaaagta aataagaaag tgta                                        24

<210> SEQ ID NO 51

<400> SEQUENCE: 51

000

<210> SEQ ID NO 52
<211> LENGTH: 657
<212> TYPE: DNA
<213> ORGANISM: Ehrlichia canis

<400> SEQUENCE: 52
atgctattta tactaatggg ttattgtatg cttcatttaa caacagaaat cacaaacatt    60
gattttgctc atgattttca tatacatcaa ggtgaaagat tggtgtttc aagtggtgat    120 ctagaacttg atattgaaaa ccatcctgga catggttatc atattttatt taagaacaat   180
ggccatgtaa tatcagattt acatggtgct aaagctgaag actttaactt tgatatgaag   240
gatcatagtt tgaatgtttc tttcttaatt gatccaatgg ctccttttca tgagttagat   300
gttaataacc atcctaactt ctttatttct gtgcatgctt atcaagatgg ttgtgataat   360
```

| | |
|---|---|
| tgtgtacatg gaaatccatc acgtcctgct atagtaaatc aagctcaagt tttattacca | 420 |
| agtggagtta ctgaagattc tgtttctgct ccagctactg aagattctgt ttctgctcca | 480 |
| gctactgaag attctgtttc tgctccagct actgaagatt ctgtttctgc tccagctact | 540 |
| gaagattctg tttctgctct agctactgca gcaacaggtt caacaacatc atataatcac | 600 |
| aacactggac ttgagttttt agatttagat tctgatattc ttaacatgtt gtactaa | 657 |

<210> SEQ ID NO 53
<211> LENGTH: 218
<212> TYPE: PRT
<213> ORGANISM: Ehrlichia canis

<400> SEQUENCE: 53

Met Leu Phe Ile Leu Met Gly Tyr Cys Met Leu His Leu Thr Thr Glu
1               5                   10                  15

Ile Thr Asn Ile Asp Phe Ala His Asp Phe His Ile His Gln Gly Glu
                20                  25                  30

Arg Phe Gly Val Ser Ser Gly Asp Leu Glu Leu Asp Ile Glu Asn His
            35                  40                  45

Pro Gly His Gly Tyr His Ile Leu Phe Lys Asn Gly His Val Ile
        50                  55                  60

Ser Asp Leu His Gly Ala Lys Ala Glu Asp Phe Asn Phe Asp Met Lys
65                  70                  75                  80

Asp His Ser Leu Asn Val Ser Phe Leu Ile Asp Pro Met Ala Pro Phe
                85                  90                  95

His Glu Leu Asp Val Asn Asn His Pro Asn Phe Ile Ser Val His
            100                 105                 110

Ala Tyr Gln Asp Gly Cys Asp Asn Cys Val His Gly Asn Pro Ser Arg
        115                 120                 125

Pro Ala Ile Val Asn Gln Ala Gln Val Leu Leu Pro Ser Gly Val Thr
    130                 135                 140

Glu Asp Ser Val Ser Ala Pro Ala Thr Glu Asp Ser Val Ser Ala Pro
145                 150                 155                 160

Ala Thr Glu Asp Ser Val Ser Ala Pro Ala Thr Glu Asp Ser Val Ser
                165                 170                 175

Ala Pro Ala Thr Glu Asp Ser Val Ser Ala Leu Ala Thr Ala Ala Thr
            180                 185                 190

Gly Ser Thr Thr Ser Tyr Asn His Asn Thr Gly Leu Glu Phe Leu Asp
        195                 200                 205

Leu Asp Ser Asp Ile Leu Asn Met Leu Tyr
    210                 215

<210> SEQ ID NO 54
<211> LENGTH: 630
<212> TYPE: DNA
<213> ORGANISM: Ehrlichia canis

<400> SEQUENCE: 54

| | |
|---|---|
| atgctattta tactaatggg ttattgtatg cttcatttaa caacagaaat cacaaacatt | 60 |
| gattttgctc atgattttca tatacatcaa ggtgaaagat tggtgtttc aagtggtgat | 120 |
| ctagaacttg atgttgaaaa ccatcctgga catggttatc atatttttatt taagaacaat | 180 |
| ggccatgtaa tatcagattt atatggtgct aaagctgaag actttaactt taatatgaag | 240 |
| gatcatagtt tgaatgtttc tttcttaatt gatccaatgg ctcctttca tgagttagat | 300 |

```
gttaataacc atcctaactt ctttatttct gtgcatgctt atcaagatgg ttgtgataat    360
tgtgtacatg gaaatccatc acgtcctgct atagtaaatc aagctcaagt tttattacca    420
agtggagtta ctgaagattc tgtttctgct ccagctactg aagattctgt ttctgctcca    480
gctactgaag attctgtttc tgctccagct actgaagatt ctgtttctgc tccagctact    540
gcagcaacag gttcaacaac atcatataat cacaacactg gacttgagtt tttagattta    600
gattctgata ttcttaacat gttgtactaa                                    630
```

<210> SEQ ID NO 55  
<211> LENGTH: 209  
<212> TYPE: PRT  
<213> ORGANISM: Ehrlichia canis

<400> SEQUENCE: 55

```
Met Leu Phe Ile Leu Met Gly Tyr Cys Met Leu His Leu Thr Thr Glu
1               5                   10                  15

Ile Thr Asn Ile Asp Phe Ala His Asp Phe His Ile His Gln Gly Glu
            20                  25                  30

Arg Phe Gly Val Ser Ser Gly Asp Leu Glu Leu Asp Val Glu Asn His
        35                  40                  45

Pro Gly His Gly Tyr His Ile Leu Phe Lys Asn Asn Gly His Val Ile
    50                  55                  60

Ser Asp Leu Tyr Gly Ala Lys Ala Glu Asp Phe Asn Phe Asn Met Lys
65                  70                  75                  80

Asp His Ser Leu Asn Val Ser Phe Leu Ile Asp Pro Met Ala Pro Phe
                85                  90                  95

His Glu Leu Asp Val Asn Asn His Pro Asn Phe Phe Ile Ser Val His
            100                 105                 110

Ala Tyr Gln Asp Gly Cys Asp Asn Cys Val His Gly Asn Pro Ser Arg
        115                 120                 125

Pro Ala Ile Val Asn Gln Ala Gln Val Leu Leu Pro Ser Gly Val Thr
    130                 135                 140

Glu Asp Ser Val Ser Ala Pro Ala Thr Glu Asp Ser Val Ser Ala Pro
145                 150                 155                 160

Ala Thr Glu Asp Ser Val Ser Ala Pro Ala Thr Glu Asp Ser Val Ser
                165                 170                 175

Ala Pro Ala Thr Ala Ala Thr Gly Ser Thr Thr Ser Tyr Asn His Asn
            180                 185                 190

Thr Gly Leu Glu Phe Leu Asp Leu Asp Ser Asp Ile Leu Asn Met Leu
        195                 200                 205

Tyr
```

<210> SEQ ID NO 56  
<211> LENGTH: 1002  
<212> TYPE: DNA  
<213> ORGANISM: Ehrlichia canis

<400> SEQUENCE: 56

```
atgctattta tactaatggg ttattgtatg cttcatttaa caacagaaat cacaaacatt     60
gattttgctc atgattttca tatacatcaa ggtgaaagat tggtgtttc aagtggtgat    120 ctagaacttg atgttgaaaa ccatcctgga catggttatc atattttatt taagaacaat    180
ggccatgtaa tatcagattt acatggtgct aaagctgaag actttaactt taatatgaag    240
gatcatagtt tgaatgtttc tttccttaat tgatccaatag ctccttttca tgagttagat    300
```

```
gttaataacc atcctaactt ctttatttct gtgcatgctt atcaagatgg ttgtgataat    360
tgtgtacatg gaaatccatc acgtcctgct atagtaaatc aagctcaagt tttattacca    420
agtggagtta ctgaagattc tgtttctgct ccagctactg aagattctgt ttctgctcca    480
gctactgaag attctgtttc tgctccagct actgaagatt ctgtttctgc tccagctact    540
gaagattctg tttctgctcc agctactgaa gattctgttt ctgctccagc tactgaagat    600
tctgtttctg ctccagctac tgaagattct gtttctgctc cagctactga agattctgtt    660
tctgctccag ctactgaaga ttctgtttct gctccagcta ctgaagattc tgtttctgct    720
ccagctactg aagattctgt ttctgctcca gctactgaag attctgtttc tgctccagct    780
actgaagatt ctgtttctgc tccagctact gaagattctg tttctgctcc agctactgaa    840
gattctgttt ctgctccagc tactgaagat tctgtttctg ctccagctac tgaagattct    900
gtttctgctc cagctactgc agcaacaggt tcaacaacat catataatca aacactggaa    960
cttgagtttt tagattctga tattcttaac atgttgtact aa                      1002

<210> SEQ ID NO 57
<211> LENGTH: 333
<212> TYPE: PRT
<213> ORGANISM: Ehrlichia canis

<400> SEQUENCE: 57

Met Leu Phe Ile Leu Met Gly Tyr Cys Met Leu His Leu Thr Thr Glu
1               5                   10                  15

Ile Thr Asn Ile Asp Phe

Ser Ala Pro Ala Thr Glu Asp Ser Val Ser Ala Pro Ala Thr Glu Asp
                260                 265                 270

Ser Val Ser Ala Pro Ala Thr Glu Asp Ser Val Ser Ala Pro Ala Thr
            275                 280                 285

Glu Asp Ser Val Ser Ala Pro Ala Thr Glu Asp Ser Val Ser Ala Pro
290                 295                 300

Ala Thr Ala Ala Thr Gly Ser Thr Thr Ser Tyr Asn His Asn Thr Gly
305                 310                 315                 320

Leu Glu Phe Leu Asp Ser Asp Ile Leu Asn Met Leu Tyr
                325                 330

<210> SEQ ID NO 58
<211> LENGTH: 1002
<212> TYPE: DNA
<213> ORGANISM: Ehrlichia canis

<400> SEQUENCE: 58
atgctattta tactaatggg ttattgtatg cttcatttaa aacagaaat cacaaacatt      60 gattttgctc atgattttca tatacatcaa ggtgaaagat ttggtgtttc aagtggtgat    120
ctagaacttg atattgcaaa ccatcctgga catggttatc atatttttatt taagaacaat   180 ggccatgtaa tatcagattt acatggtgtt aaagctgaag actttaactt taatatgaag    240
gatcatagtt tgaatgtttc tttcttaatt gatccaatgg ctccttttca tgagttagat    300
gttaataacc atcctaactt ctttatttct atgcatgctt atcaagatgg ttgtgataat    360
tgtgtacatg gaaatccatc acgtcctgct atagtaaatc aagctcaagt tttattacca    420
agtggagtta ctgaagattc tgttctgct ccagctactg aagattctgt ttctgctcca     480
gctactgaag attctgtttc tgctccagct actgaagatt ctgttctgc tccagctact    540 gaagattctg tttctgctcc agctactgaa gattctgttt ctgctccagc tactgaagat   600
tctgtttctg ctccagctac tgaagattct gtttctgctc cagctactga agattctgtt   660
tctgctccag ctactgaaga ttctgtttct gctccagcta ctgaagattc tgtttctgct   720
ccagctactg aagattctgt tctgctcca gctactgaag attctgtttc tgctccagct    780
actgaagatt ctgtttctgc tccagctact gaagattctg tttctgctcc agctactgaa   840
gattctgttt ctgctccagc tactgaagat tctgtttctg ctccagctac tgaagattct   900
gtttctgctc cagctactgc agcaacaggt tcaacaacat catataatca aacactgaa    960 cttgagtttt tagattctgg tattcttaac atgttgtact aa                      1002

<210> SEQ ID NO 59
<211> LENGTH: 333
<212> TYPE: PRT
<213> ORGANISM: Ehrlichia canis

<400> SEQUENCE: 59

Met Leu Phe Ile Leu Met Gly Tyr Cys Met Leu His Leu Thr Thr Glu
1               5                   10                  15

Ile Thr Asn Ile Asp Phe Ala His Asp Phe His Ile His Gln Gly Glu
            20                  25                  30

Arg Phe Gly Val Ser Ser Gly Asp Leu Glu Leu Asp Ile Ala Asn His
        35                  40                  45

Pro Gly His Gly Tyr His Ile Leu Phe Lys Asn Asn Gly His Val Ile
    50                  55                  60

Ser Asp Leu His Gly Val Lys Ala Glu Asp Phe Asn Phe Asn Met Lys

```
                65                  70                  75                  80
Asp His Ser Leu Asn Val Ser Phe Leu Ile Asp Pro Met Ala Pro Phe
                    85                  90                  95

His Glu Leu Asp Val Asn Asn His Pro Asn Phe Phe Ile Ser Met His
                100                 105                 110

Ala Tyr Gln Asp Gly Cys Asp Asn Cys Val His Gly Asn Pro Ser Arg
            115                 120                 125

Pro Ala Ile Val Asn Gln Ala Gln Val Leu Leu Pro Ser Gly Val Thr
        130                 135                 140

Glu Asp Ser Val Ser Ala Pro Ala Thr Glu Asp Ser Val Ser Ala Pro
145                 150                 155                 160

Ala Thr Glu Asp Ser Val Ser Ala Pro Ala Thr Glu Asp Ser Val Ser
                165                 170                 175

Ala Pro Ala Thr Glu Asp Ser Val Ser Ala Pro Ala Thr Glu Asp Ser
            180                 185                 190

Val Ser Ala Pro Ala Thr Glu Asp Ser Val Ser Ala Pro Ala Thr Glu
        195                 200                 205

Asp Ser Val Ser Ala Pro Ala Thr Glu Asp Ser Val Ser Ala Pro Ala
210                 215                 220

Thr Glu Asp Ser Val Ser Ala Pro Ala Thr Glu Asp Ser Val Ser Ala
225                 230                 235                 240

Pro Ala Thr Glu Asp Ser Val Ser Ala Pro Ala Thr Glu Asp Ser Val
                245                 250                 255

Ser Ala Pro Ala Thr Glu Asp Ser Val Ser Ala Pro Ala Thr Glu Asp
            260                 265                 270

Ser Val Ser Ala Pro Ala Thr Glu Asp Ser Val Ser Ala Pro Ala Thr
        275                 280                 285

Glu Asp Ser Val Ser Ala Pro Ala Thr Glu Asp Ser Val Ser Ala Pro
    290                 295                 300

Ala Thr Ala Ala Thr Gly Ser Thr Thr Ser Tyr Asn His Asn Thr Glu
305                 310                 315                 320

Leu Glu Phe Leu Asp Ser Gly Ile Leu Asn Met Leu Tyr
                325                 330

<210> SEQ ID NO 60
<211> LENGTH: 954
<212> TYPE: DNA
<213> ORGANISM: Ehrlichia canis

<400> SEQUENCE: 60
atgctattta tactaatggg ttattgtatg cttcatttaa caacagaaat cacaaacatt      60
gattttgctc atgattttca tatacatcaa ggtgaaagat ttggtgtttc aagtggtgat     120
ctagaacttg atattgaaaa ccatcctgga catggttatc atattttatt taagaacaat     180
ggccatgtaa tatcagattt acatggtgtt aaagctgaag actttaactt taatatgaag     240
gatcatagtt tgaatgcttc tttcttaatt gatccaatgg ctccttttca tgagttagat     300
gttaataacc atcctaactt ctttatttct atgcatgctt atcaagatgg ttgtgataat     360
tgtgtacatg gaaatccatc acgtcctgct atagtaaatc aagctcaagt tttattacca     420
agtggagtta ctgaagattc tgtttctgct ccagctactg aagattctgt ttctgctcca     480
gctactgaag attctgtttc tgctccagct actgaagatt ctgttctgc tccagctact     540 gaagattctg tttctgctcc agctactgaa gattctgttt ctgctccagc tactgaagat     600
tctgtttctg ctccagctac tgaagattct gttctgctc cagctactga agattctgtt     660
```

-continued

```
tctgctccag ctactgaaga ttctgtttct gctccagcta ctgaagattc tgtttctgct    720
ccagctactg aagattctgt ttctgctcca gctactgaag attctgtttc tgctccagct    780
actgaagatt ctgttctgc tccagctact gaagattctg tttctgctcc agctactgaa    840
gattctgttt ctgctccagc tactgcagca acaggttcaa caacatcata taatcacaac    900
actggacttg agtttttaga tttaggttct gatattctta acatgttgta ctaa          954
```

<210> SEQ ID NO 61
<211> LENGTH: 317
<212> TYPE: PRT
<213> ORGANISM: Ehrlichia canis

<400> SEQUENCE: 61

```
Met Leu Phe Ile Leu Met Gly Tyr Cys Met Leu His Leu Thr Thr Glu
1               5                   10                  15

Ile Thr Asn Ile Asp Phe Ala His Asp Phe His Ile His Gln Gly Glu
            20                  25                  30

Arg Phe Gly Val Ser Ser Gly Asp Leu Glu Leu Asp Ile Glu Asn His
        35                  40                  45

Pro Gly His Gly Tyr His Ile Leu Phe Lys Asn Asn Gly His Val Ile
    50                  55                  60

Ser Asp Leu His Gly Val Lys Ala Glu Asp Phe Asn Phe Asn Met Lys
65                  70                  75                  80

Asp His Ser Leu Asn Ala Ser Phe Leu Ile Asp Pro Met Ala Pro Phe
                85                  90                  95

His Glu Leu Asp Val Asn Asn His Pro Asn Phe Ile Ser Met His
            100                 105                 110

Ala Tyr Gln Asp Gly Cys Asp Asn Cys Val His Gly Asn Pro Ser Arg
        115                 120                 125

Pro Ala Ile Val Asn Gln Ala Gln Val Leu Leu Pro Ser Gly Val Thr
    130                 135                 140

Glu Asp Ser Val Ser Ala Pro Ala Thr Glu Asp Ser Val Ser Ala Pro
145                 150                 155                 160

Ala Thr Glu Asp Ser Val Ser Ala Pro Ala Thr Glu Asp Ser Val Ser
                165                 170                 175

Ala Pro Ala Thr Glu Asp Ser Val Ser Ala Pro Ala Thr Glu Asp Ser
            180                 185                 190

Val Ser Ala Pro Ala Thr Glu Asp Ser Val Ser Ala Pro Ala Thr Glu
        195                 200                 205

Asp Ser Val Ser Ala Pro Ala Thr Glu Asp Ser Val Ser Ala Pro Ala
    210                 215                 220

Thr Glu Asp Ser Val Ser Ala Pro Ala Thr Glu Asp Ser Val Ser Ala
225                 230                 235                 240

Pro Ala Thr Glu Asp Ser Val Ser Ala Pro Ala Thr Glu Asp Ser Val
                245                 250                 255

Ser Ala Pro Ala Thr Glu Asp Ser Val Ser Ala Pro Ala Thr Glu Asp
            260                 265                 270

Ser Val Ser Ala Pro Ala Thr Glu Asp Ser Val Ser Ala Pro Ala Thr
        275                 280                 285

Ala Ala Thr Gly Ser Thr Thr Ser Tyr Asn His Asn Thr Gly Leu Glu
    290                 295                 300

Phe Leu Asp Leu Gly Ser Asp Ile Leu Asn Met Leu Tyr
305                 310                 315
```

<210> SEQ ID NO 62
<211> LENGTH: 987
<212> TYPE: DNA
<213> ORGANISM: Ehrlichia chaffeensis

<400> SEQUENCE: 62

```
atgcttcatt taacgacaga aattgataat attgatttct ctaataactt aaatattcat      60
agtgggaata ggttcgttgt tacaagtggt gacatgcagg ttgatgttgg aagtgaccct     120
gatcatggtt atcatctttt atttaaaaac aatggtcatg ttatatcaga tttccatggt     180
gtacaagctg aaactttgt atttgatgta aaaaatcaca atttaagagc ttctttctta     240
gttgatgtta tggcaccttt tacagaatta gatagcagtc agcatccaca cttctccgtt     300
aacatgcaca ctgcaaatga gtgtaattct gattgtgttt atcacaatga acatgatcat     360
gatgcacacg gaagaggtgc ggctagctct gtagctgaag gtgtaggttc tgcaataggt     420
caaatcttat ctgtaagtga cagtatagtg gttccagttc ttgaaggaaa tgctagtgaa     480
cctgttgtaa gccaagaagc agctcctgta tctgagagtg gagatgcagc aaatccagta     540
tcttcaagtg aaaatgcttc tgaaggaaat gctagtgaac ctgttgtaaa ccaagaaaca     600
gctcctgtat ctgagagtgg agatgcagca atccagtat cttcaagtga aaatgcttct     660
gaaggaagtg ctagtgaacc tgttgtaaac caagaagcag ctcctgtatc tgagagtgga     720
gatgcagcaa atccagtatc ttcaagtgaa atgcttctg aaggaaatgc tagtgaacct     780
gttgtaaacc aagaaacagc tcctgtatct gagagtggag atgcagcaaa tccagtatct     840
tcaagtgaaa atgcttctga aggaaatgct agtgaacctg ttgtaaaacca agaaacagct     900
cctgcgattc aaccacaatc tagaaattct tgttaagtg aagaagatat aactgctcag     960
tttggtaata aatacttta tttctaa                                         987
```

<210> SEQ ID NO 63
<211> LENGTH: 328
<212> TYPE: PRT
<213> ORGANISM: Ehrlichia chaffeensis

<400> SEQUENCE: 63

```
Met Leu His Leu Thr Thr Glu Ile Asp Asn Ile Asp Phe Ser Asn Asn
1               5                   10                  15

Leu Asn Ile His Ser Gly Asn Arg Phe Val Val Thr Ser Gly Asp Met
            20                  25                  30

Gln Val Asp Val Gly Ser Asp Pro Asp His Gly Tyr His Leu Leu Phe
        35                  40                  45

Lys Asn Asn Gly His Val Ile Ser Asp Phe His Gly Val Gln Ala Glu
    50                  55                  60

Asn Phe Val Phe Asp Val Lys Asn His Asn Leu Arg Ala Ser Phe Leu
65                  70                  75                  80

Val Asp Val Met Ala Pro Phe Thr Glu Leu Asp Ser Ser Gln His Pro
                85                  90                  95

His Phe Ser Val Asn Met His Thr Ala Asn Glu Cys Asn Ser Asp Cys
            100                 105                 110

Val Tyr His Asn Glu His Asp His Asp Ala His Gly Arg Gly Ala Ala
        115                 120                 125

Ser Ser Val Ala Glu Gly Val Gly Ser Ala Ile Gly Gln Ile Leu Ser
    130                 135                 140

Val Ser Asp Ser Ile Val Val Pro Val Leu Glu Gly Asn Ala Ser Glu
145                 150                 155                 160
```

```
Pro Val Ser Gln Glu Ala Ala Pro Val Ser Glu Ser Gly Asp Ala
            165                 170                 175

Ala Asn Pro Val Ser Ser Glu Asn Ala Ser Glu Gly Asn Ala Ser
            180                 185                 190

Glu Pro Val Val Asn Gln Glu Thr Ala Pro Val Ser Glu Ser Gly Asp
            195                 200                 205

Ala Ala Asn Pro Val Ser Ser Glu Asn Ala Ser Glu Gly Ser Ala
            210                 215                 220

Ser Glu Pro Val Val Asn Gln Glu Ala Ala Pro Val Ser Glu Ser Gly
225                 230                 235                 240

Asp Ala Ala Asn Pro Val Ser Ser Glu Asn Ala Ser Glu Gly Asn
            245                 250                 255

Ala Ser Glu Pro Val Val Asn Gln Glu Thr Ala Pro Val Ser Glu Ser
            260                 265                 270

Gly Asp Ala Ala Asn Pro Val Ser Ser Glu Asn Ala Ser Glu Gly
            275                 280                 285

Asn Ala Ser Glu Pro Val Val Asn Gln Glu Thr Ala Pro Ala Ile Gln
            290                 295                 300

Pro Gln Ser Arg Asn Ser Leu Leu Ser Glu Glu Asp Ile Thr Ala Gln
305                 310                 315                 320

Phe Gly Asn Lys Tyr Phe Tyr Phe
            325

<210> SEQ ID NO 64
<211> LENGTH: 885
<212> TYPE: DNA
<213> ORGANISM: Ehrlichia chaffeensis

<400> SEQUENCE: 64
atgcttcatt taacaacaga aattaatgat attgatttct ctaataattt aaatatttat    60
agtgggaata gatttgttgt tacaagtggt gacatgcagg ttgatgttgg aagtgaacct   120
gatcatggtt atcatatttt atttaaaaac aatggtcatg ttatatcaga ttttcatggt   180
gtacaagctg aaaactttgt atttgatata aaaaatcaca atttaagagc ttctttctta   240
gttgatccta tggcaccttt tacagaatta gataacagtc agcatccaca cttcgtcgtt   300
aacatgcaca ctgcaaatga atgtggttct gattgtgttc atcacaatga acatgatcat   360
gatgcacacg gaagaggtgc ggctagctct gtagctgaag gtgtaggttc tgcaataagt   420
caaatcttat ctttaagtga cagtatagtg gttccagttc ttgaaggaaa tgctagtgaa   480
cctgttgtaa gccaagaagc agctcctgta tctgagagtg gagatgcagc aaatccagta   540
tcttcaagtg aaaatgcttc tgaaggaaat gctagtgaac tgttgtaaa ccaagaagca   600
gctcctgtat ctgagagtgg agatacagca aatccagtat cttcaagtga aaatgcttct   660
gaaggaaatg ctagtgaacc tgttgtaagc caagaagcag ctcctgtatc tgagagtgga   720
gatgcagcaa atccagtatc ttcaagtgaa aatgcttctg aaggaaatgc tagtgaacct   780
gttgtaagcc aagaaactcc tgcaactcaa ccacaatcta gagattcttt gttaaatgaa   840
gaagatatgg ctgctcaatt tggtaataga tactttatt tctaa                    885

<210> SEQ ID NO 65
<211> LENGTH: 294
<212> TYPE: PRT
<213> ORGANISM: Ehrlichia chaffeensis

<400> SEQUENCE: 65
```

```
Met Leu His Leu Thr Thr Glu Ile Asn Asp Ile Asp Phe Ser Asn Asn
1               5                   10                  15

Leu Asn Ile Tyr Ser Gly Asn Arg Phe Val Val Thr Ser Gly Asp Met
            20                  25                  30

Gln Val Asp Val Gly Ser Glu Pro Asp His Gly Tyr His Ile Leu Phe
                35                  40                  45

Lys Asn Asn Gly His Val Ile Ser Asp Phe His Gly Val Gln Ala Glu
50                  55                  60

Asn Phe Val Phe Asp Ile Lys Asn His Asn Leu Arg Ala Ser Phe Leu
65                  70                  75                  80

Val Asp Pro Met Ala Pro Phe Thr Glu Leu Asp Asn Ser Gln His Pro
                85                  90                  95

His Phe Val Val Asn Met His Thr Ala Asn Glu Cys Gly Ser Asp Cys
                100                 105                 110

Val His His Asn Glu His Asp His Asp Ala His Gly Arg Gly Ala Ala
            115                 120                 125

Ser Ser Val Ala Glu Gly Val Gly Ser Ala Ile Ser Gln Ile Leu Ser
130                 135                 140

Leu Ser Asp Ser Ile Val Val Pro Val Leu Glu Gly Asn Ala Ser Glu
145                 150                 155                 160

Pro Val Val Ser Gln Glu Ala Ala Pro Val Ser Glu Ser Gly Asp Ala
                165                 170                 175

Ala Asn Pro Val Ser Ser Ser Glu Asn Ala Ser Glu Gly Asn Ala Ser
                180                 185                 190

Glu Pro Val Val Asn Gln Glu Ala Ala Pro Val Ser Glu Ser Gly Asp
                195                 200                 205

Thr Ala Asn Pro Val Ser Ser Ser Glu Asn Ala Ser Glu Gly Asn Ala
            210                 215                 220

Ser Glu Pro Val Val Ser Gln Glu Ala Ala Pro Val Ser Glu Ser Gly
225                 230                 235                 240

Asp Ala Ala Asn Pro Val Ser Ser Ser Glu Asn Ala Ser Glu Gly Asn
                245                 250                 255

Ala Ser Glu Pro Val Val Ser Gln Glu Thr Pro Ala Thr Gln Pro Gln
                260                 265                 270

Ser Arg Asp Ser Leu Leu Asn Glu Glu Asp Met Ala Ala Gln Phe Gly
            275                 280                 285

Asn Arg Tyr Phe Tyr Phe
            290

<210> SEQ ID NO 66
<211> LENGTH: 987
<212> TYPE: DNA
<213> ORGANISM: Ehrlichia chaffeensis

<400> SEQUENCE: 66 atgcttc

```
caaatcttat ctttaagtga cagtatagtg gttccagttc ttgaaggaaa tgctagtgaa    480
cctgttgtaa gccaagaagc agctcctgta tctgagagtg gagatgcagc aaatccagta    540
tcttcaagtg aaaatgcttc tgaaggaaat gctagtgaac ctgttgtaaa ccaagaagcg    600
gctcctgtat ctgagagtgg agatacagca aatccagtat cttcaagtga aaatgcttct    660
gaaggaaatg ctagtgaacc tgttgtaagc caagaagcag ctcctgtatc tgagagtgga    720
gatgcagcaa atccagtatc ttcaagtgaa aatgcttctg aaggaaatgc tagtgaacct    780
gttgtaagcc aagaagcagc tcctgtatct gagagtggag atgcagcaaa tccagtatct    840
tcaagtgaaa atgcttctga aggaaatgct agtggacctg ttgtaaacca agaaacagct    900
cctgcgattc aaccacaatc tagaaattct tgttaagtg aagaagatat aactgctcag    960
tttggtaata aatactttta tttctaa                                       987
```

<210> SEQ ID NO 67
<211> LENGTH: 328
<212> TYPE: PRT
<213> ORGANISM: Ehrlichia chaffeensis

<400> SEQUENCE: 67

```
Met Leu His Leu Thr Thr Glu Ile Asn Asp Ile Asp Phe Ser Asn Asn
 1               5                  10                  15

Leu Asn Ile Tyr Ser Gly Asn Arg Phe Val Val Thr Ser Gly Asp Met
            20                  25                  30

Gln Val Asp Val Gly Ser Glu Pro Asp His Gly Tyr His Ile Leu Phe
        35                  40                  45

Lys Asn Asn Gly His Val Ile Ser Asp Phe His Gly Val Gln Ala Glu
    50                  55                  60

Asn Phe Val Phe Asp Ile Lys Asn His Asn Leu Arg Ala Ser Phe Leu
65                  70                  75                  80

Val Asp Pro Met Ala Pro Phe Thr Glu Leu Asp Asn Ser Gln His Pro
                85                  90                  95

His Phe Val Val Asn Met His Thr Ala Asn Glu Cys Gly Ser Asp Cys
            100                 105                 110

Val His His Asn Glu His Asp His Asp Ala His Gly Arg Gly Ala Ala
        115                 120                 125

Ser Ser Val Ala Glu Gly Val Gly Ser Ala Ile Ser Gln Ile Leu Ser
    130                 135                 140

Leu Ser Asp Ser Ile Val Val Pro Val Leu Glu Gly Asn Ala Ser Glu
145                 150                 155                 160

Pro Val Val Ser Gln Glu Ala Ala Pro Val Ser Glu Ser Gly Asp Ala
                165                 170                 175

Ala Asn Pro Val Ser Ser Glu Asn Ala Ser Glu Gly Asn Ala Ser
            180                 185                 190

Glu Pro Val Val Asn Gln Glu Ala Ala Pro Val Ser Glu Ser Gly Asp
        195                 200                 205

Thr Ala Asn Pro Val Ser Ser Glu Asn Ala Ser Glu Gly Asn Ala
    210                 215                 220

Ser Glu Pro Val Val Ser Gln Glu Ala Ala Pro Val Ser Glu Ser Gly
225                 230                 235                 240

Asp Ala Ala Asn Pro Val Ser Ser Glu Asn Ala Ser Glu Gly Asn
                245                 250                 255

Ala Ser Glu Pro Val Val Ser Gln Glu Ala Ala Pro Val Ser Glu Ser
            260                 265                 270
```

```
Gly Asp Ala Ala Asn Pro Val Ser Ser Glu Asn Ala Ser Glu Gly
            275                 280                 285

Asn Ala Ser Gly Pro Val Val Asn Gln Glu Thr Ala Pro Ala Ile Gln
        290                 295                 300

Pro Gln Ser Arg Asn Ser Leu Leu Ser Glu Glu Asp Ile Thr Ala Gln
305                 310                 315                 320

Phe Gly Asn Lys Tyr Phe Tyr Phe
                325

<210> SEQ ID NO 68
<211> LENGTH: 987
<212> TYPE: DNA
<213> ORGANISM: Ehrlichia chaffeensis

<400> SEQUENCE: 68
atgcttcatt taacaaca

```
His Phe Val Val Asn Met His Thr Ala Asn Glu Cys Gly Ser Asp Cys
            100             105             110

Val His His Asn Glu His Asp His Asp Ala His Gly Arg Gly Ala Ala
        115             120             125

Ser Ser Val Ala Glu Gly Val Gly Ser Ala Ile Ser Gln Ile Leu Ser
        130             135             140

Leu Ser Asp Ser Ile Val Val Pro Val Leu Glu Gly Asn Ala Ser Glu
145             150             155             160

Pro Val Val Ser Gln Glu Ala Ala Pro Val Ser Glu Ser Gly Asp Ala
            165             170             175

Ala Asn Pro Val Ser Ser Ser Glu Asn Ala Ser Glu Gly Asn Ala Ser
            180             185             190

Glu Pro Val Val Asn Gln Glu Ala Ala Pro Val Ser Glu Ser Gly Asp
        195             200             205

Thr Ala Asn Pro Val Ser Ser Ser Glu Asn Ala Ser Glu Gly Asn Ala
        210             215             220

Ser Glu Pro Val Val Ser Gln Glu Ala Ala Pro Val Ser Glu Ser Gly
225             230             235             240

Asp Ala Ala Asn Pro Val Ser Ser Ser Glu Asn Ala Ser Glu Gly Asn
            245             250             255

Ala Ser Glu Pro Val Val Ser Gln Glu Ala Ala Pro Val Ser Glu Ser
            260             265             270

Gly Asp Ala Ala Asn Pro Val Ser Ser Ser Glu Asn Ala Ser Glu Gly
            275             280             285

Asn Ala Ser Glu Pro Val Val Asn Gln Glu Thr Ala Pro Ala Ile Gln
        290             295             300

Pro Gln Ser Arg Asn Ser Leu Leu Ser Glu Glu Asp Ile Thr Ala Gln
305             310             315             320

Phe Gly Asn Lys Tyr Phe Tyr Phe
                325
```

IMMUNOREACTIVE PROTEIN ORTHOLOGS OF *EHRLICHIA CANIS* AND *E. CHAFFEENSIS*

The present invention is a continuation of U.S. application Ser. No. 14/072,029, filed Nov. 5, 2013, which is a divisional of U.S. application Ser. No. 11/917,390, now U.S. Pat. No. 8,591,906, filed as a national phase application under 35 U.S.C. 371 of International Patent Application PCT/US2006/023397, filed Jun. 15, 2006, which claims benefit of and priority to U.S. Provisional Patent Application No. 60/691,058, filed Jun. 16, 2005, all of which are incorporated by reference herein in their entirety.

FIELD OF THE INVENTION

The present invention concerns at least the fields of molecular biology, cell biology, pathology, and medicine, including veterinary medicine. In specific aspects, the present invention concerns immunoreactive gp47 and gp36 proteins in *Ehrlichia chaffeensis* and *E. canis*, respectively.

BACKGROUND OF THE INVENTION

Ehrlichiae are tick-transmitted, obligately intracellular gram-negative bacteria that primarily reside within cytoplasmic vacuoles (early endosomes) of professional phagocytes, including macrophages and neutrophils. *E. canis* causes canine monocytic ehrlichiosis (CME), a serious and sometimes fatal globally distributed disease (Troy and Forrester, 1990). *E. chaffeensis* causes human monocytotropic ehrichiosis (HME) in the United States, an emerging life-threatening disease in humans, and also causes mild to severe ehrlichiosis in canines (Breitschwerdt et al., 1998). The importance of *E. canis* as a veterinary pathogen in conjunction with the recent identification of *E. chaffeensis* as the cause of an emerging tick-borne zoonosis has highlighted the need for improved diagnostics and vaccines for both veterinary and human ehrlichioses, and thus the need for identification of immunoreactive proteins.

A small subset of proteins expressed by *E. canis* and *E. chaffeensis* react strongly with antibodies and are considered to be major immunoreactive proteins (Chen et al., 1997; Chen et al., 1994; McBride et al., 2003). Several of these proteins have been molecularly characterized, including a 200-, 140/120-, and the 28-kDa multigene family of proteins (McBride et al., 2000a; Ohashi et al. 2001; Ohashi et al., 1998a; Ohashi et al., 1998b; Reddy et al., 1998; Yu et al., 1997; Yu et al., 2000a; Yu et al., 2000b), all of which are glycoproteins (McBride et al., 2003; McBride et al., 2000; Singu et al., 2005). Until recently, bacteria were thought to be incapable of protein glycosylation, but numerous glycoproteins have recently been identified in various pathogenic bacteria (both intracellular and extracellular), including *Ehrlichia* (Benz and Schmidt, 2002; McBride et al., 2003; Schmidt et al., 2003; Upreti et al., 2003). Glycoproteins in pathogenic bacteria that have been functionally characterized include adhesins, toxins, and proteins involved in structural stability or mobility (Upreti et al., 2003). Some bacterial glycoproteins are highly immunogenic, highlighting a potential role in the development of protective immunity (Benz and Schmidt, 2002).

Several glycoproteins have been identified in *Ehrlichia* spp., including surface exposed proteins. The *E. chaffeensis* gp120 and *E. canis* gp140 are major immunoreactive surface protein orthologs that have repeat units with high serine and threonine content, and are involved in ehrlichial attachment to the host cell (Popov et al., 2000). The gp200 orthologs are the largest major immunoreactive proteins of *Ehrlichia* spp. and are found primarily in the ehrlichial cytoplasm (McBride et al., 2003). The p28/p30 multigene family of proteins comprise the major constituents of the outer membrane and are thought to play a role in surface antigenic diversity and perhaps immune evasion (Ohashi et al., 1998; Reddy et al., 1998; Yu et al., 2000). Glycosylation and phosphorylation of the p28/p30 proteins has been reported in *E. chaffeensis* (Singu et al., 2005). At least some protection in mice has been observed after immunization with recombinant p28/p30 (Ohashi et al., 1998).

The differential expression of ehrlichial antigens in tick and mammalian cells has been reported (Singu et al., 2005). Ehrlichial antigens expressed in the tick or expressed soon after inoculation in the host are likely to be recognized earliest by the host immune response. The kinetics of the antibody response that develops to the major immunoreactive proteins of *E. canis* has been investigated in experimentally-infected dogs (McBride et al., 2003). Two proteins, of approximately 19- and 37-kDa, were found to elicit the earliest acute phase antibody response, while the antibody response to p28/p30 major outer membrane proteins as well as others developed two weeks later. A total of eight major immunoreactive proteins were recognized by antibodies in convalescent sera six weeks after inoculation (McBride et al., 2003).

The present invention fulfills a need in the art by providing novel methods and compositions concerning Ehrlichial infections in mammals.

SUMMARY OF THE INVENTION

Canine monocytic ehrlichiosis is a globally-distributed tick-borne disease caused by the obligate intracellular bacterium *E. canis* and is a useful model for understanding immune and pathogenic mechanisms of *E. chaffeensis*, the causative agent of human monocytotropic ehrlichiosis. In general, the present invention concerns ehrlichial immunogenic compositions, including immunoprotective antigens as vaccines for ehrlichial diseases, such as subunit vaccines, for example. The immunogenic composition may be employed for any mammal, including, for example, humans, dogs, cats, horses, pigs, goats, or sheep.

In particular, the present invention concerns the identification of the third pair of molecularly and antigenically divergent major immunoreactive glycoprotein orthologs of *E. canis* (36-kD) and *E. chaffeensis* (47-kD). These glycoproteins have tandem repeat units that comprise major B cell epitopes with carbohydrate determinants, which contribute substantially to the immunoreactivity of these proteins. Differential expression of these glycoproteins was observed only on dense-cored morphological forms of the bacterium, and the gp36 and gp47 are surface-exposed and secreted extracellularly, in certain aspects of the invention.

Specifically, a polynucleotide encoding a major immunoreactive 36 kDa protein of *E. canis* was identified by a genomic library screen. Recombinant protein reacted strongly with immune dog sera, migrated larger than predicted by SDS-PAGE, and carbohydrate was detected, demonstrating that the protein was glycosylated. The *E. chaffeensis* gp47 ortholog was discovered by BLAST searching its genome sequence, and recombinant protein exhibited similar characteristics. Immunoelectron microscopy determined that *E. canis* gp36 and *E. chaffeensis* gp47 were expressed on the surface of the infectious dense-cored forms of the bacteria, but not the metabolically-active reticulate forms. The polynucleotide encoding *E. canis* gp36 contains six tandem repeats encoding nine amino acids, and at least some of the serines and threonines in the tandem repeats are glycosylation sites, in specific embodiments of the invention. A single repeat unit expressed as a fusion protein was sufficient for glycosylation and recognition by immune dog serum. In specific embodiments of this invention, these modifications lend support to protein immunogenicity and function. By ELISA, for example, synthetic peptide of the 9-mer repeat without post-translational modification was not recognized by antiserum against *E. canis*, and periodate treatment of the fusion protein to modify carbohydrate structures significantly reduced the antibody binding.

Thus, in embodiments of the invention novel major immunoreactive protein orthologs from *E. canis* and *E. chaffeensis* were identified that are differentially expressed glycoproteins with tandem repeats. The nine amino acid *E. canis* gp36 repeat region is an antibody epitope that requires carbohydrate for recognition, in particular aspects of the invention. The present invention provides the first demonstration of dependence on glycosylation for antibody recognition of an ehrlichial protein and that the *E. coli* can modify proteins in a similar manner to *Ehrlichia*.

Furthermore, acidic residues in the repeat region also affected mobility, a consensus that, in specific aspects of the invention, concerns these proteins as being modified on "Yin-Yang" sites with phosphorylation in addition to glycosylation. The mucin-like protein of *E. ruminantium* was recently described to act as an adhesin for tick cells. In specific embodiments, the post-translational modifications contribute to protein immunogenicity as well as adhesin function, making mucin-like proteins useful for ehrlichial subunit vaccines. Periodate treatment of the fusion protein to modify carbohydrate structures reduced the antibody binding, demonstrating partial dependence on glycosylation for recognition.

In specific aspects of the present invention, there are ehrlichial polypeptide compositions (or polynucleotide compositions that encode all or part of them) with one or more of the following characteristics: 1) comprises one or more carbohydrate moieties, which in specific embodiments comprises part of an epitope determinant; 2) comprises about four to about sixteen tandem repeats, although fewer or more than this range may be present; 3) comprises one or more moieties, such as an epitope, that are immunogenically species-specific; 4) is released extracellularly, such as by secretion; 5) comprises major B cell epitopes; 6) is surface-exposed; 7) is associated with the infectious dense-cored forms of ehrlichiae, such as on the surface, for example; 8) is associated with morula membranes (ehrlichiae organisms form microcolonies inside cellular vacuoles (morulae) that harbor many individual ehrlichiae) comprising dense-cored forms; 9) comprises virulence factor activity; and 10) comprises adhesin activity. In further aspects, recombinant polypeptide compositions of the present invention are able to be glycosylated in a cell to which it is not native, such as an *E. coli* cell, for example. The recombinant polypeptide may then be employed as an immunogenic composition, including, for example, a vaccine.

In particular embodiments of the invention, there are *E. canis* immunogenic compositions that comprise an amino acid sequence that is immunogenic, and in further particular embodiments, the immunogenicity is characterized by being at least part of an epitope. In further embodiments, the amino acid sequence comprises at least part of a vaccine composition against an ehrlichial organism, such as *E. canis*. In specific embodiments, the amino acid sequence comprises serines, threonines, or, optionally, alanine, proline, valine, and/or glutamic acid; in additional embodiments, the amino acid sequence is glycosylated. In further specific embodiments, the amino acid sequence comprises part or all of the following exemplary sequence: TEDSVSAPA (SEQ ID NO:22). In other embodiments, the *E. canis* immunogenic composition comprises part or all of the exemplary SEQ ID NO:37, SEQ ID NO:38, SEQ ID NO:39, or mixtures thereof. In other embodiments, the *E. canis* immunogenic composition is encoded by part or all of SEQ ID NO:32, SEQ ID NO:33, or SEQ ID NO:34, for example. In additional embodiments, the amino acid sequence is comprised in a pharmaceutically acceptable excipient, which in some aspects of the invention comprises an adjuvant.

In particular embodiments of the invention, there are *E. chaffeensis* immunogenic compositions that comprise an amino acid sequence that is immunogenic, and in further particular embodiments, the immunogenicity is characterized by being at least part of an epitope. In further embodiments, the amino acid sequence comprises at least part of a vaccine against an ehrlichial organism, such as *E. chaffeensis*. In specific embodiments, the amino acid sequence comprises serines, threonines, or, optionally, alanine, proline, valine, and/or glutamic acid; in additional embodiments the amino acid sequence is glycosylated. In further specific embodiments, the amino acid sequence comprises part or all of the following sequences or a mixture thereof: ASVSEG-DAVVNAVSQETPA (SEQ ID NO:23); and EGNASEPV-VSQEAAPVSESGDAANPVSSSENAS (SEQ ID NO:24); these exemplary sequences were identified in different *E. chaffeensis* strains. Other *E. chaffeensis* sequences may be identified following sequencing of gp47 in other strains; additional *E. chaffeensis* strains are tested, including 91HE17, Jax, St. Vincent, Sapulpa, and V1-V8, for example. In other embodiments, the *E. chaffeensis* immunogenic composition comprises part or all of SEQ ID NO:40, SEQ ID NO:41, or mixtures thereof. In additional embodiments, the *E. chaffeensis* immunogenic compositions are encoded by part or all of SEQ ID NO:35 or SEQ ID NO:36, for example. In additional embodiments, the amino acid sequence is comprised in a pharmaceutically acceptable excipient, which in some aspects of the invention comprises an adjuvant.

In certain embodiments of the present invention, there are immunogenic gp36 *E. canis* compositions, and particular sequences of the gp36 compositions may impart its immunogenicity; for example, a region of the gp36 composition may comprise an epitope. In particular embodiments, one or more epitopes on a gp36 composition are located in the C-terminus of a gp36 polypeptide. In some aspects of the invention, multiple different *E. canis* strains comprise immunogenic gp36 compositions, and there is significant sequence identity among the strains in regions of the gp36 compositions that comprise the epitope (such as greater than about 80%, 85%, 90%, 95%, or 98%, for example). However, in some embodiments, there may be significant sequence identity among the strains in regions of the gp36 compositions that do not comprise the epitope. In particular aspects of the invention, there is a gp36 composition that is immunogenic for more than one strain of *E. canis*, including, for example, North Carolina (Jake), Oklahoma, and North Carolina (Demon.) Other *E. canis* strains that may comprise a gp36 immunogenic composition include North Carolina (DJ), North Carolina (Fuzzy), Louisiana, Fla., and in particular aspects the epitope of the other strains is SEQ ID NO:22, although other epitopes may also be identified. In embodiments wherein an alternative gp36 *E. canis* epitope to SEQ ID NO:22 is identified, there may be provided an immunogenic composition comprising a mixture of gp36 *E. canis* epitopes, such as a mixture including SEQ ID NO:22, for example.

In certain embodiments of the present invention, there are immunogenic gp47 *E. chaffeensis* compositions, and particular sequences of the gp47 compositions may impart its immunogenicity; for example, a region of the gp47 composition may comprise an epitope. In particular embodiments, one or more epitopes on a gp47 composition are located in the C-terminus of a gp47 polypeptide. In some aspects of the invention, multiple different *E. chaffeensis* strains comprise immunogenic gp47 compositions, and there is significant sequence identity among the strains in regions of the gp47 compositions that comprise the epitope (such as greater than about 80%, 85%, 90%, 95%, or 98%, for example). However, in some embodiments, there may be significant sequence identity among the strains in regions of the gp47 compositions that do not comprise the epitope. In additional embodiments, there may not be significant sequence identity among the different strains in regions of the gp47 compositions that comprise an epitope. Thus, there may be provided an immunogenic composition comprising a mixture of gp47 *E. chaffeensis* epitopes, such as a mixture including SEQ ID NO:23 and/or SEQ ID NO:24, for example. However, in particular aspects of the invention, there is a gp47 composition that is immunogenic for more than one strain of *E. chaffeensis*.

In certain embodiments of the invention, immunogenic compositions of *E. canis* and *E. chaffeensis* comprise one or more carbohydrate moieties. In particular aspects, the carbohydrate moieties facilitate the immunogenic nature of the composition. In specific embodiments, the carbohydrate moiety is required for immunogenicity, whereas in alternative embodiments the carbohydrate moiety enhances immunogenicity. The carbohydrate moiety may be of any kind, so long as it is suitable to allow or enhance immunogenicity. The identity of a carbohydrate moiety may be determined by any suitable means in the art, although in particular aspects an enzyme that cleaves particular carbohydrates from polypeptides or peptides, followed by analysis of the cleaved carbohydrate, for example with mass spectroscopy, may be utilized. In other means, the carbohydrate is removed and assayed with a variety of lectins, which are known to bind specific sugars.

In specific embodiments of the invention, one or more carbohydrate moieties on the glycoprotein are identified by suitable method(s) in the art, for example gas chromatography/mass spectrometry.

In an embodiment of the invention, there is an immunogenic gp36 *E. canis* glycoprotein. In another embodiment of the invention, there is an immunogenic gp47 *E. chaffeensis* glycoprotein. In an additional embodiment of the invention, there is an *E. canis* composition comprising SEQ ID NO:22. In specific aspects of the invention, the composition further comprises a pharmaceutically acceptable excipient. The composition may be further defined as comprising one or more carbohydrate moieties, as comprising part or all of an epitope, and/or as a vaccine, such as a subunit vaccine.

In an additional embodiment of the invention, there is an *E. chaffeensis* composition comprising SEQ ID NO:23. In a specific embodiment, the composition further comprises a pharmaceutically acceptable excipient. The composition may be further defined as comprising one or more carbohydrate moieties, as comprising part or all of an epitope, and/or as a vaccine, such as a subunit vaccine.

In another embodiment of the invention, there is an *E. chaffeensis* composition comprising SEQ ID NO:24. In a specific embodiment, the composition further comprises a pharmaceutically acceptable excipient. The composition may be further defined as comprising one or more carbohydrate moieties, as comprising part or all of an epitope, and/or as a vaccine, such as a subunit vaccine.

In another embodiment of the invention, there is an *E. canis* composition comprising a polypeptide encoded by at least part of the polynucleotide of SEQ ID NO:32; an *E. canis* composition comprising a polypeptide encoded by at least part of the polynucleotide of SEQ ID NO:33; an *E. canis* composition comprising a polypeptide encoded by at least part of the polynucleotide of SEQ ID NO:34; an *E. chaffeensis* composition comprising a polypeptide encoded by at least part of the polynucleotide of SEQ ID NO:35; or an *E. chaffeensis* composition comprising a polypeptide encoded by at least part of the polynucleotide of SEQ ID NO:36.

In a specific embodiment, there is an isolated polynucleotide that encodes SEQ ID NO:22, an isolated polynucleotide that encodes SEQ ID NO:23, and isolated polynucleotide that encodes SEQ ID NO:24, an isolated polynucleotide of SEQ ID NO:32, an isolated polynucleotide of SEQ ID NO:33, an isolated polynucleotide of SEQ ID NO:34, an isolated polynucleotide of SEQ ID NO:35, and/or an isolated polynucleotide of SEQ ID NO:36.

In particular embodiments, there is an isolated polynucleotide, comprising: a) a polynucleotide that encodes SEQ ID NO:37; or b) a polynucleotide that is at least about 90% identical to the polynucleotide of a) and that encodes an immunoreactive *E. canis* gp36 polypeptide. In a specific embodiment, the polynucleotide is further defined as SEQ ID NO:32.

In a further embodiment of the invention, there is an isolated polynucleotide, comprising: a) a polynucleotide that encodes SEQ ID NO:38; or b) a polynucleotide that is at least about 90% identical to the polynucleotide of a) and that encodes an immunoreactive *E. canis* gp36 polypeptide. In a specific embodiment, the polynucleotide is further defined as SEQ ID NO:33. In additional aspects of the invention, there is an isolated polynucleotide, comprising: a) a polynucleotide that encodes SEQ ID NO:39; or b) a polynucleotide that is at least about 90% identical to the polynucleotide of a) and that encodes an immunoreactive *E. canis* gp36 polypeptide. In a specific embodiment the polynucleotide is further defined as SEQ ID NO:34.

In an additional particular embodiment, there is an isolated polynucleotide, comprising: a) a polynucleotide that encodes SEQ ID NO:40; or b) a polynucleotide that is at least about 90% identical to the polynucleotide of a) and that encodes an immunoreactive *E. chaffeensis* gp47 polypeptide. In a specific embodiment, the polynucleotide is further defined as SEQ ID NO:35.

In another particular embodiment, there is an isolated polynucleotide, comprising: a) a polynucleotide that encodes SEQ ID NO:41; or b) a polynucleotide that is at least about 90% identical to the polynucleotide of a) and that encodes an immunoreactive *E. chaffeensis* gp47 polypeptide. In a specific embodiment, the polynucleotide is further defined as SEQ ID NO:36.

Polynucleotides of the invention may be comprised in a vector, such as a viral vector or a non-viral vector. An exemplary viral vector includes an adenoviral vector, a retroviral vector, a lentiviral vector, an adeno-associated vector, a herpes virus vector, or a vaccinia virus vector. In a specific embodiment, the non-viral vector is a plasmid.

Polynucleotides may be comprised in and/or with liposomes. In a specific aspect, vectors comprise a promoter operably linked to the polynucleotide, such as one operable in a prokaryote, a eukaryote, or both, for example. Polynucleotides may be comprised in a pharmaceutically acceptable excipient.

In an additional embodiment of the invention, there is an isolated polypeptide, comprising: a) SEQ ID NO:22; or b) a gp36 polypeptide that is at least about 70% identical to SEQ ID NO:22 and that comprises immunogenic activity. In a specific embodiment, the polypeptide is comprised in a pharmaceutically acceptable excipient, and/or it may be further defined as being comprised in a pharmaceutical composition suitable as a vaccine.

In another aspect of the invention, there are isolated antibodies that bind one or more polypeptides of the invention. Antibodies may be monoclonal, polyclonal, or antibody fragments, for example.

In an additional embodiment of the invention, there is an isolated polypeptide, comprising: a) SEQ ID NO:23 or SEQ ID NO:24; or b) a gp47 polypeptide that is at least about 70% identical to SEQ ID NO:23 or SEQ ID NO:24 and that comprises immunogenic activity. The polypeptide may be comprised in a pharmaceutically acceptable excipient and/or may be further defined as being comprised in a pharmaceutical composition suitable as a vaccine.

In an additional embodiment of the invention, there is a method of providing resistance to *E. canis* or *E. chaffeensis* infection in an individual, comprising the step of delivering a therapeutically effective amount of a respective gp36 or gp47 antibody of the invention to the individual.

In another embodiment, there is a method of inducing an immune response in an individual, comprising the step of delivering to the individual a therapeutically effective amount of a gp36 or gp47 polypeptide of the invention. In an additional embodiment of the present invention, there is a method of inhibiting or preventing *E. canis* infection in a subject comprising the steps of: identifying a subject prior to exposure or suspected of being exposed to or infected with *E. canis*; and administering a polypeptide of the invention in an amount effective to inhibit *E. canis* infection.

In one aspect of the present invention, there is a method of inhibiting or preventing *E. chaffeensis* infection in a subject comprising the steps of: identifying a subject prior to exposure or suspected of being exposed to or infected with *E. chaffeensis*; and administering a polypeptide of the invention in an amount effective to inhibit *E. chaffeensis* infection. In other aspects of the invention, there is a method of identifying an *E. canis* infection in an individual, comprising the steps of: providing a sample from the individual; and assaying the sample for an antibody of the invention.

In an additional aspect of the invention, there is a method of identifying an *E. chaffeensis* infection in an individual, comprising the steps of: providing a sample from the individual; and assaying the sample for an antibody of the invention.

In one embodiment of the invention, there is an isolated composition comprising an *Ehrlichia* gp36 or gp47 glycoprotein, comprising: (a) a sequence selected from the group consisting of SEQ ID NO:37, SEQ ID NO:38, SEQ ID NO:39, SEQ ID NO:53; SEQ ID NO:55, SEQ ID NO:57, SEQ ID NO:59, and SEQ ID NO:61; (b) a sequence selected from the group consisting of SEQ ID NO:40, SEQ ID NO:41, SEQ ID NO:63, SEQ ID NO:65, SEQ ID NO:67, and SEQ ID NO:69; or (c) a sequence that is at least about 70% identical to one or more sequences in (a) or (b). The composition may be further defined as a sequence that is at least about 75%, about 80%, about 85%, about 90%, or about 95% identical to one or more sequences in (a) or (b).

The composition may be further defined as comprising a sequence selected from the group consisting of SEQ ID NO:37, SEQ ID NO:38, SEQ ID NO:39, SEQ ID NO:53; SEQ ID NO:55, SEQ ID NO:57, SEQ ID NO:59, and SEQ ID NO:61 and, optionally, it further comprises SEQ ID NO:22. The composition may also be further defined as comprising a sequence selected from the group consisting of SEQ ID NO:40, SEQ ID NO:41, SEQ ID NO:63, SEQ ID NO:65, SEQ ID NO:67, and SEQ ID NO:69 and, optionally, it further comprises one or both of SEQ ID NO:23 and SEQ ID NO:24. The composition may also be further defined as being comprised in a pharmaceutically acceptable excipient, as comprising two or more carbohydrate moieties, and/or as being comprised in a pharmaceutical composition suitable as a vaccine.

In some aspects of the invention the composition may be encoded by a polynucleotide comprising: (a) a polynucleotide selected from the group consisting of SEQ ID NO:32, SEQ ID NO:33, SEQ ID NO:34, SEQ ID NO:52, SEQ ID NO:54, SEQ ID NO:56, SEQ ID NO:58, and SEQ ID NO:60; (b) a polynucleotide selected from the group consisting of SEQ ID NO:35, SEQ ID NO:36, SEQ ID NO:62, SEQ ID NO:64, SEQ ID NO:66, and SEQ ID NO:68; (c) a polynucleotide that is at least about 70% identical to a polynucleotide of (a) or (b) and encodes an immunoreactive *E. canis* gp36 or gp47 polypeptide; or (d) a polynucleotide that hybridizes to one or more polynucleotides of (a), (b), or (c) under stringent conditions. In specific embodiments of the invention, the polynucleotide of (c) is at least about 70% identical, at least about 75% identical, at least about 80% identical, at least about 85% identical, at least about 90% identical, or at least about 95% identical to a polynucleotide of (a) or (b) and encodes an immunoreactive *E. canis* gp36 or gp47 polypeptide.

In another embodiment of the invention, there is an isolated *Ehrlichia* polynucleotide, comprising: a) a polynucleotide selected from the group consisting of SEQ ID NO:32, SEQ ID NO:33, SEQ ID NO:34, SEQ ID NO:52, SEQ ID NO:54, SEQ ID NO:56, SEQ ID NO:58, and SEQ ID NO:60; (b) a polynucleotide selected from the group consisting of SEQ ID NO:35, SEQ ID NO:36, SEQ ID NO:62, SEQ ID NO:64, SEQ ID NO:66, and SEQ ID NO:68; (c) a polynucleotide that is at least about 70% identical, at least about 75% identical, at least about 80% identical, at least about 85% identical, at least about 90% identical, or at least about 95% identical to a polynucleotide of (a) or (b) and encodes an immunoreactive *E. canis* gp36 or gp47 polypeptide; or (d) a polynucleotide that hybridizes to one or more polynucleotides of (a), (b), or (c) under stringent conditions.

The polynucleotide may be comprised in a vector, such as a viral vector or a non-viral vector, wherein the viral vector may be an adenoviral vector, a retroviral vector, a lentiviral vector, an adeno-associated vector, a herpes virus vector, or a vaccinia virus vector and wherein the non-viral vector may be a plasmid. In further aspects of the invention, the vector comprise a promoter operably linked to the polynucleotide wherein the promoter is operable in a prokaryote, a eukaryote, or both. The polynucleotide of the invention may be comprised in a liposome and/or comprised in a pharmaceutically acceptable excipient.

In certain aspects of the invention, there is an isolated antibody that reacts immunologically to a polypeptide of the invention, and the antibody may be a monoclonal antibody, may be comprised in polyclonal antisera, or may be an antibody fragment, for example.

In other embodiments of the invention, there is a method of inducing an immune response in an individual, comprising the step of delivering to the individual a therapeutically effective amount of a polypeptide of the invention.

In additional embodiments of the invention, there is a method of inhibiting *E. canis* or *E. chaffeensis* infection in a subject comprising the steps of: identifying a subject prior to exposure or suspected of being exposed to or infected with *E. canis* or *E. chaffeensis*; and administering the polypeptide of the invention in an amount effective to inhibit *E. canis* or *E. chaffeensis* infection. In further embodiments of the invention, there is a method of identifying an *E. canis* or *E. chaffeensis* infection in an individual, comprising the steps of: providing a sample from the individual; and assaying the sample for an antibody of the invention.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features that are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIG. 1 illustrates genetic organization of the known "mucin-like" orthologs of *E. canis* and *E. chaffeensis*. White bars represent the tandem repeat regions and the gray bars represent length (base pairs) of regions upstream or downstream of the tandem repeats. *E. canis* strains illustrated include Jake (Ja), Oklahoma (Ok), and Demon (Dem), and *E. chaffeensis* strains include Arkansas (Ark) and Sapulpa (Sap).

FIGS. 2A-2B provide immunoreactivity and carbohydrate detection of recombinant gp36 and gp47. In FIG. 2A, western immunoblot of recombinant gp36 reacted with anti-*E. canis* dog serum (lane 1), and carbohydrate detection (lane 2). In FIG. 2B, western immunoblot of recombinant gp47 reacted with anti-*E. chaffeensis* dog serum (lane 1) and carbohydrate detection (lane 2).

FIGS. 3A-3B show immunoblots of *E. canis* or *E. chaffeensis* lysate with different compositions. In FIG. 3A, there is western immunoblot of *E. canis* lysate with gp36 with anti-recombinant gp36 (lane 1) and anti-*E. canis* dog serum (lane 2). In FIG. 3B, there is reactivity of *E. chaffeensis* lysate with HME patient sera (lanes 1-10), anti-recombinant *E. chaffeensis* gp47, and anti-*E. chaffeensis* dog serum.

FIGS. 5A-5C provide western immunoblot of thioredoxin control (FIGS. 5A, 5B, 5C, lane 1) and the *E. canis* gp36 single repeat fusion protein (9 amino acids) (FIGS. 5A, 5B, lane 2) probed with anti-thioredoxin (Panel A) and anti-*E. canis* dog serum (FIG. 5B). Western immunoblot of the *E. chaffeensis* gp47 single repeat fusion protein (19 amino acids) (FIG. 5C, lane 2) probed with anti-*E. chaffeensis* dog serum (FIG. 5C).

FIGS. 6A-6B shows that western immunoblot of *E. canis* gp36 and *E. chaffeensis* gp47 reacted with homologous and heterologous antibody. Native *E. canis* gp36 (lane 1), gp36 single repeat recombinant protein (lane 2), native *E. chaffeensis* gp47 (lane 3) and gp47 single repeat recombinant protein reacted with anti-recombinant gp36 (FIG. 6A) and anti-recombinant gp47 (FIG. 6B) antibody.

FIGS. 7A-7C show contribution of glycans to the antibody reactivity of *E. canis* Jake strain gp36 and *E. chaffeensis* gp47 as determined by ELISA. FIG. 7A shows antibody reactivities of untreated and periodate-treated recombinant *E. canis* gp36 with anti-*E. canis* dog serum (#2995). FIG. 7B shows immunoreactivities of the recombinant *E. canis* gp36 repeat fusion peptides containing the 9-mer, 12-mer, and 18-mer compared to those of aglycosylated synthetic peptides. FIG. 7C shows immunoreactivities of the recombinant *E. chaffeensis* gp47 repeat fusion peptide (19-mer) and aglycosylated synthetic peptide with anti-*E. chaffeensis* dog serum (#2495). OD, optical density FIGS. 8A-8B show an immunogold-labeled electronmicrograph of *E. canis* gp36 and *E. chaffeensis* gp47. In FIG. 8A, there is localization of gp36 in morulae containing the *E. canis* reticulate (R) or the dense-cored (DC) morphological forms. In FIG. 8B, there is localization of gp47 in morulae containing the *E. chaffeensis* reticulate (R) or the dense-cored (DC) morphological forms.

FIGS. 9A-9B show secreted *E. canis* and *E. chaffeensis* immunoreactive proteins. In FIG. 9A, there is western immunoblot of concentrated supernatants from *E. canis* infected DH82 with anti-*E. canis* dog serum (lane 1) and anti-recombinant *E. canis* gp36 (lane 2). In FIG. 9B, there is western immunoblot of supernatants from *E. chaffeensis*-infected DH82 cells with anti-*E. chaffeensis* dog serum (lane 1) and with anti-recombinant *E. chaffeensis* gp47 (lane 2).

DETAILED DESCRIPTION OF THE INVENTION

I. Definitions

Figure 4:
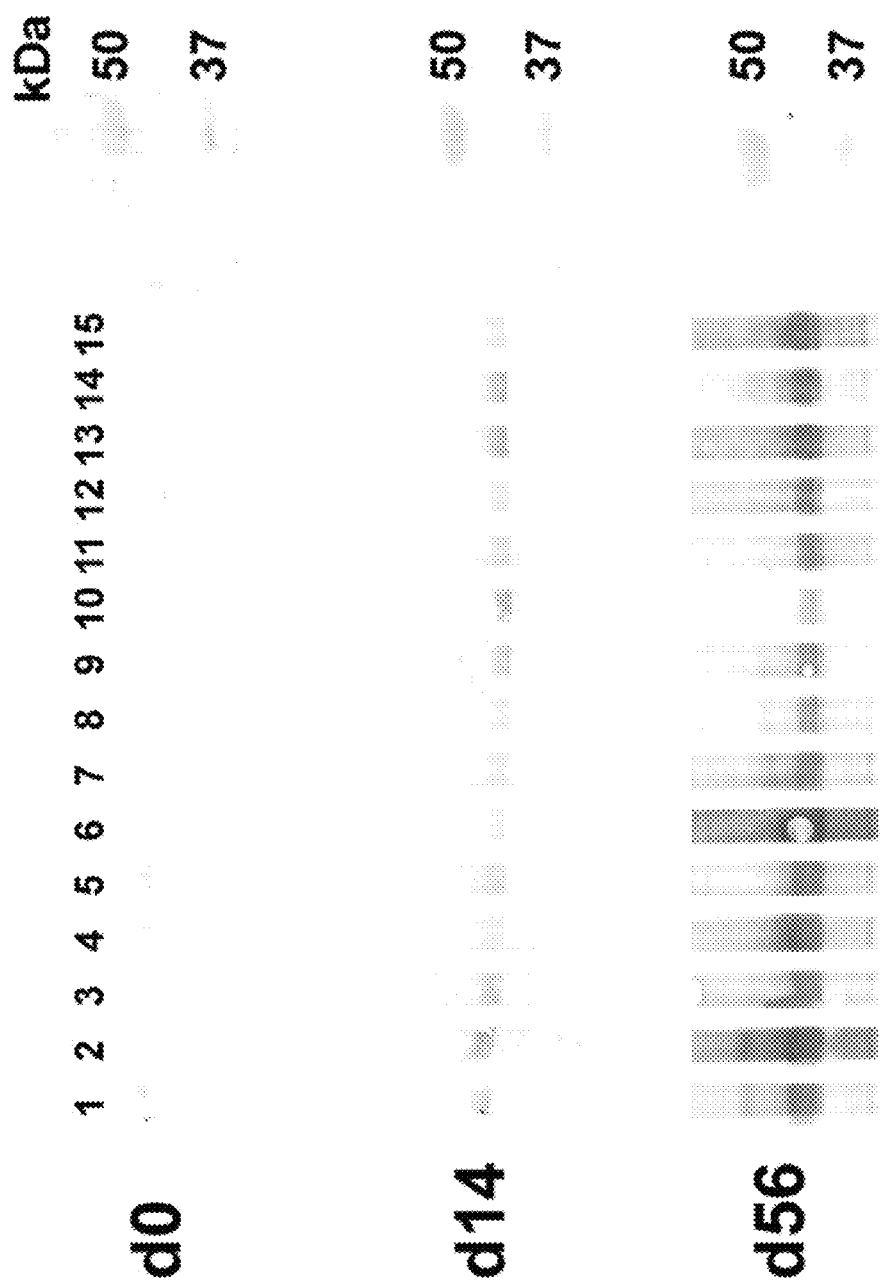
FIG. 4. shows kinetic antibody responses to *E. canis* gp36 (days 0, 14 and 56) of 15 dogs (lanes 1-15) experimentally infected with *E. canis*.

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

The term "adhesin" as used herein refers to a composition that mediates adhesion of a bacterium to a surface, such as to play a role in pathogenesis. In specific aspects of the invention, adhesins are bacterial surface antigens that often exist in the form of filamentous projections (pili or fimbriae, for example) and bind to specific cell receptors, such as those on epithelial cell membranes.

The term "carbohydrate" as used herein refers to a composition comprised of carbon, hydrogen, and oxygen, particularly in the ratio of 2H:1C:1O. The term includes sugars, starches, and celluloses, for example.

The term "epitope" as used herein refers to a site of a composition to which a specific antibody binds.

The term "glycan," which may also be referred to as a "polysaccharide," as used herein refers to a carbohydrate that can be decomposed by hydrolysis into two or more monosaccharides. In other words, it may be referred to as a chain of simple sugars (aldehyde or ketone derivatives of a polyhydric alcohol).

The term "immunogenic" as used herein refers to a composition that is able to provoke an immune response against it.

The term "immune response" as used herein refers to the reaction of the immune system to the presence of an antigen by making antibodies to the antigen. In further specific embodiments, immunity to the antigen may be developed on a cellular level, by the body as a whole, hypersensitivity to the antigen may be developed, and/or tolerance may be developed, such as from subsequent challenge. In specific embodiments, an immune response entails lymphocytes identifying an antigenic molecule as foreign and inducing the formation of antibodies and lymphocytes capable of reacting with it and rendering it less harmful.

The term "immunoreactive" as used herein refers to a composition being reactive with antibodies from the sera of an individual. In specific embodiments, a composition is immunoreactive if an antibody recognizes it, such as by binding to it.

The term "mucin" as used herein refers to one or more highly glycosylated glycoproteins with N-acetylgalactosamine (GalNAc.)

The term "ortholog" as used herein refers to a polynucleotide from one species that corresponds to a polynucleotide in another species; the two polynucleotides are related through a common ancestral species (a homologous polynucleotide). However, the polynucleotide from one species has evolved to become different from the polynucleotide of the other species.

The term "subunit vaccine" as used herein refers to a vaccine wherein a polypeptide or fragment thereof is employed, as opposed to an entire organism.

The term "vaccine" as used herein refers to a composition that provides immunity to an individual upon challenge.

The term "virulence factor" as used herein refers to one or more gene products that enable a microorganism to establish itself on or within a particular host species and enhance its pathogenicity. Exemplary virulence factors include, for example, cell surface proteins that mediate bacterial attachment, cell surface carbohydrates and proteins that protect a bacterium, bacterial toxins, and hydrolytic enzymes that may contribute to the pathogenicity of the bacterium.

The practice of the present invention will employ, unless otherwise indicated, conventional techniques of molecular biology, microbiology, recombinant DNA, and so forth which are within the skill of the art. Such techniques are explained fully in the literature. See e.g., Sambrook, Fritsch, and Maniatis, MOLECULAR CLONING: A LABORATORY MANUAL, Second Edition (1989), OLIGONUCLEOTIDE SYNTHESIS (M. J. Gait Ed., 1984), ANIMAL CELL CULTURE (R. I. Freshney, Ed., 1987), the series METHODS IN ENZYMOLOGY (Academic Press, Inc.); GENE TRANSFER VECTORS FOR MAMMALIAN CELLS (J. M. Miller and M. P. Calos eds. 1987), HANDBOOK OF EXPERIMENTAL IMMUNOLOGY, (D. M. Weir and C. C. Blackwell, Eds.), CURRENT PROTOCOLS IN MOLECULAR BIOLOGY (F. M. Ausubel, R. Brent, R. E. Kingston, D. D. Moore, J. G. Siedman, J. A. Smith, and K. Struhl, eds., 1987), CURRENT PROTOCOLS IN IMMUNOLOGY (J. E. coligan, A. M. Kruisbeek, D. H. Margulies, E. M. Shevach and W. Strober, eds., 1991); ANNUAL REVIEW OF IMMUNOLOGY; as well as monographs in journals such as ADVANCES IN IMMUNOLOGY. All patents, patent applications, and publications mentioned herein, both supra and infra, are hereby incorporated herein by reference.

II. The Present Invention

The present invention concerns compositions and methods related to *Ehrlichia* spp. proteins and the polynucleotides that encode them. In particular aspects of the invention, there are differentially-expressed and secreted major immunoreactive protein orthologs of *E. canis* and *E. chaffeensis* that elicit early antibody responses to epitopes on glycosylated tandem repeats. Specifically, the present invention concerns one or more glycoproteins from *Ehrlichia* spp., in specific embodiments. In further embodiments, the present invention relates to a glycoprotein from *Ehrlichia* spp. that is a gp36 protein. In additional embodiments, the gp36 protein is from *E. canis*. In additional embodiments, the present invention relates to a glycoprotein from *Ehrlichia* spp. that is a gp47 protein. In additional embodiments, the gp47 protein is from *E. chaffeensis*.

In specific aspects of the invention, two *E. canis* major immunoreactive proteins, 36- and 19-kDa, elicit the earliest detectable antibody response during the acute phase of canine monocytic ehrlichiosis. Genes encoding the major immunoreactive 36 kDa protein of *E. canis* and a corresponding ortholog of *E. chaffeensis* (47-kDa) were identified, and their immunoreactivity and expression were determined. Consistent with other ehrlichial immunoreactive proteins, carbohydrate was detected on the recombinant gp36 and gp47, and their masses were substantially larger than predicted (26.7- and 32.9-kDa, respectively). The *E. canis* gp36 and *E. chaffeensis* gp47 each have carboxy-terminal tandem repeat units (about four to sixteen repeats) that varied in number and amino acid sequences among different isolates. Species-specific antibody epitopes were identified in the C-terminal non-homologous repeat comprising regions of gp36 and gp47, and recombinant single repeat units from both were recognized by antibody. However, a homologous synthetic peptide repeat unit from *E. canis* gp36 was not immunoreactive, and periodate treatment of the immunoreactive recombinant peptide substantially reduced the antibody reactivity, demonstrating that glycans are important epitope determinants that are structurally conserved on the recombinant proteins expressed in *E. coli*. The *E. canis* gp36 and *E. chaffeensis* gp47 were differentially expressed only on the surface of dense-cored ehrlichiae. Furthermore, gp36 and gp47 were detected in the *ehrlichia*-free supernatants, indicating that these proteins are released extracellularly during infection. This invention concerns these newly identified glycoproteins as immunogenic compositions, such as vaccines, including subunit vaccines, or immunodiagnostic antigens, for example.

Some embodiments of the present invention are directed toward a method of inhibiting *E. canis* infection in a subject comprising the steps of identifying a subject prior to exposure or suspected of being exposed to or infected with *E. canis*; and administering a composition comprising a 36-kDa antigen of *E. canis* in an amount effective to inhibit

*E. canis* infection. The inhibition may occur through any means such as e.g., the stimulation of the subject's humoral or cellular immune responses, or by other means such as inhibiting the normal function of the 36-kDa antigen, or even competing with the antigen for interaction with some agent in the subject's body, or a combination thereof, for example.

Some embodiments of the present invention are directed toward a method of inhibiting *E. chaffeensis* infection in a subject comprising the steps of identifying a subject prior to exposure or suspected of being exposed to or infected with *E. chaffeensis*; and administering a composition comprising a 47-kDa antigen of *E. chaffeensis* in an amount effective to inhibit *E. chaffeensis* infection. The inhibition may occur through any means such as e.g., the stimulation of the subject's humoral or cellular immune responses, or by other means such as inhibiting the normal function of the 47-kDa antigen, or even competing with the antigen for interaction with some agent in the subject's body, or a combination thereof, for example.

The present invention is also directed toward a method of targeted therapy to an individual, comprising the step of administering a compound to an individual, wherein the compound has a targeting moiety and a therapeutic moiety, and wherein the targeting moiety is specific for gp36 protein. In certain aspects, the targeting moiety is an antibody specific for gp36 or ligand or ligand binding domain that binds gp36. Likewise, the therapeutic moiety may comprise a radioisotope, a toxin, a chemotherapeutic agent, an immune stimulant, a cytotoxic agent, or an antibiotic, for example.

The present invention is also directed toward a method of targeted therapy to an individual, comprising the step of administering a compound to an individual, wherein the compound has a targeting moiety and a therapeutic moiety, and wherein the targeting moiety is specific for gp47 protein. In certain aspects, the targeting moiety is an antibody specific for gp47 or ligand or ligand binding domain that binds gp47. Likewise, the therapeutic moiety may comprise a radioisotope, a toxin, a chemotherapeutic agent, an immune stimulant, a cytotoxic agent, or an antibiotic, for example.

Other embodiments of the present invention concern diagnosis of ehrlichial infection in a mammal by assaying a sample from the mammal, such as blood or serum, for example, for antibodies to a gp36 composition (for *E. canis*) or to a gp47 composition (for *E. chaffeensis*).

III. *E. canis* gp36 and *E. chaffeensis* gp47 Amino Acid Compositions

The present invention regards a polypeptide comprising *E. canis* gp36, *E. chaffeensis* gp47, or a mixture thereof. For the sake of brevity, the following section will refer to any *E. canis* gp36 and/or *E. chaffeensis* gp47 amino acid compositions of the present invention, including polypeptides and peptides.

In particular embodiments, there is an amino acid sequence, wherein the polypeptide may be a recombinant protein or it may be isolated and/or purified from nature, for example. In particular aspects, the amino acid sequence is encoded by a nucleic acid sequence. The polypeptide is useful as an antigen, in specific embodiments.

The present invention is also directed towards a method of producing the recombinant protein, comprising the steps of obtaining a vector that comprises an expression construct comprising a sequence encoding the amino acid sequence operatively linked to a promoter; transfecting the vector into a cell; and culturing the cell under conditions effective of the expression construct. The amino acid sequence may be generated synthetically, in alternative embodiments.

By a "substantially pure protein" is meant a protein that has been separated from at least some of those components that naturally accompany it. A substantially pure immunoreactive composition may be obtained, for example, by extraction from a natural source; by expression of a recombinant nucleic acid encoding an immunoreactive composition; or by chemically synthesizing the protein, for example. Accordingly, substantially pure proteins include prokaryotic proteins synthesized in *E. coli*, other prokaryotes, or any other organism in which they do not naturally occur.

Thus, in certain embodiments, the present invention concerns novel compositions comprising at least one proteinaceous molecule. As used herein, a "proteinaceous molecule," "proteinaceous composition," "proteinaceous compound," "proteinaceous chain" or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

In certain embodiments the size of the at least one proteinaceous molecule may comprise, but is not limited to, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino acid residues, and any range derivable therein.

As used herein, an "amino acid molecule" refers to any polypeptide, polypeptide derivative, or polypeptide mimetic as would be known to one of ordinary skill in the art. In certain embodiments, the residues of the proteinaceous molecule are sequential, without any non-amino acid molecule interrupting the sequence of amino acid molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid, including but not limited to those shown on Table 1 below.

TABLE 1

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

In certain embodiments the proteinaceous composition comprises at least one protein, polypeptide or peptide. In further embodiments, the proteinaceous composition comprises a biocompatible protein, polypeptide or peptide. As used herein, the term "biocompatible" refers to a substance that produces no significant untoward effects when applied to, or administered to, a given organism according to the methods and amounts described herein. Such untoward or undesirable effects are those such as significant toxicity or adverse immunological reactions.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials, for example. The nucleotide and protein, polypeptide and peptide sequences for various genes have been previously disclosed, and may be found at computerized databases known to those of ordinary skill in the art. Two such databases are the National Center for Biotechnology Information's Genbank and GenPept databases, for example. The coding regions for these known genes may be amplified and/or expressed using the techniques disclosed herein or as would be know to those of ordinary skill in the art. Alternatively, various commercial preparations of proteins, polypeptides and peptides are known to those of skill in the art.

In certain embodiments a proteinaceous compound may be purified. Generally, "purified" will refer to a specific or protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide. Exemplary activities that may be assessed for retention in the purified proteinaceous composition are iron-binding activity and immunoreactivity.

In specific embodiments of the present invention, a polypeptide is labeled, and any detectable label is suitable in the invention. The label may be attached to the polypeptide at the N-terminus, at the C-terminus, or in a side chain of an amino acid residue. One or more labels may be employed. Exemplary labels included radioactive labels, fluorescent labels, colorimetric labels, and so forth. In specific embodiments, the label is covalently attached to the polypeptide.

IV. *E. canis* gp36 and *E. chaffeensis* gp47 Nucleic Acid Compositions

Certain embodiments of the present invention concern an *E. canis* gp36 and/or an *E. chaffeensis* gp47 nucleic acid. For the sake of brevity, the following section will refer to any *E. canis* gp36 and/or *E. chaffeensis* gp47 nucleic acid compositions of the present invention.

In certain aspects, a nucleic acid comprises a wild-type or a mutant nucleic acid. In particular aspects, a nucleic acid encodes for or comprises a transcribed nucleic acid. In other aspects, a nucleic acid comprises a nucleic acid segment, or a biologically functional equivalent thereof. In particular aspects, a nucleic acid encodes a protein, polypeptide, peptide.

The term "nucleic acid" is well known in the art and may be used interchangeably herein with the term "polynucleotide." A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss," a double stranded nucleic acid by the prefix "ds," and a triple stranded nucleic acid by the prefix "ts."

A. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, carboxyalkyl, amino, hydroxyl, halogen (i.e., fluoro, chloro, bromo, or iodo), thiol or alkylthiol moeity. Preferred alkyl (e.g., alkyl, caboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxadenine, a 6-hydroxyaminopurine, a 6-thiopurine, a 4-(6-aminohexyl/cytosine), and the like.

A nucleobase may be comprised in a nucleoside or nucleotide, using any chemical or natural synthesis method described herein or known to one of ordinary skill in the art.

B. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

C. Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

D. Nucleic Acid Analogs

A nucleic acid may comprise, or be composed entirely of, a derivative or analog of a nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids comprising 5-carbon sugar and/or backbone moiety derivatives or analogs, include those in U.S. Pat. No. 5,681,947 which describes oligonucleotides comprising purine derivatives that form triple helixes with and/or prevent expression of dsDNA; U.S. Pat. Nos. 5,652,099 and 5,763,167 which describe nucleic acids incorporating fluorescent analogs of nucleosides found in DNA or RNA, particularly for use as fluorescent nucleic acids probes; U.S. Pat. No. 5,614,617 which describes oligonucleotide analogs with substitutions on pyrimidine rings that possess enhanced nuclease stability; U.S. Pat. Nos. 5,670,663, 5,872,232 and 5,859,221 which describe oligonucleotide analogs with modified 5-carbon sugars (i.e., modified 2'-deoxyfuranosyl moieties) used in nucleic acid detection; U.S. Pat. No. 5,446,137 which describes oligonucleotides comprising at least one 5-carbon sugar moiety substituted at the 4' position with a substituent other than hydrogen that can be used in hybridization assays; U.S. Pat. No. 5,886,165 which describes oligonucleotides with both deoxyribonucleotides with 3'-5' internucleotide linkages and ribonucleotides with 2'-5' internucleotide linkages; U.S. Pat. No. 5,714,606 which describes a modified internucleotide linkage wherein a 3'-position oxygen of the internucleotide linkage is replaced by a carbon to enhance the nuclease resistance of nucleic acids; U.S. Pat. No. 5,672,697 which describes oligonucleotides containing one or more 5' methylene phosphonate internucleotide linkages that enhance nuclease resistance; U.S. Pat. Nos. 5,466,786 and 5,792,847 which describe the linkage of a substituent moeity which may comprise a drug or label to the 2' carbon of an oligonucleotide to provide enhanced nuclease stability and ability to deliver drugs or detection moieties; U.S. Pat. No. 5,223,618 which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967 which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240 which describe oligonucleotides with three or four atom linker moeity replacing phosphodiester backbone moeity used for improved nuclease resistance, cellular uptake and regulating RNA expression; U.S. Pat. No. 5,858,988 which describes hydrophobic carrier agent attached to the 2'-O position of oligonucleotides to enhanced their membrane permeability and stability; U.S. Pat. No. 5,214,136 which describes oligonucleotides conjugaged to anthraquinone at the 5' terminus that possess enhanced hybridization to DNA or RNA; enhanced stability to nucleases; U.S. Pat. No. 5,700,922 which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154 which describes RNA linked to a DNA to form a DNA-RNA hybrid.

E. Polyether and Peptide Nucleic Acids

In certain embodiments, it is contemplated that a nucleic acid comprising a derivative or analog of a nucleoside or nucleotide may be used in the methods and compositions of the invention. A non-limiting example is a "polyether nucleic acid", described in U.S. Pat. No. 5,908,845, incorporated herein by reference. In a polyether nucleic acid, one or more nucleobases are linked to chiral carbon atoms in a polyether backbone.

Another non-limiting example is a "peptide nucleic acid", also known as a "PNA", "peptide-based nucleic acid analog" or "PENAM", described in U.S. Pat. Nos. 5,786,461, 5,891, 625, 5,773,571, 5,766,855, 5,736,336, 5,719,262, 5,714,331, 5,539,082, and WO 92/20702, each of which is incorporated herein by reference. Peptide nucleic acids generally have enhanced sequence specificity, binding properties, and resistance to enzymatic degradation in comparison to molecules such as DNA and RNA (Egholm et al., 1993; PCT/EP/01219). A peptide nucleic acid generally comprises one or more nucleotides or nucleosides that comprise a nucleobase moiety, a nucleobase linker moiety that is not a 5-carbon sugar, and/or a backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

In certain embodiments, a nucleic acid analogue such as a peptide nucleic acid may be used to inhibit nucleic acid amplification, such as in PCR, to reduce false positives and discriminate between single base mutants, as described in U.S. Pat. No. 5,891,625. Other modifications and uses of nucleic acid analogs are known in the art, and are encompassed by the gp36 polynucleotide. In a non-limiting example, U.S. Pat. No. 5,786,461 describes PNAs with amino acid side chains attached to the PNA backbone to enhance solubility of the molecule. In another example, the cellular uptake property of PNAs is increased by attachment of a lipophilic group. U.S. application Ser. No. 117,363 describes several alkylamino moeities used to enhance cellular uptake of a PNA. Another example is described in U.S. Pat. Nos. 5,766,855, 5,719,262, 5,714,331 and 5,736,336, which describe PNAs comprising naturally and non-naturally occurring nucleobases and alkylamine side chains that provide improvements in sequence specificity, solubility and/or binding affinity relative to a naturally occurring nucleic acid.

F. Preparation of Nucleic Acids

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 1989, incorporated herein by reference).

G. Purification of Nucleic Acids

A nucleic acid may be purified on polyacrylamide gels, cesium chloride centrifugation gradients, or by any other means known to one of ordinary skill in the art (see for example, Sambrook et al., 1989, incorporated herein by reference).

In certain aspect, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

H. Nucleic Acid Segments

In certain embodiments, the nucleic acid is a nucleic acid segment. As used herein, the term "nucleic acid segment," are smaller fragments of a nucleic acid, such as for non-limiting example, those that encode only part of the peptide or polypeptide sequence. Thus, a "nucleic acid segment" may comprise any part of a gene sequence, of from about 2 nucleotides to the full length of the peptide or polypeptide encoding region.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be generated:

n to n+y where n is an integer from 1 to the last number of the sequence and y is the length of the nucleic acid segment minus one, where n+y does not exceed the last number of the sequence. Thus, for a 10 mer, the nucleic acid segments correspond to bases 1 to 10, 2 to 11, 3 to 12 . . . and so on. For a 15-mer, the nucleic acid segments correspond to bases 1 to 15, 2 to 16, 3 to 17 . . . and so on. For a 20-mer, the nucleic segments correspond to bases 1 to 20, 2 to 21, 3 to 22 . . . and so on. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

I. Nucleic Acid Complements

The present invention also encompasses a nucleic acid that is complementary to one or more other nucleic acids. In specific embodiments, for example, a nucleic acid is employed for antisense or siRNA purposes, such as to inhibit at least partially expression of a polynucleotide.

In particular embodiments the invention encompasses a nucleic acid or a nucleic acid segment complementary to the sequence set forth herein, for example. A nucleic acid is "complement(s)" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule.

As used herein, the term "complementary" or "complement(s)" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range derivable therein, of the nucleobase sequence is capable of base-pairing with a single or double stranded nucleic acid molecule during hybridization. In certain embodiments, the term "complementary" refers to a nucleic acid that may hybridize to another nucleic acid strand or duplex in stringent conditions, as would be understood by one of ordinary skill in the art.

In certain embodiments, a "partly complementary" nucleic acid comprises a sequence that may hybridize in low stringency conditions to a single or double stranded nucleic acid, or contains a sequence in which less than about 70% of the nucleobase sequence is capable of base-pairing with a single or double stranded nucleic acid molecule during hybridization.

J. Hybridization

As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl, for example, at temperatures of about 50° C. to about 70° C. or, for example, wherein said stringent conditions are hybridization at 50-65° C., 5×SSPC, 50% formamide; wash 50-65° C., 5×SSPC; or wash at 60° C., 0.5×SSC, 0.1% SDS. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

V. Nucleic Acid-Based Expression Systems

In particular embodiments, the present invention concerns a polynucleotide that encodes an immunoreactive Ehrlichiae polypeptide, and also includes delivering the polynucleotide encoding the polypeptide, or encoded product thereof, to an individual in need thereof, such as an individual infected with *Ehrlichia* and/or an individual susceptible to being infected with *Ehrlichia*. For the sake of brevity, the following section will refer to any *E. canis* gp36 and/or *E. chaffeensis* gp47 nucleic acid compositions and/or nucleic acid-based expression system of the present invention.

The present invention is directed toward substantially pure and/or isolated DNA sequence encoding an immunoreactive *Ehrlichia* composition. Generally, the encoded protein comprises an N-terminal sequence, which may be cleaved after post-translational modification resulting in the production of mature protein.

It is well-known in the art that because of the degeneracy of the genetic code (i.e., for most amino acids, more than one nucleotide triplet (codon) codes for a single amino acid), different nucleotide sequences can code for a particular amino acid, or polypeptide. Thus, the polynucleotide sequences of the subject invention include any of the provided exemplary sequences or a degenerate variant of such a sequence, for example. In particular aspects of the invention, a degenerate variant comprises a sequence that is not identical to a sequence of the invention but that still retains one or more properties of a sequence of the invention.

As used herein, "substantially pure DNA" means DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or that exists as a separate molecule (e.g., a cDNA or a genomic or cDNA fragment produced by polymerase chain reaction (PCR) or restriction endonuclease digestion) independent of other sequences. It also includes a recombinant DNA, which is part of a hybrid gene encoding additional polypeptide sequence, e.g., a fusion protein.

The present invention is further directed to an expression vector comprising a polynucleotide encoding an immunoreactive Ehrlichiae composition and capable of expressing the polynucleotide when the vector is introduced into a cell. In specific embodiments, the vector comprises in operable linkage the following: a) an origin of replication; b) a promoter; and c) a DNA sequence coding for the protein.

As used herein "vector" may be defined as a replicable nucleic acid construct, e.g., a plasmid or viral nucleic acid. Vectors may be used to amplify and/or express nucleic acid encoding an immunoreactive composition of Ehrlichiae. An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences that control the termination of transcription and translation, for example. Methods that are well-known to those skilled in the art can be used to construct expression vectors comprising appropriate transcriptional and translational control signals. See for example, the techniques described in Sambrook et al., 1989, Molecular Cloning: A Laboratory Manual (2nd Ed.), Cold Spring Harbor Press, N.Y. A polynucleotide sequence to be expressed and its transcription control sequences are defined as being "operably linked" if the transcription control sequences effectively control the transcription of the polynucleotide sequence. Vectors of the invention include, but are not limited to, plasmid vectors and viral vectors. Preferred viral vectors of the invention are those derived from retroviruses, adenovirus, adeno-associated virus, SV40 virus, or herpes viruses, for example.

In general, expression vectors comprise promoter sequences that facilitate the efficient transcription of the polynucleotide to be expressed, are used in connection with a host cell. As used herein, the term "host" is meant to include not only prokaryotes but also eukaryotes, such as yeast, plant and animal cells. A recombinant polynucleotide that encodes an immunoreactive composition of Ehrlichiae of the present invention can be used to transform a host using any of the techniques commonly known to those of ordinary skill in the art. Prokaryotic hosts may include *E. coli, S. tymphimurium, Serratia marcescens* and *Bacillus subtilis*. Eukaryotic hosts include yeasts, such as *Pichia pastoris*, mammalian cells and insect cells.

The following description concerns exemplary elements, reagents, and methods for polynucleotides and nucleic acid delivery of an *Ehrlichia* polynucleotide.

A. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the beta lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell, organelle, cell type, tissue, organ, or organism chosen for expression. Those of skill in the art of molecular biology generally know the use of promoters, enhancers, and cell type combinations for protein expression, (see, for example Sambrook et al., 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The promoter may be one suitable for use in a prokaryotic cell, a eukaryotic cell, or both. Additionally any promoter/enhancer combination (as per, for example, the Eukaryotic Promoter Data Base EPDB) could also be used to drive expression. Use of a T3, T7 or SP6 cytoplasmic expression system is one possible embodiment.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

9. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEMTM 11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S transferase (GST) soluble fusion proteins for later purification and separation or cleavage. Other suitable fusion proteins are those with beta galactosidase, ubiquitin, and the like.

Bacterial host cells, for example, E. coli, comprising the expression vector are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

10. Viral Vectors

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). Components of the present invention may comprise a viral vector that encode one or more compositions or other components such as, for example, an immunomodulator or adjuvant. Non-limiting examples of virus vectors that may be used to deliver a nucleic acid of the present invention are described below.

a. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

b. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno associated virus (AAV) is an attractive vector system for use in the compositions of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

c. Retroviral Vectors

Retroviruses have useful as delivery vectors due to their ability to integrate their genes into the host genome, transferring a large amount of foreign genetic material, infecting a broad spectrum of species and cell types and of being packaged in special cell lines (Miller, 1992).

In order to construct a retroviral vector, a nucleic acid (e.g., one encoding a composition of interest) is inserted into the viral genome in the place of certain viral sequences to produce a virus that is replication defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

d. Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

e. Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

11. Vector Delivery and Cell Transformation

Suitable methods for Ehrlichial nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); by PEG mediated transformation of protoplasts (Omirulleh et al., 1993; U.S. Pat. Nos. 4,684,611 and 4,952,500, each incorporated herein by reference); by desiccation/inhibition mediated DNA uptake (Potrykus et al., 1985), and any combination of such methods. Through the application of techniques such as these, organelle(s), cell(s), tissue(s) or organism(s) may be stably or transiently transformed.

a. Ex Vivo Transformation

Methods for tranfecting vascular cells and tissues removed from an organism in an ex vivo setting are known to those of skill in the art. For example, canine endothelial cells have been genetically altered by retrovial gene transfer in vitro and transplanted into a canine (Wilson et al., 1989). In another example, yucatan minipig endothelial cells were transfected by retrovirus in vitro and transplanted into an artery using a double-balloon catheter (Nabel et al., 1989). Thus, it is contemplated that cells or tissues may be removed and transfected ex vivo using the nucleic acids of the present invention. In particular aspects, the transplanted cells or tissues may be placed into an organism. In preferred facets, a nucleic acid is expressed in the transplanted cells or tissues.

b. Injection

In certain embodiments, a nucleic acid may be delivered to an organelle, a cell, a tissue or an organism via one or more injections (i.e., a needle injection), such as, for example, subcutaneously, intradermally, intramuscularly, intervenously, intraperitoneally, etc. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into *Xenopus* oocytes (Harland and Weintraub, 1985). The amount of composition used may vary upon the nature of the antigen as well as the organelle, cell, tissue or organism used c. Electroporation In certain embodiments of the present invention, a nucleic acid is introduced into an organelle, a cell, a tissue or an organism via electroporation. Electroporation involves the exposure of a suspension of cells and DNA to a high voltage electric discharge. In some variants of this method, certain cell wall degrading enzymes, such as pectin degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre B lymphocytes have been transfected with human kappa immunoglobulin genes (Potter et al., 1984), and rat hepatocytes have been transfected with the chloramphenicol acetyltransferase gene (Tur Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon derived protoplasts is described by Dhir and Widholm in International Patent Application No. WO 9217598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

d. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV 1, BHK, NIH3T3 and HeLa cells were transfected with a neomycin marker gene (Chen and Okayama, 1987), and rat hepatocytes were transfected with a variety of marker genes (Rippe et al., 1990).

e. DEAE Dextran

In another embodiment, a nucleic acid is delivered into a cell using DEAE dextran followed by polyethylene glycol. In this manner, reporter plasmids were introduced into mouse myeloma and erythroleukemia cells (Gopal, 1985).

f. Sonication Loading

Additional embodiments of the present invention include the introduction of a nucleic acid by direct sonic loading. LTK fibroblasts have been transfected with the thymidine kinase gene by sonication loading (Fechheimer et al., 1987).

g. Liposome-Mediated Transfection

In a further embodiment of the invention, an Ehrlichial nucleic acid may be comprised with a lipid complex such as, for example, comprised in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome encapsulated DNA (Kaneda et al., 1989). In other embodiments, a liposome may be complexed or employed in conjunction with nuclear non histone chromosomal proteins (HMG 1) (Kato et al., 1991). In yet further embodiments, a liposome may be complexed or employed in conjunction with both HVJ and HMG 1. In other embodiments, a delivery vehicle may comprise a ligand and a liposome.

h. Receptor-Mediated Transfection

Still further, a nucleic acid may be delivered to a target cell via receptor mediated delivery vehicles. These take advantage of the selective uptake of macromolecules by receptor-mediated endocytosis that will be occurring in a target cell. In view of the cell type specific distribution of various receptors, this delivery method adds another degree of specificity to the present invention.

Certain receptor mediated gene targeting vehicles comprise a cell receptor specific ligand and a nucleic acid binding agent. Others comprise a cell receptor specific ligand to which the nucleic acid to be delivered has been operatively attached. Several ligands have been used for receptor mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell specific binding. For example, lactosyl ceramide, a galactose terminal asialganglioside, have been incorporated into liposomes and observed an increase in the uptake of the insulin gene by hepatocytes (Nicolau et al., 1987). It is contemplated that the tissue specific transforming constructs of the present invention can be specifically delivered into a target cell in a similar manner.

i. Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA coated microprojectiles to a high velocity allowing them to pierce cell membranes and enter cells without killing them (Klein et al., 1987). There are a wide variety of microprojectile bombardment techniques known in the art, many of which are applicable to the invention.

Microprojectile bombardment may be used to transform various cell(s), tissue(s) or organism(s), such as for example any plant species. Examples of species which have been transformed by microprojectile bombardment include monocot species such as maize (PCT Application WO 95/06128), barley (Ritala et al., 1994; Hensgens et al., 1993), wheat (U.S. Pat. No. 5,563,055, incorporated herein by reference), rice (Hensgens et al., 1993), oat (Torbet et al., 1995; Torbet et al., 1998), rye (Hensgens et al., 1993), sugarcane (Bower et al., 1992), and sorghum (Casas et al., 1993; Hagio et al., 1991); as well as a number of dicots including tobacco (Tomes et al., 1990; Buising and Benbow, 1994), soybean (U.S. Pat. No. 5,322,783, incorporated herein by reference), sunflower (Knittel et al. 1994), peanut (Singsit et al., 1997), cotton (McCabe and Martinell, 1993), tomato (VanEck et al. 1995), and legumes in general (U.S. Pat. No. 5,563,055, incorporated herein by reference).

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into a cell (e.g., a plant cell) by acceleration is the Biolistics Particle Delivery System, which can be used to propel particles coated with DNA or cells through a screen, such as a stainless steel or Nytex screen, onto a filter surface covered with cells, such as for example, a monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

12. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

A tissue may comprise a host cell or cells to be transformed with a composition of the invention. The tissue may be part or separated from an organism. In certain embodiments, a tissue may comprise, but is not limited to, adipocytes, alveolar, ameloblasts, axon, basal cells, blood (e.g., lymphocytes), blood vessel, bone, bone marrow, brain, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, skin, small intestine, spleen, stem cells, stomach, testes, anthers, ascite tissue, cobs, ears, flowers, husks, kernels, leaves, meristematic cells, pollen, root tips, roots, silk, stalks, and all cancers thereof.

In certain embodiments, the host cell or tissue may be comprised in at least one organism. In certain embodiments, the organism may be, but is not limited to, a prokayote (e.g., a eubacteria, an archaea) or an eukaryote, as would be understood by one of ordinary skill in the art (see, for example, webpage http://phylogeny.arizona.edu/tree/phylogeny.html).

Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Cell types available for vector replication and/or expression include, but are not limited to, bacteria, such as *E. coli* (e.g., *E. coli* strain RR1, *E. coli* LE392, *E. coli* B, *E. coli* X 1776 (ATCC No. 31537) as well as *E. coli* W3110 (F, lambda, prototrophic, ATCC No. 273325), DH5α, JM109, and KC8, bacilli such as *Bacillus subtilis*; and other enterobacteriaceae such as *Salmonella typhimurium, Serratia marcescens*, various *Pseudomonas* specie, as well as a number of commercially available bacterial hosts such as SURE® Competent Cells and SOLOPACK Gold Cells (STRATAGENE®, La Jolla). In certain embodiments, bacterial cells such as *E. coli* LE392 are particularly contemplated as host cells for phage viruses.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

13. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

It is contemplated that the proteins, polypeptides or peptides produced by the methods of the invention may be "overexpressed", i.e., expressed in increased levels relative to its natural expression in cells. Such overexpression may be assessed by a variety of methods, including radio labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific protein, polypeptides or peptides in relation to the other proteins produced by the host cell and, e.g., visible on a gel.

In some embodiments, the expressed proteinaceous sequence forms an inclusion body in the host cell, the host cells are lysed, for example, by disruption in a cell homogenizer, washed and/or centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed. Inclusion bodies may be solubilized in solutions containing high concentrations of urea (e.g. 8M) or chaotropic agents such as guanidine hydrochloride in the presence of reducing agents, such as beta mercaptoethanol or DTT (dithiothreitol), and refolded into a more desirable conformation, as would be known to one of ordinary skill in the art.

VI. Immunological Compositions

In particular embodiments of the invention, immunological compositions are employed. For the sake of brevity, the following section will refer to any *E. canis* gp36 or *E. chaffeensis* gp47 immunological compositions of the present invention, such as are described elsewhere herein as only exemplary embodiments. For example, the compositions may include all or part of an *E. canis* gp36 SEQ ID NO:22, SEQ ID NO:37, SEQ ID NO:38, or SEQ ID NO:39. Also, the compositions may include all or part of an *E. chaffeensis* gp47 SEQ ID NO:23, SEQ ID NO:24, SEQ ID NO:40, or SEQ ID NO:41, for example. Antibodies may be utilized to bind an antigen, thereby rendering the molecule at least partially ineffective for its activity, for example. In other embodiments, antibodies to the antigen are employed in diagnostic aspects of the invention, such as for detecting the presence of the antigen from a sample. Exemplary samples may be from an animal suspected of having *E. canis* or *E. chaffeensis* infection, from an animal susceptible to *E. canis* or *E. chaffeensis* infection, or from an animal that has an *E. canis* or *E. chaffeensis* infection. Exemplary samples may be obtained from blood, serum, cerebrospinal fluid, urine, feces, cheek scrapings, nipple aspirate, and so forth.

Purified immunoreactive compositions or antigenic fragments of the immunoreactive compositions can be used to generate new antibodies or to test existing antibodies (e.g., as positive controls in a diagnostic assay) by employing standard protocols known to those skilled in the art.

As is well known in the art, immunogenicity to a particular immunogen can be enhanced by the use of non-specific stimulators of the immune response known as adjuvants. Exemplary and preferred adjuvants include complete BCG, Detox, (RIBI, Immunochem Research Inc.), ISCOMS and aluminum hydroxide adjuvant (Superphos, Biosector).

Included in this invention are polyclonal antisera generated by using the immunoreactive composition or a fragment of the immunoreactive composition as an immunogen in, e.g., rabbits. Standard protocols for monoclonal and polyclonal antibody production known to those skilled in this art are employed. The monoclonal antibodies generated by this procedure can be screened for the ability to identify recombinant *Ehrlichia* cDNA clones, and to distinguish them from known cDNA clones, for example.

The invention encompasses not only an intact monoclonal antibody, but also an immunologically-active antibody fragment, e.g., a Fab or (Fab)2 fragment; an engineered single chain scFv molecule; or a chimeric molecule, e.g., an antibody which contains the binding specificity of one antibody, e.g., of murine origin, and the remaining portions of another antibody, e.g., of human origin.

In one embodiment, the antibody, or fragment thereof, may be linked to a toxin or to a detectable label, e.g. a radioactive label, non-radioactive isotopic label, fluorescent label, chemiluminescent label, paramagnetic label, enzyme label or colorimetric label. Examples of suitable toxins include diphtheria toxin, *Pseudomonas* exotoxin A, ricin, and cholera toxin. Examples of suitable enzyme labels include malate hydrogenase, staphylococcal nuclease, delta-5-steroid isomerase, alcohol dehydrogenase, alpha glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholinesterase, etc. Examples of suitable radioisotopic labels include $^{3}H$, $^{125}I$, $^{131}I$, $^{32}P$, $^{35}S$, $^{14}C$, etc.

Paramagnetic isotopes for purposes of in vivo diagnosis can also be used according to the methods of this invention. There are numerous examples of elements that are useful in magnetic resonance imaging. For discussions on in vivo nuclear magnetic resonance imaging, see, for example, Schaefer et al., (1989) JACC 14, 472-480; Shreve et al., (1986) Magn. Reson. Med. 3, 336-340; Wolf, G. L., (1984) Physiol. Chem. Phys. Med. NMR 16, 93-95; Wesby et al., (1984) Physiol. Chem. Phys. Med. NMR 16, 145-155; Runge et al., (1984) Invest. Radiol. 19, 408-415. Examples of suitable fluorescent labels include a fluorescein label, an isothiocyalate label, a rhodamine label, a phycoerythrin label, a phycocyanin label, an allophycocyanin label, an opthaldehyde label, a fluorescamine label, etc. Examples of chemiluminiscent labels include a luminal label, an isoluminal label, an aromatic acridinium ester label, a luciferin label, a luciferase label, an aequorin label, etc.

Those of ordinary skill in the art will know of these and other suitable labels, which may be employed in accordance with the present invention. The binding of these labels to antibodies or fragments thereof can be accomplished using standard techniques commonly known to those of ordinary skill in the art. Typical techniques are described by Kennedy et al., (1976) Clin. Chim. Acta 70, 1-31; and Schurs et al., (1977) Clin. Chim. Acta 81, 1-40. Coupling techniques mentioned in the later are the glutaraldehyde method, the periodate method, the dimaleimide method, the maleimido-benzyl-N-hydroxy-succinimde ester method. All of these methods are incorporated by reference herein.

B. Antibodies

In certain aspects of the invention, one or more antibodies may be produced to the expressed gp36 or gp47. These antibodies may be used in various diagnostic and/or therapeutic applications described herein.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

"Mini-antibodies" or "minibodies" are also contemplated for use with the present invention. Minibodies are sFv polypeptide chains which include oligomerization domains at their C-termini, separated from the sFv by a hinge region. Pack et al. (1992) Biochem 31:1579-1584. The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992) Biochem 31:1579-1584; Cumber et al. (1992) J Immunology 149B:120-126.

Antibody-like binding peptidomimetics are also contemplated in the present invention. Liu et al. Cell Mol Biol (Noisy-le-grand). 2003 March; 49(2):209-16 describe "antibody like binding peptidomimetics" (ABiPs), which are peptides that act as pared-down antibodies and have certain advantages of longer serum half-life as well as less cumbersome synthesis methods.

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

However, "humanized" antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". A "humanized antibody" is an antibody comprising a humanized light chain and a humanized heavy chain immunoglobulin.

C. Exemplary Methods for Generating Monoclonal Antibodies

Exemplary methods for generating monoclonal antibodies (MAbs) generally begin along the same lines as those for preparing polyclonal antibodies. Briefly, a polyclonal antibody is prepared by immunizing an animal with a LEE or CEE composition in accordance with the present invention and collecting antisera from that immunized animal.

A wide range of animal species can be used for the production of antisera. Typically the animal used for production of antisera is a rabbit, a mouse, a rat, a hamster, a guinea pig or a goat. The choice of animal may be decided upon the ease of manipulation, costs or the desired amount of sera, as would be known to one of skill in the art. Antibodies of the invention can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750,172, and 5,741,957.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, chemokines, cofactors, toxins, plasmodia, synthetic compositions or LEEs or CEEs encoding such adjuvants.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m2) (Johnson/Mead, NJ), cytokines such as γ-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen including but not limited to subcutaneous, intramuscular, intradermal, intraepidermal, intravenous and intraperitoneal. The production of polyclonal antibodies may be monitored by sampling blood of the immunized animal at various points following immunization.

A second, booster dose (e.g., provided in an injection), may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60 61), but mice are preferred, with the BALB/c mouse being most preferred as this is most routinely used and generally gives a higher percentage of stable fusions.

The animals are injected with antigen, generally as described above. The antigen may be mixed with adjuvant, such as Freund's complete or incomplete adjuvant. Booster administrations with the same antigen or DNA encoding the antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma producing fusion procedures preferably are non antibody producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65 66, 1986; Campbell, pp. 75 83, 1984). cites). For example, where the immunized animal is a mouse, one may use P3 X63/Ag8, X63 Ag8.653, NS1/1.Ag 4 1, Sp210 Ag14, FO, NSO/U, MPC 11, MPC11 X45 GTG 1.7 and S194/5XX0 Bul; for rats, one may use R210.RCY3, Y3 Ag 1.2.3, IR983F and 4B210; and U 266, GM1500 GRG2, LICR LON HMy2 and UC729 6 are all useful in connection with human cell fusions. See Yoo et al., J Immunol Methods. 2002 Mar. 1; 261(1-2):1-20, for a discussion of myeloma expression systems.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8 azaguanine resistant mouse murine myeloma SP2/0 non producer cell line.

Methods for generating hybrids of antibody producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al., (1977). The use of electrically induced fusion methods is also appropriate (Goding pp. 71 74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody producing cell lines, which clones can then be propagated indefinitely to provide MAbs. The cell lines may be exploited for MAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. Second, the individual cell lines could be cultured in vitro, where the MAbs are naturally secreted into the culture medium from which they can be readily obtained in high concentrations.

Further, expression of antibodies of the invention (or other moieties therefrom) from production cell lines can be enhanced using a number of known techniques. For example, the glutamine synthetase and DHFR gene expression systems are common approaches for enhancing expression under certain conditions. High expressing cell clones can be identified using conventional techniques, such as limited dilution cloning and Microdrop technology. The GS system is discussed in whole or part in connection with European Patent Nos. 0 216 846, 0 256 055, and 0 323 997 and European Patent Application No. 89303964.4.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach may be used to generate monoclonals. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies. In another example, LEEs or CEEs can be used to produce antigens in vitro with a cell free system. These can be used as targets for scanning single chain antibody libraries. This would enable many different antibodies to be identified very quickly without the use of animals.

Another embodiment of the invention for producing antibodies according to the present invention is found in U.S. Pat. No. 6,091,001, which describes methods to produce a cell expressing an antibody from a genomic sequence of the cell comprising a modified immunoglobulin locus using Cre-mediated site-specific recombination is disclosed. The method involves first transfecting an antibody-producing cell with a homology-targeting vector comprising a lox site and a targeting sequence homologous to a first DNA sequence adjacent to the region of the immunoglobulin loci of the genomic sequence which is to be converted to a modified region, so the first lox site is inserted into the genomic sequence via site-specific homologous recombination. Then the cell is transfected with a lox-targeting vector comprising a second lox site suitable for Cre-mediated recombination with the integrated lox site and a modifying sequence to convert the region of the immunoglobulin loci to the modified region. This conversion is performed by interacting the lox sites with Cre in vivo, so that the modifying sequence inserts into the genomic sequence via Cre-mediated site-specific recombination of the lox sites.

Alternatively, monoclonal antibody fragments encompassed by the present invention can be synthesized using an automated peptide synthesizer, or by expression of full-length gene or of gene fragments in E. coli.

D. Antibody Conjugates

The present invention further provides antibodies against gp36 proteins, polypeptides and peptides, generally of the monoclonal type, that are linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radio-labeled nucleotides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Any antibody of sufficient selectivity, specificity or affinity may be employed as the basis for an antibody conjugate. Such properties may be evaluated using conventional immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell co-receptor CD4 and the HIV-1 envelope (Sasso et al., 1989; Shorki et al., 1991; Silvermann et al., 1995; Cleary et al., 1994; Lenert et al., 1990; Berberian et al., 1993; Kreier et al., 1991). In addition, the variable domain is involved in antibody self-binding (Kang et al., 1988), and contains epitopes (idiotopes) recognized by anti-antibodies (Kohler et al., 1989).

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. Another such example is the formation of a conjugate comprising an antibody linked to a cytotoxic or anti cellular agent, and may be termed "immunotoxins".

Antibody conjugates are generally preferred for use as diagnostic agents. Antibody diagnostics generally fall within two classes, those for use in in vitro diagnostics, such as in a variety of immunoassays, and/or those for use in vivo diagnostic protocols, generally known as "antibody directed imaging".

Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium 186, rhenium 188, $^{75}$selenium, $^{35}$sulphur, technicium99m and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium99m by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

In another embodiment of the invention, the anti-gp36 antibodies are linked to semiconductor nanocrystals such as those described in U.S. Pat. Nos. 6,048,616; 5,990,479; 5,690,807; 5,505,928; 5,262,357 (all of which are incorporated herein in their entireties); as well as PCT Publication No. 99/26299 (published May 27, 1999). In particular, exemplary materials for use as semiconductor nanocrystals in the biological and chemical assays of the present invention include, but are not limited to those described above, including group II-VI, III-V and group IV semiconductors such as ZnS, ZnSe, ZnTe, CdS, CdSe, CdTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlS, AlP, AlSb, PbS, PbSe, Ge and Si and ternary and quaternary mixtures thereof. Methods for linking semiconductor nanocrystals to antibodies are described in U.S. Pat. Nos. 6,630,307 and 6,274,323.

E. Immunodetection Methods

In still further embodiments, the present invention concerns immunodetection methods for binding, purifying, removing, quantifying and/or otherwise generally detecting biological components such as immunoreactive polypeptides. The antibodies prepared in accordance with the present invention may be employed to detect wild type and/or mutant proteins, polypeptides and/or peptides. The use of wild-type and/or mutant antibodies is contemplated. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle M H and Ben-Zeev O, 1999; Gulbis B and Galand P, 1993; De Jager R et al., 1993; and Nakamura et al., 1987, each incorporated herein by reference.

In general, the immunobinding methods include obtaining a sample suspected of comprising protein, polypeptide and/or peptide, and contacting the sample with a first anti-gp36 (or gp47) antibody in accordance with the present invention, as the case may be, under conditions effective to allow the formation of immunocomplexes.

These methods include methods for purifying wild type and/or mutant proteins, polypeptides and/or peptides as may be employed in purifying wild type and/or mutant proteins, polypeptides and/or peptides from patients' samples and/or for purifying recombinantly expressed wild type or mutant proteins, polypeptides and/or peptides. In these instances, the antibody removes the antigenic wild type and/or mutant protein, polypeptide and/or peptide component from a sample. The antibody will preferably be linked to a solid support, such as in the form of a column matrix, and the sample suspected of containing the wild type or mutant protein antigenic component will be applied to the immobilized antibody. The unwanted components will be washed from the column, leaving the antigen immunocomplexed to the immobilized antibody, which wild type or mutant protein antigen is then collected by removing the wild type or mutant protein and/or peptide from the column.

The immunobinding methods also include methods for detecting and quantifying the amount of a wild type or mutant protein reactive component in a sample and the detection and quantification of any immune complexes formed during the binding process. Here, one would obtain a sample suspected of comprising a wild type or mutant protein and/or peptide or suspected of comprising an *E. canis* organism, and contact the sample with an antibody against wild type or mutant, and then detect and quantify the amount of immune complexes formed under the specific conditions.

In terms of antigen detection, the biological sample analyzed may be any sample that is suspected of containing a wild type or mutant protein-specific antigen, such as a specimen, a homogenized tissue extract, a cell, separated and/or purified forms of any of the above wild type or mutant protein-containing compositions, or even any biological fluid that comes into contact with an *E. canis* organism upon infection.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any protein antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. Patents concerning the use of such labels include U.S. Pat. Nos. 3,817,837; 3,850,752; 3,939, 350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

The immunodetection methods of the present invention have evident utility in the diagnosis and prognosis of conditions such as various forms of hyperproliferative diseases, such as cancer, including leukemia, for example. Here, a biological and/or clinical sample suspected of containing a wild type or mutant protein, polypeptide, peptide and/or mutant is used. However, these embodiments also have applications to non-clinical samples, such as in the titering of antigen or antibody samples, for example in the selection of hybridomas.

F. ELISAs

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, the antibodies of the invention are immobilized onto a selected surface exhibiting protein affinity, such as a well in a polystyrene microtiter plate. Then, a test composition suspected of containing the wild type and/or mutant protein antigen, such as a clinical sample, is added to the wells. After binding and/or washing to remove non-specifically bound immune complexes, the bound wild type and/or mutant protein antigen may be detected. Detection is generally achieved by the addition of another antibody that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the wild type and/or mutant protein antigen are immobilized onto the well surface and/or then contacted with the antibodies of the invention. After binding and/or washing to remove non-specifically bound immune complexes, the bound antibodies are detected. Where the initial antibodies are linked to a detectable label, the immune complexes may be detected directly. Again, the immune complexes may be detected using a second antibody that has binding affinity for the first antibody, with the second antibody being linked to a detectable label.

Another ELISA in which the wild type and/or mutant proteins, polypeptides and/or peptides are immobilized, involves the use of antibody competition in the detection. In this ELISA, labeled antibodies against wild type or mutant protein are added to the wells, allowed to bind, and/or detected by means of their label. The amount of wild type or mutant protein antigen in an unknown sample is then determined by mixing the sample with the labeled antibodies against wild type and/or mutant before and/or during incubation with coated wells. The presence of wild type and/or mutant protein in the sample acts to reduce the amount of antibody against wild type or mutant protein available for binding to the well and thus reduces the ultimate signal. This is also appropriate for detecting antibodies against wild type or mutant protein in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

G. Immunohistochemistry

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in 70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

H. Immunoelectron Microscopy

The antibodies of the present invention may also be used in conjunction with electron microscopy to identify intracellular tissue components. Briefly, an electron-dense label is conjugated directly or indirectly to the antibody. Examples of electron-dense labels according to the invention are ferritin and gold. The electron-dense label absorbs electrons and can be visualized by the electron microscope.

I. Immunodetection Kits

In still further embodiments, the present invention concerns immunodetection kits for use with the immunodetection methods described above. As the antibodies are generally used to detect wild type and/or mutant proteins, polypeptides and/or peptides, the antibodies will preferably be included in the kit. However, kits including both such components may be provided. The immunodetection kits will thus comprise, in suitable container means, a first antibody that binds to a wild type and/or mutant protein, polypeptide and/or peptide, and/or optionally, an immunodetection reagent and/or further optionally, a wild type and/or mutant protein, polypeptide and/or peptide.

In preferred embodiments, monoclonal antibodies will be used. In certain embodiments, the first antibody that binds to the wild type and/or mutant protein, polypeptide and/or peptide may be pre-bound to a solid support, such as a column matrix and/or well of a microtitre plate.

The immunodetection reagents of the kit may take any one of a variety of forms, including those detectable labels that are associated with and/or linked to the given antibody. Detectable labels that are associated with and/or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and/or all such labels may be employed in connection with the present invention.

The kits may further comprise a suitably aliquoted composition of the wild type and/or mutant protein, polypeptide and/or polypeptide, whether labeled and/or unlabeled, as may be used to prepare a standard curve for a detection assay. The kits may contain antibody-label conjugates either in fully conjugated form, in the form of intermediates, and/or as separate moieties to be conjugated by the user of the kit. The components of the kits may be packaged either in aqueous media and/or in lyophilized form.

The container means of the kits will be suitable housed and will generally include at least one vial, test tube, flask, bottle, syringe and/or other container means, into which the antibody may be placed, and/or preferably, suitably aliquoted. Where wild type and/or mutant gp36 protein, polypeptide and/or peptide, and/or a second and/or third binding ligand and/or additional component is provided, the kit will also generally contain a second, third and/or other additional container into which this ligand and/or component may be placed. The kits of the present invention will also typically include a means for containing the antibody, antigen, and/or any other reagent containers in close confinement for commercial sale. Such containers may include injection and/or blow-molded plastic containers into which the desired vials are retained.

VII. Pharmaceutical Preparations

It is also contemplated that pharmaceutical compositions may be prepared using the novel compositions of the present invention. In such a case, the pharmaceutical composition comprises the novel active composition of the present invention and a pharmaceutically acceptable carrier. A person having ordinary skill in this art would readily be able to determine, without undue experimentation, the appropriate dosages and routes of administration of the active component of the present invention.

The phrase "pharmaceutically acceptable" refers to molecular entities and compositions that do not produce an allergic or similar untoward reaction when administered to a subject. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In general, a pharmaceutical composition of the present invention may comprise an *E. canis* gp36 polypeptide, polynucleotide, or antibody and/or an *E. chaffeensis* gp47 polypeptide, polynucleotide, or antibody, and/or mixtures thereof.

A protein may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids such as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media, which can be employed, will be known to those of skill in the art in light of present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Pharmaceutical compositions of the present invention comprise an effective amount of one or more agents that target a polypeptide or the secretion thereof or additional agent dissolved or dispersed in a pharmaceutically acceptable carrier. The phrases "pharmaceutical," "pharmaceutically acceptable," or "pharmacologically acceptable" refers to molecular entities and compositions that do not produce an adverse, allergic or other untoward reaction when administered to an animal, such as, for example, a human, as appropriate. The preparation of a pharmaceutical composition that contains at least one agent that targets the polypeptide or the secretion thereof and/or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The invention may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the composition is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations that are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

VIII. Exemplary Kits of the Invention

In particular embodiments of the invention, there is a kit housed in a suitable container. The kit may be suitable for diagnosis, treatment, and/or protection for an individual from *Ehrlichia*, such as *Ehrlichia canis*, *Ehrlichia chaffeensis*, or both. In particular embodiments, the kit comprises in a suitable container an agent that targets an *E. canis* gp36 antigen or an *E. chaffeensis* gp47 antigen. The agent may be an antibody, a small molecule, a polynucleotide, a polypeptide, a peptide, or a mixture thereof. The agent may be provided in the kit in a suitable form, such as sterile, lyophilized, or both, for example. In particular embodiments, the kit comprises one or more of the following: 1) an antibody against one or more of SEQ ID NO:22, SEQ ID NO:37, SEQ ID NO:38, or SEQ ID NO:39 (for *E. canis*); 2) an antibody against one or more of SEQ ID NO:23, SEQ ID NO:24, SEQ ID NO:40, or SEQ ID NO:41 (for *E. chaffeensis*); and/or 3) SEQ ID NO:22, SEQ ID NO:37, SEQ ID NO:38, or SEQ ID NO:39 (for *E. canis*) and/or SEQ ID NO:23, SEQ ID NO:24, SEQ ID NO:40, or SEQ ID NO:41 (for *E. chaffeensis*) and/or related proteins thereof. Other *E. canis* gp36-related or *E. chaffeensis* gp47-related immunogenic-related compositions (including polypeptides, peptides, or antibodies) not specifically presented herein may also be included.

The kit may further comprise one or more apparatuses for delivery of a composition to an individual in need thereof. The apparatuses may include a syringe, eye dropper, needle, biopsy tool, scoopula, catheter, and so forth, for example.

In embodiments wherein the kit is employed for a diagnostic purpose, the kit may further provide one or more detection compositions or apparatuses for identifying an *E. canis* gp36 antigen, an *E. chaffeensis* gp47 antigen, or both. Such an embodiment may employ a detectable label, such as for an antibody, for example, and the label may be fluorescent, chemiluminescent, or colorimetric, for example.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1

Exemplary Materials and Methods

The following descriptions provide merely exemplary materials and methods utilized in the invention.

Ehrlichiae and Purification.

*E. canis* (Jake, Oklahoma, and Demon isolates) and *E. chaffeensis* (Arkansas and Sapulpa isolates) were propogated as previously described (McBride et al., 2001). Ehrlichiae were purified by size exclusion over Sephacryl S-1000 (Amersham Biosciences, Piscataway, N.J.) as previously described (Rikihisa et al., 1992). The fraction containing bacteria was frozen and utilized as an antigen and DNA source.

Construction and Screening of the *E. canis* Genomic Library.

An *E. canis* HpaII genomic library was constructed and screened as previously described (McBride et al., 2001).

DNA Sequencing.

Library inserts, plasmids, and PCR products were sequenced with an ABI Prism 377XL DNA Sequencer (Perkin-Elmer Applied Biosystems, Foster City, Calif.) at the University of Texas Medical Branch Protein Chemistry Core Laboratory.

Glycoprotein Polynucleotide Analysis.

Nucleic and amino acid alignments were performed with MegAlign (Lasergene v5.08, DNAstar, Madison, Wis.). The gp36 and gp47 protein sequences were tested for potential mucin-type O-linked glycosylation on serines and threonines with the computational algorithm NetOGlyc (Julenius et al., 2005). The tandem repeats of the genes encoding gp36 of *E. canis* strains Jake, Oklahoma, and Demon; gp47 of *E. chaffeensis* strains Arkansas and Sapulpa; mucin-like proteins of *E. ruminantium* strains Highway (AF308673; SEQ ID NO:1, at least part of which encodes AAL08844 (SEQ ID NO:31)), Welgevonden (the genome is provided in GenBank Accession No. CR767821; an exemplary mucin-like protein thereof is provided in GenBank Accession No. CAI26602 (SEQ ID NO:29)), and Gardel (the genome is provided in GenBank Accession No. CR925677; an exemplary mucin-like protein thereof is provided in GenBank Accession No. CAI27556 (SEQ ID NO:30)); gp140 of *E. canis* strain Jake (AF112369; SEQ ID NO:2), and gp120 of *E. chaffeensis* strains Arkansas (ECU49426; SEQ ID NO:3) and Sapulpa (ECU74670; SEQ ID NO:4) were analyzed by the Tandem Repeat Finder (Benson, 1999) for period size, number of repeats, and percent homology between the repeats. The gp36 and gp47 protein sequences were tested for the presence of signal sequences with the computational algorithm SignalP trained on gram-negative bacteria (Nielsen et al., 1997).

PCR amplification of the *Ehrlichia* glycoprotein genes. Primers for the amplification of the *E. canis* and *E. chaffeensis* gp36 and gp47 genes were designed using Primer Select (Lasergene v5.08, DNAstar, Madison Wis.). Primers corresponding to nucleotides 28 to 47 (5'-ATG CTT CAT TTA ACA ACA GA, forward; SEQ ID NO:5) and 794 to 816 within the ORF (5'-AGA ATC TAA ATC TAA AAG TCC AG, reverse; SEQ ID NO:6) were used to amplify the *E. canis* gp36 gene. *E. canis* DNA was amplified using the PCR Master mix (F. Hoffmann-La Roche Ltd, Basel, Switzerland) with a thermal cycling profile of 95° C. for 4 min and 30 cycles of 95° C. for 30 s, 55° C. for 30 s, and 72° C. for 1 min, followed by a 72° C. extension for 7 min and a 4° C. hold. PCR products were separated in 1% agarose gels. Primers corresponding to nucleotides 4 to 22 (5'-CTT CAT TTA ACA ACA GAA A, forward; SEQ ID NO:7) and 902 to 924 within the ORF (5'-TTG AGC AGC CAT ATC TTC TTC AT, reverse; SEQ ID NO:8) were used to amplify the *E. chaffeensis* gp47 gene using the same PCR conditions. Recombinant protein containing the amino-terminus of *E. canis* gp36 was created by amplifying respective DNA with primers corresponding with nucleotides 28 to 47 (5'-ATG CTT CAT TTA ACA ACA GA, forward; SEQ ID NO:9) and nucleotides 321 to 345 (5'-TTG ATA AGC ATG CAC AGA AAT AAA G, reverse; SEQ ID NO:10), and the carboxyl-terminus was amplified with primers specific for nucleotides 370-392 (5'-GGA AAT CCA TCA CGT CCT GCT AT, forward; SEQ ID NO:11) and 794 to 816 (5'-AGA ATC TAA ATC TAA AAG TCC AG, reverse; SEQ ID NO:12). Recombinant protein containing the amino-terminus of *E. chaffeensis* gp47 was created by amplifying respective DNA with primers corresponding with nucleotides 4 to 22 (5'-CTT CAT TTA ACA ACA GAA A, forward; SEQ ID NO:13) and nucleotides 436 to 459 (5'-AAC TGG AAC CAC TAT ACT GTC ACT, reverse; SEQ ID NO:14) and the carboxyl-terminus was amplified with primers specific for nucleotides 439-463 (5'-GAC AGT ATA GTG GTT CCA GTT CTT G, forward; SEQ ID NO:15) and 902 to 924 (5'-TTG AGC AGC CAT ATC TTC TTC AT, reverse; SEQ ID NO:16).

Cloning and Expression of Recombinant *Ehrlichia* Glycoproteins.

The amplified PCR product was cloned directly into the pBAD Thio TOPO® expression vector (Invitrogen, Carlsbad, Calif.). TOP10 *E. coli* (Invitrogen) were transformed with the plasmid containing the *E. canis* gp36 or *E. chaffeensis* gp47 genes, and positive transformants were screened by PCR for the presence of the insert and orientation and sequenced to confirm the reading frame of the genes. Recombinant protein expression was induced with 0.2% arabinose for 3 h at 37° C. Bacteria were pelleted (5,000×g for 20 min), resuspended in PBS, and recombinant proteins were purified under native conditions as previously described (Doyle et al., 2005).

Gel Electrophoresis and Western Immunoblotting.

Purified *E. canis* or *E. chaffeensis* antigens were separated by SDS-PAGE, transferred to nitrocellulose, and Western blots performed as previously described (McBride et al., 2003), except primary antibodies were diluted (1:500). Sera from HME patients were a kind gift from Focus Technologies (Cypress, Calif.).

Mouse Immunization.

Five BALB/c mice (Jackson Laboratories, Bar Harbor, Me.) were immunized with the recombinant *E. canis* gp36 or *E. chaffeensis* gp47 proteins. Recombinant protein (100 µg) in 0.1 mL was mixed with an equal volume of Freund's complete adjuvant (Sigma, St. Louis, Mo.) for the first injection and with Freund's incomplete adjuvant for the subsequent injections. The mice were given intraperitoneal injections twice at two week intervals.

Recombinant Fusion Proteins.

Two 27-bp complementary oligonucleotides (Sigma-Genosys, Woodlands, Tex.) encoding a 9-mer repeat region of *E. canis* gp36 were synthesized. The coding strand contained additional 5' nucleotides CACC for directional TOPO vector cloning (5'-CACC ACT GAA GAT TCT GTT TCT GCT CCA GCT (SEQ ID NO:17; reverse complement 5'-AGC TGG AGC AGA AAC AGA ATC TTC AGT; SEQ ID NO:18). The oligos were resuspended in water (200 µM), combined and diluted to 100 µM in oligonucleotide annealing buffer (10 mM Tris-HCl, pH 7.5, 100 mM NaCl, 1 mM EDTA), then heated to 95° C. for 15 min and allowed to slowly cool to room temperature. This mixture was subsequently used for standard cloning into the pBAD Directional TOPO® Expression vector (Invitrogen) to express the 9-mer, TEDSVSAPA (SEQ ID NO:22), as a thioredoxin fusion protein. This procedure was repeated with the 17-mer repeat unit of the *E. chaffeensis* gp47, (oligo sequences 5'-CACC GCT AGT GTA TCT GAA GGA GAT GCA GTA GTA AAT GCT GTA AGC CAA GAA ACT CCT GCA (SEQ ID NO:19); reverse complement 5'-TGC AGG AGT TTC TTG GCT TAC AGC ATT TAC TAC TGC ATC TCC TTC AGA TAC ACT AGC; SEQ ID NO:20)).

Enzyme-Linked Immunosorbent Assay (ELISA).

ELISA plates (Nunc-Immuno™ Plates with MaxiSorp™ Surface, NUNC, Roskilde, Denmark) were coated with protein or peptide (2 µg/well, 100 µL) in phosphate buffered saline (PBS). Periodate treatment of the recombinant repeat fusion protein was carried out for 20 min in 100 mM sodium acetate/5 mM EDTA buffer with 10 mM sodium metaperiodate. Antigen was absorbed to the ELISA plates overnight at 4° C. or for 2 hr at room temperature with gentle agitation and subsequently washed three times with TBS-Tween 20 (300 µL), blocked with 1× milk diluent/blocking solution (Kirkegaard & Perry Laboratories, Gaithersburg, Md.) for 1 hr at 37° C. with agitation and washed again. Anti-*E. canis* sera diluted (1:500) in milk diluent was added to each well (100 µL) and incubated at room temperature for 1.5 h with gentle agitation. The plates were washed four times and an alkaline phosphatase-labeled goat anti-dog IgG (H+L) secondary antibody (1:3000) (Kirkegaard & Perry Laboratories) in milk diluent was added and incubated for 1 hr. The plates were washed four times and substrate (100 µL) (BluePhos, Kirkegaard & Perry Laboratories) was added to each well. The plates were incubated for 30 min in the dark with agitation, and color development was stopped with 1% SDS. The plates were subsequently read on a microplate reader (Versamax, Molecular Devices, Sunnyvale, Calif.) at A650 and data analyzed by SoftmaxPro v4.0 (Molecular Devices). The data represents the mean of three independent dog sera. A 20-mer p28-19 VR1 peptide, sequence NH2-RNTTVGVFGLKQNWDGSAIS (SEQ ID NO:21) (a kind gift from Dr. X. J. Yu), was used as a positive control peptide to confirm binding and immunoreactivity.

Immunoelectron Microscopy.

Immunogold electron microscopy was performed as previously described (Doyle et al., 2005).

Analysis of Secreted Immunoreactive Proteins.

*E. canis* or *E. chaffeensis* infected DH82 cells were monitored until 90-100% of the monolayer cells were infected. Three days prior to supernatant harvest, the culture medium (DMEM supplemented with 10% bovine calf serum) was completely removed and replaced with serum-free DMEM. Culture supernatants were collected without disturbing the cell monolayer and centrifuged (5000×g for 20 min) to pellet cells and bacteria. Supernatants were subsequently concentrated 40-fold (Amicon Ultra Centrifugal Filter Devices with a 10-kDa MW cutoff; Millipore, Billerica, Mass.). Cell culture supernatants (2 µL) were diluted 1:2 in LDS sample buffer, separated by gel electrophoresis, transferred to nitrocellulose and immunoreactive proteins detected by Western immunoblotting using anti-*E. canis* polyclonal antibody (1:500) as described previously.

Indirect Fluorescent Antibody Analysis (IFA) and Confocal Microscopy.

Antigen slides were prepared from DH82 cells infected with *E. canis* (Jake isolate) or *E. chaffeensis* (Arkansas isolate) as described previously (McBride et al., 2001). Monospecific rabbit serum produced against the recombinant *E. canis* disulfide bond formation protein (DsbA) (McBride et al. 2002) was diluted 1:100 and added to each well (15 µL) and allowed to incubate for 30 min. Slides were washed, and either mouse anti-gp36 or mouse anti-gp47 (1:100 dilution) was added and incubated for 30 min. Alexa Fluor® 488 goat anti-rabbit IgG (H & L) secondary antibody (Molecular Probes, Eugene, Oreg.) diluted 1:100 was added and incubated for 30 min, followed by washing and subsequent addition and incubation of rhodamine-labeled goat anti-mouse IgG (H & L) secondary antibody (Kirkegaard & Perry Laboratories). Slides were viewed in the Optical Imaging Laboratory at UTMB using a Zeiss LSM-510 META confocal microscope.

Nucleotide Sequence Accession Numbers.

The *E. canis* gp36 gene sequences from the Jake, Oklahoma, and Demon isolates and *E. chaffeensis* gp47 gene sequences from the Arkansas and Sapulpa isolates were deposited into GenBank and assigned the following accession numbers, respectively: *E. canis* Jake (DQ085427; SEQ ID NO:32, which encodes SEQ ID NO:37), *E. canis* Oklahoma (DQ085428; SEQ ID NO:33, which encodes SEQ ID NO:38), *E. canis* Demon (DQ085429; SEQ ID NO:34, which encodes SEQ ID NO:39), *E. chaffeensis* Arkansas (DQ085430; SEQ ID NO:35, which encodes SEQ ID NO:40), *E. chaffeensis* Sapulpa (DQ085431; SEQ ID NO:36, which encodes SEQ ID NO:41).

Exemplary "mucin" polynucleotides from Highway (SEQ ID NO:42), Welgevondon (SEQ ID NO:43) and Gardel (SEQ ID NO:44) *E. ruminantium* strains are orthologs of gp36 and gp47.

Example 2

Molecular Identification of the *E. Canis* 37-kDa Major Immunoreactive Protein

A positive clone with a 1.5-kb insert contained a complete open reading frame (ORF) encoding a predicted protein with a molecular mass of 29.3-kDa (26.7 without predicted 23 amino acid signal peptide) with homology to highly glycosylated eukaryotic mucin proteins. With the previous correlation of glycoproteins with major immunoreactive proteins, this candidate was of particular interest. The gene contained twelve tandem repeats at the 3' end of the ORF (FIG. 1) encoding 9 amino acids (Table 2). The NetOGlyc O-linked glycosylation prediction server predicted that the serines and threonines of the tandem repeats, with exemplary predicted sequence TEDSVSAPA (SEQ ID NO:22), were the sites of glycosylation (bold letters, Table 1). The *E. chaffeensis* Arkansas strain genome was BLAST searched with the *E. canis* gp36 sequence, and a homologous open reading frame encoding a protein with seven exemplary 19-mer tandem repeats (ASVSEGDAVVNAVSQETPA; SEQ ID NO:23) and a predicted mass of 32.9-kDa was identified. The DNA sequence upstream of the tandem repeat region contained a similarity index of 61.5% (57.0% amino acid), but tandem repeat regions were not homologous.

TABLE 2

*Ehrlichia* tandem repeats of major immunoreactive glycoproteins.

| Source | Strain | Repeat length (bp) | Copy number (DNA seq) | Repeat percent homology | Consensus Tandem Repeat Sequence (amino acid) |
|---|---|---|---|---|---|
| Eca gp36 | Jake | 27 | 12.2 | 100 | TEDSVSAPA (SEQ ID NO: 22) |
| | Oklahoma | 27 | 5.2 | 100 | |
| | Demon | 27 | 16.2 | 100 | |
| Ech gp47 | Arkansas | 57 | 7.0 | 99 | ASVSEGDAVVNAVSQETPA (SEQ ID NO: 23) |
| | Sapulpa | 99 | 4.5 | 99 | EGNASEPVVSQEAAPVSESGDAANPVSSSENAS (SEQ ID NO: 24) |
| Eru Mucin-like protein | Highway | 27 | 21.7 | 99 | VTSSPEGSV (SEQ ID NO: 25) |
| | Welgevondon | 27 | 56.0 | 95 | |
| | Gardel | 66 | 16.9 | 99 | SSEVTESNQGSSASVVGDAGVQ (SEQ ID NO: 26) |
| Eca gp140 | Jake | 108 | 14.3 | 96 | KEESTPEVKAEDLQPAVDGSVEHSSSEVGEKVSETS (SEQ ID NO: 27) |
| Ech gp120 | Arkansas | 240 | 4.5 | 98 | EDEIVSQPSSEPFVAESEVSKVEQEETNPEVLIKDLQ |
| | Sapulpa | 240 | 3.5 | 97 | DVASHESGVSDQPAQVVTERESEIESHQGETEKESG ITESHQK (SEQ ID NO: 28) |

The genes encoding gp36 of *E. canis* Oklahoma and Demon strains as well as the gp47 of *E. chaffeensis* Sapulpa strain were sequenced to identify potential variations in the gene sequence. Different *E. canis* strains retained identical tandem repeat sequence, but they differed in the number of the repeats (Table 2). Interestingly, the Sapulpa strain of *E. chaffeensis* encoded an entirely different set of tandem repeats (4 full repeats of 33 amino acids) than found in *E. chaffeensis* Arkansas strain. The *E. chaffeensis* gp47 gene sequences upstream of the repeat region contained 99.8% homology between strains, but had a low degree of (27.7%) homology primarily associated with the 3' region downstream of the tandem repeats. The region just upstream of the Arkansas tandem repeats encodes the amino acids Glu-Gly-Asn, which are the 1st three amino acids of the Sapulpa strain repeat, suggesting a more recent tandem repeat switch. The nucleic acid sequence within the tandem repeats of each gp47 gene was highly conserved (at least 99%) (Table 2).

Although the tandem repeat sequences varied greatly among the different species and strains, there was a conservation of amino acid usage among the repeats. A total of ten amino acids were used in the all of the repeats, with a particularly high occurrence of serine, threonine, alanine, proline, valine, and glutamic acid. Analysis of the glycoprotein amino acid sequence upstream of the repeats compared to that including the repeats until the termination codon demonstrated a substantial increase in usage of these amino acids (Table 3). Predicted glycosylation sites by NetOGlyc were found only within the tandem repeats of the proteins (Table 2). The threonine residues within the *E. chaffeensis* repeat were predicted sites for glycan attachment, and serine residues exhibited a high potential, but were not identified as glycan attachment sites. Similarly, the *E. ruminantium* Gardel strain "mucin-like" protein contained a threonine and several serine residues that were slightly below the predicted threshold as sites of glycan attachment.

gp36 (FIG. 2A, lane 2). The recombinant *E. chaffeensis* gp47 also exhibited strong immunoreactivity (FIG. 2B, lane 1), migrated larger than the predicted mass (32.9 kDa), and carbohydrate was detected (FIG. 2B, lane 2).

Example 4

Identification of Native gp36 and gp47

A native *E. canis* protein of molecular mass 36-kDa, which corresponded to the ~37-kDa protein previously described (McBride et al., 2003), reacted with monospecific mouse antiserum produced against the recombinant protein by Western blot (FIG. 3A). A less prominent protein was also visualized at 34-kDa. Mouse anti-recombinant gp47 identified a 47-kD protein in *E. chaffeensis* whole cell lysates (FIG. 3B). Western immunoblots of *E. chaffeensis* whole cell lysates were reacted with ten suspected HME patient sera that had detectable *E. chaffeensis* antibodies by indirect fluorescent antibody analysis (IFA). Seven of ten sera recognized an immunoreactive 47-kDa protein identical in mass to the protein recognized by anti-recombinant gp47 serum (FIG. 3B).

Example 5

Early Antibody Response to gp36

Kinetic studies of the host response to *E. canis* demonstrated that a ~37-kDa antigen was recognized earliest by antibodies in acute phase sera from dogs experimentally infected with *E. canis* (McBride et al., 2003). Western immunoblot confirmed that the recombinant gp36 was not recognized by pre-inoculation sera, but that antibodies were produced against gp36 in the early acute phase (day 14) (FIG. 4), confirming the identity of the gp36 as the major

TABLE 3

Amino acid analysis of ehrlichial glycoproteins.

| | | Ser | | Thr | | Ala | | Pro | | Val | | Glu | |
|---|---|---|---|---|---|---|---|---|---|---|---|---|---|
| Source | Strain | Non-rpt | Rpt-term | Non-rpt | Rpt-term | Non-rpt | Rpt-term | Non-rpt | Rpt-term | Non-rpt | Rpt-term | Non-rpt | Rpt-term |
| Eca gp36 | Jake | 6.4 | 22.0 | 4.1 | 11.9 | 5.3 | 22.0 | 4.1 | 11.0 | 5.3 | 11.0 | 3.5 | 11.0 |
| | Oklahoma | 6.4 | 21.7 | 4.1 | 13.0 | 5.3 | 21.7 | 4.1 | 10.9 | 5.3 | 10.9 | 3.5 | 10.9 |
| | Demon | 6.4 | 22.1 | 4.1 | 11.7 | 5.3 | 22.1 | 4.1 | 11.0 | 5.3 | 11.0 | 3.5 | 11.0 |
| Ech gp47 | Arkansas | 9.2 | 15.8 | 3.3 | 4.5 | 6.0 | 21.8 | 3.3 | 5.3 | 8.7 | 21.1 | 5.4 | 10.5 |
| | Sapulpa | 9.9 | 21.8 | 3.3 | 1.4 | 6.0 | 17.0 | 3.3 | 9.5 | 8.8 | 12.2 | 5.0 | 15.7 |
| Eru Mucin-like protein | Highway | 8.9 | 32.3 | 6.4 | 11.3 | 2.6 | 1.0 | 1.9 | 11.3 | 8.3 | 21.5 | 6.4 | 11.3 |
| | Welgevonden | 8.2 | 27.2 | 6.3 | 11.1 | 1.9 | 12.3 | 1.9 | 11.1 | 7.6 | 15.3 | 7.6 | 11.1 |
| | Gardel | 8.8 | 27.4 | 5.0 | 4.6 | 2.5 | 8.3 | 1.9 | 0 | 7.6 | 18.8 | 7.6 | 9.1 |

Example 3

Immunoreactivity and Glycosylation of gp36 and gp47

The recombinant *E. canis* gp36 reacted strongly with serum antibodies from a dog experimentally infected with *E. canis* (FIG. 2A, lane 1). Following cleavage of the fusion partner thioredoxin, the recombinant protein exhibited a molecular mass of 36-kDa (data not shown), which was significantly larger than predicted by amino acid sequence (26.7 kDa). Carbohydrate was detected on the recombinant 37-kDa antigen of *E. canis*. The antibody response against gp36 remained very strong through convalescence (day 56) (FIG. 4).

Example 6

Immunoreactivity of the gp36 and gp47 Tandem Repeats

Western immunoblotting determined that the carboxyl-terminus including the tandem repeats was the highly immunoreactive portion of the protein, but homologous N-terminal regions preceeding the tandem repeat regions of the gp36 and gp47 were not immunoreactive (data not shown). A single repeat expressed as a recombinant fusion protein was recognized by anti-*E. canis* dog serum (FIG. 5B). The fusion protein containing the 9-mer demonstrated an electrophoretic shift larger than the predicted mass (~900 kDa), suggesting that the peptide was post-translationally modified and corroborating the NetOGlyc prediction, that identified the repeat units as sites of glycan attachment (FIG. 5A). A fusion protein containing a single 17-mer repeat of the *E. chaffeensis* gp47 was also recognized by anti-*E. chaffeensis* dog serum (FIG. 5C). The gp36 and gp47 were antigenically distinct, as neither reacted with heterologous antisera (FIGS. 6A and 6B).

Carbohydrate is an important part of the gp36 epitope determinant. As each tandem repeat unit of *E. canis* gp36 was a predicted site of glycosylation and found to contain a major B cell epitope, the present inventors hypothesized that attached glycans were important epitope determinants. To confirm this, the 9-mer repeat fusion protein was treated with periodate to test antibody recognition following structural modification of the glycan. The untreated 9-mer fusion protein reacted with anti-*E. canis* dog serum by ELISA; however, the recognition of periodate treated 9-mer fusion protein fusion was greatly reduced and a synthetic peptide with the sequence of the repeat region was not recognized at all, demonstrating the requirement of post-translational modification for antibody binding (FIG. 6). Structural modification of the glycan by periodate treatment reduced antibody recognition of the epitope almost to the background level of thioredoxin alone as determined by reduction in ELISA O.D. values.

Example 7

Carbohydrate is an Important gp36 Epitope Determinant

As each tandem repeat unit of *E. canis* gp36 was a predicted site of glycosylation and found to contain a major B-cell epitope, the inventors considered that attached glycans were important epitope determinants. To characterize this, recombinant *E. canis* gp36 was treated with periodate to test antibody recognition following structural modification of the glycan. The sham-treated gp36 reacted strongly with anti-*E. canis* dog serum by ELISA, while the periodate-treated recombinant gp36 was substantially reduced (FIG. 7A). To further characterize this observation, ELISA was used to test the recognition of recombinant fusion proteins with a single repeat (9-mer; TEDSVSAPA; SEQ ID NO:22), a 12-mer (SVSAPATEDSVS; SEQ ID NO:45), and two tandem repeat units (18-mer; TEDSVSAPATEDSVSAPA; SEQ ID NO:46) from gp36 in comparison with nonglycosylated synthetic peptides with the identical sequences. Whereas all of the recombinant proteins were recognized with immune dog serum, the synthetic single repeat (9-mer) was not recognized at all, and the overlapping peptide (12-mer) exhibited minimal reactivity, demonstrating the importance of posttranslational modification for antibody binding to these peptides (FIG. 7B). The tandem repeat (18-mer) synthetic peptide was recognized by dog serum, although not as well as the recombinant, demonstrating the presence of a linear amino acid-based epitope present in a tandem repeat unit-containing peptide (18-mer) (FIG. 7B). Recognition of the recombinant *E. chaffeensis* repeat fusion protein exhibited an absorbance by ELISA higher than that of synthetic peptide (FIG. 7C).

Example 8

Cellular Localization and Secretion of gp36 and gp47

Ehrlichiae exist in two distinct morphologic forms known as reticulate and dense-cored (Popov et al., 1995). The localization of *E. canis* gp36 (FIG. 8A) and *E. chaffeensis* gp47 (FIG. 8B) by immunogold electron microscopy found that these proteins were differentially expressed on the surface of the dense-cored form of the bacteria, but not the reticulate form. The gp36 and gp47 were also associated with the morula membranes containing the dense-cored morphological forms of the bacteria (FIGS. 8A and 8B). Differential expression of the *E. canis* gp36 and *E. chaffeensis* gp47 was further confirmed by IFA analysis and confocal microscopy of infected cell slides using antibodies against the conserved ehrlichial disulfide bond formation protein Dsb in addition to gp36 or gp47. The IFA demonstrated that *E. canis* gp36 and *E. chaffeensis* gp47 were expressed on a subset of ehrlichiae compared to the expression of Dsb (constitutively expressed).

The *E. canis* gp36 and *E. chaffeensis* gp47 were the predominant immunoreactive proteins secreted into the supernatant (FIGS. 9A and 9B, lanes 1). The *E. canis* gp36 and *E. chaffeensis* gp47 were conclusively identified in the supernate fractions with anti-recombinant gp36 and gp47 antibodies (FIGS. 9A and 9B, lanes 2). Supernatants from uninfected DH82 cells did not contain any proteins recognized by antisera against ehrlichiae (data not shown).

Example 9

Molecular Characterization of *E. canis* gp36 and *E. chaffeensis* gp47 Tandem Repeats Among Isolates from Different Geographic Locations Concerning the major immunoreactive orthologous glycoproteins of *Ehrlichia canis* and *E. chaffeensis*, gp36 and gp47, the inventors characterized the tandem repeats molecularly. The genes encoding these proteins contain tandem repeats near the carboxyl-terminus that are sites of O-linked glycosylation. Single repeat units from both gp36 and gp47 contain epitopes that are recognized by dog antisera but are not cross-reactive. Comparative analyses in limited numbers of North American *E. canis* and *E. chaffeensis* determined that the tandem repeats varied in number and sequence among the isolates. To further characterize the global conservation or heterogeneity of these proteins, particularly with respect to the tandem repeat regions, the gp36 and gp47 genes were amplified and compared in several continentally separated strains of *E. canis* and numerous geographically dispersed North American *E. chaffeensis* isolates. Primers were designed to intergenic regions upstream and downstream of the *E. canis* and *E. chaffeensis* gp36 and gp47 coding regions (*E. canis* gp36 forward 5'-AAT CAA TGT AGT ATG TTT CTT TTA (SEQ ID NO:47) and reverse 5'-ATT TTA CAG GTT ATA TTT CAG TTA (SEQ ID NO:48); *E. chaffeensis* gp47 forward 5'-TTG TGC AGG GAA AGT TG (SEQ ID NO:49) and reverse 5'-AAT GAA AGT AAA TAA GAA AGT GTA (SEQ ID NO:50)), and amplification was carried out as previously described (Doyle et al., 2006) The *E. canis* gp36 gene sequences from the Louisiana (DQ146151; SEQ ID NO:52 polynucleotide encoding SEQ ID NO:53), Florida (DQ146152; SEQ ID NO:54 polynucleotide encoding SEQ ID NO:55), DJ (North Carolina)(DQ146153; SEQ ID NO:56 polynucleotide encoding SEQ ID NO:57), Sao Paulo (DQ146154; SEQ ID NO:58 polynucleotide encoding SEQ ID NO:59), and Cameroon 71 (DQ146155; SEQ ID NO:60 polynucleotide encoding SEQ ID NO:61) isolates and *E. chaffeensis* gp47 gene sequences from the Jax (DQ146156; SEQ ID NO:62 polynucleotide encoding SEQ ID NO:63), St. Vincent (DQ146157; SEQ ID NO:64 polynucleotide encoding SEQ ID NO:65), V3 (Vanderbilt) (DQ146158; SEQ ID NO:66 polynucleotide encoding SEQ ID NO:67) and V8 (DQ146159; SEQ ID NO:68 polynucleotide encoding SEQ ID NO:69) isolates were deposited into the publicly available GenBank database of the National Center for Biotechnology Information world wide website. The *E. canis* gp36 gene sequences from the Jake (DQ085427), Oklahoma (DQ085428), and Demon (DQ085429) isolates and *E. chaffeensis* gp47 gene sequences from the Arkansas (DQ085430) and Sapulpa (DQ085431) isolates were previously deposited. Sequence analysis was performed as previously described (Doyle et al., 2006)

The tandem repeat sequence from North American, Brazilian, and Cameroonian *E. canis* isolates was completely conserved, comprising nine amino acids (TEDSVSAPA; SEQ ID NO:22). However, the number of repeats varied between 4 and 18 copies of the repeat (see Table 4). The N-terminal pre-repeat region (143 amino acids) was highly conserved among all isolates, with the Jake, Oklahoma, Demon, and Louisiana strains containing complete homology. The Brazil and Cameroon isolates contained the most divergent sequences (four differences in amino acids), but these still retained 97.2% amino acid homology with the consensus.

TABLE 4

Tandem repeats of gp36 and gp47 in different *E. canis* and *E. chaffeensis* strains

| Tandem Repeat | Strain | Repeat number | Percent homology |
|---|---|---|---|
| *E. canis* gp36 | Jake | 12.2 | 100 |
| | Oklahoma | 5.2 | 100 |
| TEDSVSAPA (9 amino | Demon | 16.2 | 99 |
| acids) (SEQ ID NO: 22) | Louisiana | 5.2 | 99 |
| | Florida | 4.2 | 100 |
| | DJ | 18.2 | 100 |
| | Sao Paulo | 18.2 | 100 |
| | Cameroon 71 | 16.2 | 100 |
| *E. chaffeensis* gp47 | | | |
| ASVSEGDAVVNAVSQETPA (19 amino acids; SEQ ID NO: 23) | Arkansas | 7.0 | 99 |
| EGNASEPVVSQEAAPVSE SGDAANPVSSENAS (33 amino acids; SEQ ID NO: 24) | Jax | 4.5 | 98 |
| | St Vincent | 3.4 | 98 |
| | Sapula | 4.5 | 99 |
| | V3 | 4.5 | 97 |
| | V8 | 4.5 | 98 |

Similarly, the *E. chaffeensis* isolates tested demonstrated limited diversity of gp47 tandem repeats. The Arkansas strain exhibited a unique 19 amino acid repeat unit compared to all of the other isolates sequenced. Seven repeats of the 19 amino acid sequence were identified in the Arkansas strain gp47 gene. Five additional *E. chaffeensis* isolates from geographically dispersed locations had a conserved 33 amino acid repeat unit that exhibited minor variability in repeat sequence (see Table 4). The number of copies among this repeat was identical among three of four isolates (4.5 repeats), with the St. Vincent containing one fewer repeat (see Table 4). The N-terminal repeat pre-repeat regions (154 amino acids) were completely conserved between the Sapulpa, St. Vincent, V3, and V8 strains. This sequence contained 99.4% amino acid (one alteration) conservation with the pre-repeat region of the Arkansas strain. More divergence was found in the Jax strain, with 91.6% amino acid homology (13 substitutions) in the pre-repeat region compared with the rest of the strains. Although these proteins are highly immunoreactive and tandem repeat units of gp36 and gp47 contain the B cell epitopes (Doyle et al. 2006), interestingly, the lack of sequence divergence indicates that there is little immune selective pressure on these proteins to alter their sequence or they must be conserved to retain function, in specific embodiments. Similarly, comparative sequence analysis failed to detect significant similarity between the repeat units, demonstrating the tandem repeats are not derived from common sequence that went through multiple mutations to gain diversity. The distinct tandem repeats of gp47 will further assist in differentiating variant strains into clades, and in particular aspects of the invention provides insight into pathogenic differences among the strains. As these orthologous glycoproteins are highly immunogenic (Doyle et al., 2006), the complete conservation of tandem repeats between strains of *E. canis* around the world and limited divergence between *E. chaffeensis* could have positive implications for future use of these proteins. With the tandem repeat units containing epitopes, a sensitive immunodiagnostic assay for *E. canis* is developed using a recombinant protein with these tandem repeats.

Example 10

Vaccines of the Invention

In particular aspects of the invention, the immunogenic compositions of the present invention are suitable as a vaccine, such as a subunit vaccine. In other aspects of the invention, the immunogenic compositions are referred to as immunoprotective.

Specifically, one or more compositions of the invention, such as those comprising an *E. canis* gp36 epitope or an *E. chaffeensis* gp47 epitope, for example, are administered to a mammal, such as a canine. Serum from the mammal may be assayed for an immune response, such as by detecting antibodies in the serum. The mammal is then subjected to subsequent challenge with the pathogenic organism, such as the respective *E. canis* or *E. chaffeensis* organisms, and immunoprotection is determined. Controls may be employed, such as immunization with, for example, a mutated epitope or an epitope that does not comprise a carbohydrate moiety. Complete or partial protection against the subsequent challenge demonstrates the immunoprotective nature of the composition, and the composition is a vaccine. Partial protection may be defined as protecting from developing at least one symptom of the infection or protecting from at least one symptom becoming worse.

Example 11

Significance of the Present Invention

The present inventors' previous study of the kinetic antibody responses to *E. canis* revealed two major immunoreactive antigens (36- and 19-kD proteins) as dominant targets of the early host immune response (McBride et al., 2003). The antigenic composition of *E. canis* in the tick is not known, but antigens recognized early in the host immune response provide evidence of those that may be especially important in the initial stages of infection of the mammalian host, and thus are high priority targets for molecular identification and for vaccine development. In this invention, the present inventors have conclusively identified and molecularly characterized the *E. canis* 36 kD major immunoreactive protein, and, similar to several other major ehrlichial immunoreactive proteins, it is glycosylated. In addition, a divergent and antigenically distinct 47-kD ortholog in *E. chaffeensis*, also a major immunoreactive protein consistently recognized by antibodies from HME patients, was identified. Other major immunoreactive proteins that have been molecularly characterized in *E. canis* include three glycoproteins (gp200, gp140, and p28/p30), and the identification of the gp36 in *E. canis* further supports glycosylation as an important ehrlichial post-translational modification on several surface exposed proteins.

The *E. canis* gp36 and *E. chaffeensis* gp47 have considerable nucleic acid and amino acid divergence in regions containing the serine/threonine-rich tandem repeats. The recent genome sequence analysis of *Ehrlichia ruminantium* (Collins et al., 2005) and *E. canis* (unpublished data) has identified a high frequency of genes containing tandem repeat units. The *E. canis* gp140 and the *E. chaffeensis* gp120 orthologs also have longer but genetically divergent, tandem repeats. None of the known glycoprotein repeat regions share conserved sequences among them, but all exhibit high serine and threonine content in addition to alanine, proline, valine, and glutamic acid residues that have been reported to serve as recognition motifs for O-glycan attachment (O'Connell et al., 1991; Thanka Christlet and Veluraja, 2001). The repeat units of the "mucin-like" glycoproteins were the only location of predicted O-glycan attachment as predicted by NetOGlyc, but not all of the serines and threonines crossed the threshold as probable sites of glycosylation. However, as NetOGlyc was developed with data from eukaryotic glycoproteins, it is quite possible that the threshold for ehrlichial glycosylation is lower and that these are sites of glycosylation. As with other known ehrlichial glycoprotein orthologs, the gp36 and gp47 are antigenically divergent. Consistent immunodominance and divergence of the tandem repeats suggest that the immune response creates strong selective pressures to alter the sequence of the repeats. However, all *E. canis* strains tested contained identical tandem repeats, but had variable repeat numbers (5 to 16). *E. chaffeensis* exhibited more divergence (amino acid sequence and repeat number) in the tandem repeat regions from two isolates that were examined (Arkansas and Sapulpa). Three of ten HME patient sera tested did not react with the gp47 from *E. chaffeensis* Arkansas strain, and the divergence in the repeat region of could explain the inconsistency of gp47 recognition by different patients. A search for orthologous tandem repeat DNA sequences throughout the genome does not detect pseudogenes or other sources for the nascent repeats, so the mechanism for repeat divergence remains elusive. The discovery of a new pair of surface expressed orthologs with repeat units is a point of interest in an obligate intracellular organism that has undergone reductive genome evolution, and thus leads to speculation that there may be a selective advantage to increase and retain the glycosylated repeat units of these proteins.

Although the gp36 and gp47 have considerable homology in the N-terminal regions upstream of the repeat regions, the immunoreactive regions were localized to carboxyl-terminus region of the proteins, which contains the tandem repeats. The present inventors determined that single repeats from *E. canis* gp36 (9-mer) and *E. chaffeensis* gp47 (19-mer) expressed as recombinant proteins were sufficient for antibody recognition by immune sera, demonstrating that they contain major repeated epitopes. Similarly, the repeat regions of the *E. canis* gp120 and *E. chaffeensis* gp140 contain major antibody epitopes. Interestingly, synthetic peptides of the *E. canis* gp36 repeat (9-mer) and *E. chaffeensis* repeat (27-mer) were not recognized by immune serum and periodate treatment of recombinant repeat unit nearly abrogated antibody recognition, providing the first evidence that the epitope determinants are complex and require post-translational modification for antibody recognition. In the absence of organelles for protein trafficking, it was long believed that prokaryotes did not contain the cellular machinery needed to modify proteins with carbohydrates. Even *E. coli*, used for many years to express aglycosylated eukaryotic proteins, has been found to modify its own proteins with carbohydrate moieties (Lindenthal and Elsinghorst, 1999). Several human bacterial pathogens have now been discovered to express glycoproteins (Benz and Schmidt, 2002; Schmidt et al., 2003; Upreti et al., 2003) and the few prokaryotic glycoproteins functionally characterized contribute to adhesion, structural stability, and mobility, and are also targets of the immune system. These characteristics demonstrate the potential roles of bacterial glycoproteins in pathogenesis and immunity (Benz and Schmidt, 2002). Significantly, the carbohydrate-dependent antibody recognition of recombinant gp36 and gp47 expressed in *E. coli* demonstrates that glycans and attachment sites are conserved between native ehrlichial proteins and recombinant glycoprotein expressed in *E. coli*. This indicates that the mechanisms for glycosylation are conserved between *Ehrlichia* and *E. coli*. However, glycosyltransferases homologous to those present in *E. coli* have not been identified in the *E. canis* genome (unpublished data), suggesting that these enzymes contain unique sequences and are among the hypothetical proteins with unknown function. Based on the identical protein masses and the dependence of post-translational modification for glycoprotein epitope reactivity, the recombinant ehrlichial glycoproteins appear to be identical to the native proteins in structure and composition, and thus are appropriate surrogates for native proteins in studies to determine function and role as immunoprotective antigens.

The present inventors have observed that the gp36 and gp47 are present in relatively low abundance in whole cell lysates compared to other outer membrane proteins such as p28/p30. Several ehrlichial proteins have been identified outside the bacterial cell including the gp120 and ferric-ion binding protein. Furthermore, the *E. chaffeensis* gp120 has been demonstrated to be differentially expressed on the surface of dense-cored *E. chaffeensis* and extracellularly in the morula matrix. Immunogold electron microscopy demonstrated that *E. canis* gp36 and *E. chaffeensis* gp47 are also differentially expressed on the surface of dense-cored ehrlichiae. The dense-cored and reticulate cell morphological forms of *Ehrlichia* are thought to be homologous to the infectious elementary body form of *Chlamydia trachomatis* and metabolically active reticulate body, respectively. This observation indicates that these orthologous glycoproteins may play an important role in ehrlichial infection. The cell surface expression of these glycoproteins indicates that they function as adhesins, in specific embodiments of the invention. Carbohydrate-lectin interactions are common means of bacterial adhesion, and *E. chaffeensis* has been demonstrated to use L- and E-selectins to mediate cellular binding (Zhang et al., 2003). Repeat-containing proteins from *Anaplasma marginale* as well as the "mucin-like" protein ortholog from *Ehrlichia ruminantium* have been demonstrated to confer to ability to adhere to tick cells (de la Fuente et al., 2004).

The gp36 and gp47 are minor constituents in whole cell lysates, but the present inventors found substantial amounts of both in supernatants of infected cells. Interestingly, these were the abundant immunoreactive proteins found in the supernatants in which other known surface proteins such as the p28/p30 were not detected, indicating that the gp36 was indeed secreted and was not associated with intact outer membranes in the supernatants. The secretion of gp36 in the tick salivary gland or in the mammalian host would provide a partial explanation for the early host immune response to this glycoprotein. Furthermore, secretion of these glycoprotein orthologs (gp36 and gp47) suggests that they may be virulence factors and play an important role in pathobiology. A signal sequence was identified on the gp36, suggesting the involvement of a sec dependent secretion mechanism such as Type II or Type IV (Nagai and Roy, 2003). Genes encoding Type IV secretion machinery have been identified in *E. canis*, *E. chaffeensis*, and *E. ruminantium* (Collins et al., 2005; Felek et al., 2003; Ohashi et al., 2002) as the role of type IV secretion of bacterial virulence factors is becoming better recognized.

The early immune recognition of gp36 by the mammalian host immune response indicates the possibility that this antigen plays an important role in ehrlichial infection of the tick or in transmission and early stages of infection, in specific embodiments of the invention. Although very little is known with regard to ehrlichial antigen expression in the tick, differential expression of *Borrelia burgdorferi* outer surface proteins has been demonstrated in the tick and restriction of *A. marginale* msp2 variants in ticks has been reported (Rurangirwa et al., 1999; Schwan and Hinnebusch, 1998). Successful infection of the ticks or mammalian host may be determined by the expression of specific outer membrane proteins required for host cell attachment or those involved in establishment of intracellular infection.

Kinetics of the antibody response and antibody reactivity of the *E. canis* gp36 indicates that this antigen is useful in vaccine and immunodiagnostic development. Current commercially available diagnostic assays for canine ehrlichiosis are based on p28/p30 proteins, and the gp36 could provide substantially better sensitivity for this application. Furthermore, the gp36 antigen did not react with immune sera from *E. chaffeensis* dogs, which could be useful in developing species-specific immunodiagnostic assays. Similar serologic species specificity has been reported with the gp120/gp140 as well as the gp200 orthologs of *E. canis* and *E. chaffeensis*. These observations indicate that the serologic cross-reactivity reported between *E. canis* and *E. chaffeensis* is not elicited by these major immunoreactive antigens. This finding also has relevance to subunit vaccine development, indicating that these antigens are effective against homologous, in specific aspects of the invention. Vaccines that could potentially block infection during transmission would preferably contain antigens expressed in the tick, and thus in specific embodiments the expression of gp36 in the tick vector is determined.

The discovery of another set of major immunoreactive glycoprotein orthologs from ehrlichiae demonstrates their importance as targets of the immune system and their utility as immunoprotective antigens.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

Patents and Patent Applications

U.S. Pat. No. 5,681,947
U.S. Pat. No. 5,652,099
U.S. Pat. No. 5,763,167
U.S. Pat. No. 5,614,617
U.S. Pat. No. 5,670,663
U.S. Pat. No. 5,872,232
U.S. Pat. No. 5,859,221
U.S. Pat. No. 5,446,137
U.S. Pat. No. 5,886,165
U.S. Pat. No. 5,714,606
U.S. Pat. No. 5,672,697
U.S. Pat. No. 5,466,786
U.S. Pat. No. 5,792,847
U.S. Pat. No. 5,223,618
U.S. Pat. No. 5,470,967
U.S. Pat. No. 5,378,825
U.S. Pat. No. 5,777,092
U.S. Pat. No. 5,623,070
U.S. Pat. No. 5,610,289
U.S. Pat. No. 5,602,240
U.S. Pat. No. 5,858,988
U.S. Pat. No. 5,214,136
U.S. Pat. No. 5,700,922
U.S. Pat. No. 5,708,154
U.S. Pat. No. 5,786,461
U.S. Pat. No. 5,891,625
U.S. Pat. No. 5,773,571
U.S. Pat. No. 5,766,855
U.S. Pat. No. 5,736,336
U.S. Pat. No. 5,719,262
U.S. Pat. No. 5,714,331
U.S. Pat. No. 5,539,082
U.S. Pat. No. 5,766,855
U.S. Pat. No. 5,719,262
U.S. Pat. No. 5,714,331
U.S. Pat. No. 5,736,336
WO 92/20702

Publications

Benson, G. 1999. Tandem repeats finder: a program to analyze DNA sequences. Nucleic Acids Res. 27:573-580.

Benz, I. and M. A. Schmidt. 2002. Never say never again: protein glycosylation in pathogenic bacteria. Mol. Microbiol. 45:267-276.

Breitschwerdt, E. B., B. C. Hegarty, and S. I. Hancock. 1998. Sequential evaluation of dogs naturally infected with *Ehrlichia canis, Ehrlichia chaffeensis, Ehrlichia equi, Ehrlichia ewingii*, or *Bartonella vinsonii*. J. of Clin. Microbiol. 36:2645-2651.

Chen, S. M., J. S. Dumler, H. M. Feng, and D. H. Walker. 1994. Identification of the antigenic constituents of *Ehrlichia chaffeensis*. Am. J. Trop. Med. Hyg. 50:52-58.

Chen, S. M., L. C. Cullman, and D. H. Walker. 1997. Western immunoblotting analysis of the antibody responses of patients with human monocytotropic ehrlichiosis to different strains of *Ehrlichia chaffeensis* and *E. canis*. Clin. Diagn. Lab Immunol. 4:731-735.

Collins, N. E., J. Liebenberg, E. P. de Villiers, K. A. Brayton, E. Louw, A. Pretorius, F. E. Faber, H. van Heerden, A. Josemans, M. van Kleef, H. C. Steyn, M. F. van Strijp, E. Zweygarth, F. Jongejan, J. C. Maillard, D. Berthier, M. Botha, F. Joubert, C. H. Corton, N. R. Thomson, M. T. Allsopp, and B. A. Allsopp. 2005. The genome of the heartwater agent *Ehrlichia ruminantium* contains multiple tandem repeats of actively variable copy number. Proc. Natl. Acad. Sci. U.S.A 102:838-843.

de la, Fuente. J., J. C. Garcia-Garcia, A. F. Barbet, E. F. Blouin, and K. M. Kocan. 2004. Adhesion of outer membrane proteins containing tandem repeats of *Anaplasma* and *Ehrlichia* species (Rickettsiales: Anaplasmataceae) to tick cells. Vet. Microbiol. 98:313-322.

Doyle, C. K., X. Zhang, V. L. Popov, and J. W. McBride. 2005. An immunoreactive 38-kilodalton protein of *Ehrlichia canis* shares structural homology and iron-binding capacity with the ferric ion-binding protein family. Infect. Immun. 73:62-69.

Doyle, C. K., V. L. Popov, and J. W. McBride. 2006. Differentially expressed and secreted major immunoreactive protein orthologs of *Ehrlichia canis* and *E. chaffeensis* elicit early antibody responses to epitopes on glycosylated tandem repeats. Infect. Immun. 74. In press.

Felek, S., H. Huang, and Y. Rikihisa. 2003. Sequence and expression analysis of virB9 of the type IV secretion system of *Ehrlichia canis* strains in ticks, dogs, and cultured cells. Infect. Immun. 71:6063-6067.

Julenius, K., A. Molgaard, R. Gupta, and S. Brunak. 2005. Prediction, conservation analysis, and structural characterization of mammalian mucin-type O-glycosylation sites. Glycobiology 15:153-164.

Lindenthal, C. and E. A. Elsinghorst. 1999. Identification of a glycoprotein produced by enterotoxigenic *Escherichia coli*. Infect. Immun. 67:4084-4091.

McBride J W, R. E. Corstvet, S. D. Gaunt, C. Boudreaux, T. Guedry, and D. H. Walker. 2003. Kinetics of antibody response to *Ehrlichia canis* immunoreactive proteins. Infect. Immun. 71:2516-2524.

McBride, J. W., J. E. Comer, and D. H. Walker. 2003. Novel Immunoreactive glycoprotein orthologs of *Ehrlichia* spp. Ann. N.Y. Acad. Sci. 990:678-684.

McBride, J. W., L. M. Ndip, V. L. Popov, and D. H. Walker. 2002. Identification and functional analysis of an immunoreactive DsbA-like thio-disulfide oxidoreductase of *Ehrlichia* spp. Infect. Immun. 70:2700-2703.

McBride, J. W., R. E. Corstvet, E. B. Breitschwerdt, and D. H. Walker. 2001. Immunodiagnosis of *Ehrlichia canis* infection with recombinant proteins. J. Clin. Microbiol. 39:315-322.

McBride, J. W., X. J. Yu, and D. H. Walker. 2000. Glycosylation of homologous immunodominant proteins of *Ehrlichia chaffeensis* and *E. canis*. Infect. Immun. 68:13-18.

McBride, J. W., X. Yu, and D. H. Walker. 2000. A conserved, transcriptionally active p28 multigene locus of *Ehrlichia canis*. Gene 254:245-252.

Nagai, H. and C. R. Roy. 2003. Show me the substrates: modulation of host cell function by type IV secretion systems. Cell. Microbiol. 5:373-383.

Nielsen, H., J. Engelbrecht, S. Brunak, and G. von Heijne. 1997. Identification of prokaryotic and eukaryotic signal peptides and prediction of their cleavage sites. Protein Eng. 10:1-6.

O'Connell, B., L. A. Tabak, and N. Ramasubbu. 1991. The influence of flanking sequences on O-glycosylation. Biochem. Biophys. Res. Commun. 180:1024-1030.

Ohashi, N., A. Unver, N. Zhi, and Y. Rikihisa. 1998. Cloning and characterization of multigenes encoding the immunodominant 30-kilodalton major outer membrane proteins of *Ehrlichia canis* and application of the recombinant protein for serodiagnosis. J. Clin. Microbiol. 36:2671-2680.

Ohashi, N., N. Zhi, Q. Lin, and Y. Rikihisa. 2002. Characterization and transcriptional analysis of gene clusters for a type IV secretion machinery in human granulocytic and monocytic ehrlichiosis agents. Infect. Immun. 70:2128-2138.

Ohashi, N., N. Zhi, Y. Zhang, and Y. Rikihisa. 1998. Immunodominant major outer membrane proteins of *Ehrlichia chaffeensis* are encoded by a polymorphic multigene family. Infect. Immun. 66:132-139.

Ohashi, N., Y. Rikihisa, and A. Unver. 2001. Analysis of transcriptionally active gene clusters of major outer membrane protein multigene family in *Ehrlichia canis* and *E. chaffeensis*. Infect. Immun. 69:2083-2091.

Popov, V. L., S. M. Chen, H. M. Feng, and D. H. Walker. 1995. Ultrastructural variation of cultured *Ehrlichia chaffeensis*. J. Med. Microbiol. 43:411-421.

Popov, V. L., X. J. Yu, and D. H. Walker. 2000. The 120-kDa outer membrane protein of *Ehrlichia chaffeensis*: preferential expression on dense-core cells and gene expression in *Escherichia coli* associated with attachment and entry. Microb. Path. 28:71-80.

Reddy, G. R., C. R. Sulsona, A. F. Barbet, S. M. Mahan, M. J. Burridge, and A. R. Alleman. 1998. Molecular characterization of a 28 kDa surface antigen gene family of the tribe Ehrlichieae. Biochem. Biophys. Res. Commun. 247:636-643.

Rikihisa, Y., S. A. Ewing, J. C. Fox, A. G. Siregar, F. H. Pasaribu, and M. B. Malole. 1992. Analyses of *Ehrlichia canis* and a canine granulocytic *Ehrlichia* infection. J. Clin. Microbiol. 30:143-148.

Rurangirwa, F. R., D. Stiller, D. M. French, and G. H. Palmer. 1999. Restriction of major surface protein 2 (MSP2) variants during tick transmission of the *Ehrlichia Anaplasma marginale*. Proc. Natl. Acad. Sci. USA 96:3171-3176.

Schmidt, M. A., L. W. Riley, and I. Benz. 2003. Sweet new world: glycoproteins in bacterial pathogens. Trends Microbiol. 11:554-561.

Schwan, T. G. and J. Hinnebusch. 1998. Bloodstream-versus tick-associated variants of a relapsing fever bacterium. Science 280:1938-1940.

Singu, V., H. Liu, C. Cheng, and R. R. Ganta. 2005. *Ehrlichia chaffeensis* expresses macrophage- and tick cell-specific 28-kilodalton outer membrane proteins. Infect. Immun. 73:79-87.

Thanka Christlet, T. H. and K. Veluraja. 2001. Database analysis of O-glycosylation sites in proteins. Biophys. J. 80:952-960.

Troy, G. C. and S. D. Forrester. 1990. Canine ehrlichiosis, p. 404-418. In C. E. Green (ed.), Infectious diseases of the dog and cat. W.B. Sauders Co., Philadelphia.

Upreti, R. K., M. Kumar, and V. Shankar. 2003. Bacterial glycoproteins: Functions, biosynthesis and applications. Proteomics. 3:363-379.

Yu, X. J., J. W. McBride, C. M. Diaz, and D. H. Walker. 2000. Molecular cloning and characterization of the 120-kilodalton protein gene of *Ehrlichia canis* and application of the recombinant 120-kilodalton protein for serodiagnosis of canine ehrlichiosis. J. Clin. Microbiol. 38:369-374.

Yu, X. J., J. W. McBride, X. F. Zhang, and D. H. Walker. 2000. Characterization of the complete transcriptionally active Ehrlichia chaffeensis 28 kDa outer membrane protein multigene family. Gene 248:59-68.

Yu, X. J., P. Crocquet-Valdes, and D. H. Walker. 1997. Cloning and sequencing of the gene for a 120-kDa immunodominant protein of Ehrlichia chaffeensis. Gene 184:149-154.

Zhang, J. Z., J. W. McBride, and X. J. Yu. 2003. L-selectin and E-selectin expressed on monocytes mediating Ehrlichia chaffeensis attachment onto host cells. FEMS Microbiol. Lett. 227:303-309.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of identifying an *E. canis* or *E. chaffeensis* infection using a sample from an individual suspected of having such an infection, comprising assaying the sample for an antibody that immunologically binds a polypeptide consisting of: (a) a sequence selected from the group consisting of SEQ ID NO:45 and SEQ ID NO:22; or (b) a sequence selected from the group consisting of SEQ ID NO:25, SEQ ID NO:26, SEQ ID NO:27, SEQ ID NO:28, SEQ ID NO:23 and SEQ ID NO:24 wherein the sample is assayed by means of an immunoassay in which antibodies from the sample, if present, will bind to an immobilized polypeptide comprising a sequence at least 90% identical to the sequence of (a) or (b), and further wherein bound antibodies are detected by means of a detectable label.

2. The method of claim 1, wherein the immunoassay is a enzyme linked immunosorbent assay (ELISA), radioimmunoassay (RIA), immunoradiometric assay, fluoroimmunoassay, chemiluminescent assay, bioluminescent assay, or a Western blot.

3. The method of claim 1, wherein the sample is assayed by contacting an immobilized polypeptide comprising a sequence selected from the group consisting of SEQ ID NO:45 and SEQ ID NO:22, with said sample and detecting immunological binding of the antibody thereto.

4. The method of claim 1, wherein the sample is assayed by contacting an immobilized polypeptide comprising SEQ ID NO: 22, with said sample and detecting immunological binding of the antibody thereto.

5. The method of claim 1, wherein the sample is assayed by contacting an immobilized polypeptide comprising a sequence selected from the group consisting of SEQ ID NO:25, SEQ ID NO:26, SEQ ID NO:27, SEQ ID NO:28, SEQ ID NO:23 and SEQ ID NO:24, with said sample and detecting immunological binding of the antibody thereto.

6. The method of claim 1, wherein the sample is assayed by contacting an immobilized polypeptide comprising SEQ ID NO:23 or SEQ ID NO:24, with said sample and detecting immunological binding of the antibody thereto.

7. The method of claim 1, wherein the immobilized polypeptide comprises SEQ ID NO:45.

8. The method of claim 1, wherein the immobilized polypeptide comprises SEQ ID NO:25.

9. The method of claim 1, wherein the immobilized polypeptide comprises SEQ ID NO:26.

10. The method of claim 1, wherein the immobilized polypeptide comprises SEQ ID NO:27.

11. The method of claim 1, wherein the immobilized polypeptide comprises SEQ ID NO:28.

12. The method of claim 1, wherein the immobilized polypeptide comprises SEQ ID NO:23.

13. The method of claim 1, wherein the immobilized polypeptide comprises SEQ ID NO:24.

* * * * *